United States Patent
Taylor et al.

(10) Patent No.: US 8,785,150 B2
(45) Date of Patent: Jul. 22, 2014

(54) QUANTIFIABLE INTERNAL REFERENCE STANDARDS FOR IMMUNOHISTOCHEMISTRY AND USES THEREOF

(75) Inventors: Clive R. Taylor, South Pasadena, CA (US); Shan Rong Shi, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 1231 days.

(21) Appl. No.: 11/772,042

(22) Filed: Jun. 29, 2007

(65) Prior Publication Data
US 2008/0038771 A1    Feb. 14, 2008

Related U.S. Application Data

(60) Provisional application No. 60/817,969, filed on Jun. 30, 2006.

(51) Int. Cl.
*G01N 1/30*    (2006.01)

(52) U.S. Cl.
CPC .................................... *G01N 1/30* (2013.01)
USPC .......................... 435/40.5; 435/7.1; 435/7.92

(58) Field of Classification Search
None
See application file for complete search history.

(56) References Cited

U.S. PATENT DOCUMENTS

| | | | |
|---|---|---|---|
| 6,165,734 A | 12/2000 | Garini et al. | |
| 6,281,004 B1 * | 8/2001 | Bogen et al. | 435/287.1 |
| 6,746,848 B2 | 6/2004 | Smith | |
| 7,219,016 B2 | 5/2007 | Rimm et al. | |
| 2001/0031482 A1 * | 10/2001 | James et al. | 435/40.5 |
| 2003/0059851 A1 | 3/2003 | Smith | |

FOREIGN PATENT DOCUMENTS

| | | | | |
|---|---|---|---|---|
| EP | 0445277 | * | 7/1996 | 33/569 |
| WO | 02086498 A1 | | 10/2002 | |

OTHER PUBLICATIONS

Riera et al., Use of Cultured Cells as a Control for Quantitative Immunocytochemical Analysis of Estrogen Receptor in Breast Cancer, Am J Clin Pathol 1999, 111, pp. 329-335.*

Sompuram et al., A novel quality control slide for quantitative immunohistochemistry testing, The Journal of Histochemistry & Cytochemistry, vol. 50 (11): 2002, pp. 1425-1433.*
Kurtycz et al., Immunocytochemistry Controls Using Cell Culture, Diagnostic cytopathology, vol. 17, No. 1, 1998, pp. 74-79.*
Ranefall et al., Automatic quantification of immunohistochemically stained cell nuclei based on standard refernce cells, Analytical Cellular Pathology 17, 1998, pp. 111-123.*
Ermert L. et al. 2001. "Comparison of different detection methods in quantitative microdensitometry." Am. J. Pathol. 158(2):407-417.
O'Leary, T.J. 2001. "Standardization in immunohistochemistry." 9:3-8, App Immuno & Molecular morphology.
Pagliarulo, V. et al. 2004. "Sensitivity and reproducibility of standardized-competitive RT-PCR for transcript quantification and its comparison with real time RT-PCR." Mol. Cancer. 3:5.
Shi, S.R. et al. 1998. "Standardization of immunohistochemistry based on antigen retrieval technique for routine formalin-fixed tissue sections." Appl. Immunohistochem. Mol. Morph. 6:89-96.
Shi, S.R. et al. 2005. "Protein-Embedding Technique: A Potential Approach to Standardization of Immunohistochemistry for Formalin-Fixed, Paraffin-Embedded Tissue Sections." J. Histochem. Cytochem. 53:1167-1170.
Willey, J.C. et al. 1998. "Expression measurement of many genes simultaneously by quantitative RT-PCR using standardized mixture s of competitive templates." Am. J. Res. Cell Mol. Biol. 19:16-24.
H. Battifora, "Assessment of Antigen Damage in Immunohistochemistry the Vimentin Internal Control" American Journal of Clinical Pathology, vol. 96, No. 5, pp. 669-671, Jan. 1, 1991.
Clive Taylor, "The Total Test Approach to Standardization of Immunohistochemistry" Arch Pathol Lab Med, vol. 124, pp. 345-951, Jul. 2000.
Timothy O'Leary, "Standardization in Immunohistochemistry" Appl Immunohistochemistry & Molecular Morphology, vol. 1, pp. 3-8, 2001.
Shi et al., "Antigen Retrieval Techniques: Current Perspectives" J Histochemistry & Cytochemistry, vol. 49, No. 8, pp. 931-937, 2001.
Shi et al. "Protein-embedding Technique: A Potential Approach to Standardization of Immunohistochemistry for Formalin-fixed, Paraffin-embedded Tissue Sections" J Histochemistry & Cytochemistry, vol. 53, pp. 1167-1170, 2005.

* cited by examiner

*Primary Examiner* — Gary W Counts
(74) *Attorney, Agent, or Firm* — DLA Piper LLP (US)

(57) ABSTRACT

Methods for identifying Quantifiable Internal Reference Standards (QIRS) for immunohistochemistry (IHC). Also disclosed are methods for using QIRS to quantify test antigens in IHC.

5 Claims, 3 Drawing Sheets

QUANTIFIABLE INTERNAL REFERENCE STANDARDS FOR IMMUNOHISTOCHEMISTRY AND USES THEREOF

RELATED APPLICATION

This application claims priority to U.S. Provisional Application Ser. No. 60/817,969, filed Jun. 30, 2006, the content of which is incorporated herein by reference in its entirety.

FUNDING

This invention was made with support in part by grants from NIH (R33 CA103455-01 and R44 CA88684). Therefore, the U.S. government has certain rights.

FIELD OF THE INVENTION

The present invention relates in general to immunohistochemistry (IHC). More specifically, the invention provides methods for identifying Quantifiable Internal Reference Standards (QIRS) for quantitative analysis of formalin-fixed, paraffin-embedded (FFPE) cell or tissue samples. The invention also provides methods for using QIRS in quantitative analysis of FFPE cell or tissue samples.

BACKGROUND OF THE INVENTION

Standardization of IHC for archival FFPE tissue sections has become increasingly important due to the emergence of a new field of pathology that requires demonstration of the differential expression of various prognostic markers for individualized cancer treatment. From a practical point of view, one of the most difficult issues in the standardization of IHC for FFPE tissue is the adverse influence of formalin upon antigenicity, and the great variation in fixation/processing procedures.

SUMMARY OF THE INVENTION

The invention provides a method for identifying a QIRS for IHC. The method comprises the steps of (1) providing multiple samples of cells or tissues of the same type or different types, (2) determining the amount of a first antigen and the amount of a second antigen in each of the cell or tissue samples, (3) preparing an FFPE sample from each of the cell or tissue samples, and (4) determining the amount of the first antigen and the amount of the second antigen in each of the FFPE samples by IHC. If the ratio of the amount of the first antigen to the amount of the second antigen in the cell or tissue samples is at least 95% identical among the cell or tissue samples and the ratio of the amount of the first antigen to the amount of the second antigen in the FFPE samples is at least 95% identical among the FFPE samples, the first antigen is identified as a QIRS for the second antigen in IHC. Preferably, the amount of the first antigen in the FFPE samples is at least 50% of the amount of the first antigen in the cell or tissue samples. The amount of the first antigen in the FFPE sample may be determined using a first quantifiable label and the amount of the second antigen in the FFPE sample may be determined using a second quantifiable label. In some embodiments, the first antigen is detectable by a first antibody to the first antigen or the second antigen is detectable by a second antibody to the second antigen.

The invention also provides a method for quantifying a test antigen by IHC. The method comprises the steps of (1) providing an FFPE cell or tissue sample prepared from an original cell or tissue sample, (2) determining the amount of a QIRS for a test antigen in the FFPE sample by IHC, and (3) calculating the amount of the test antigen in the FFPE sample from the amount of the QIRS in the FFPE sample. The method may further comprise a step of calculating the amount of the test antigen in the original cell or tissue sample from the amount of the QIRS in the FFPE sample. The QIRS may be identified according to the method described above.

Normal or pathologic cells or tissues may be used to practice the methods of the invention. For example, the cells may be lymphocytes (e.g., Raji or HL60 cells), endothelial cells (e.g., HuVEC cells), fibroblasts (e.g., LD419 cells), or epithelial cells (e.g., breast cells such as MCF7, MDA, or MB468 cells), or the tissues may contain lymphocytes, endothelial cells, fibroblasts, or epithelial cells. Alternatively, the cells or tissues may be from prostate or spleen.

A QIRS may be a cell surface protein, a cytoplasmic protein, or a nuclear protein. Exemplary QIRS include but are not limited to PSA, p53, Rb, and ER. In particular, exemplary QIRS for lymphocytes include but are not limited to CD45, CD20, actin, B2 microglobulin, vimentin, histone H1, and MIB1; exemplary QIRS for endothelial cells include but are not limited to CD31, actin, B2 microglobulin, vimentin, factor VIII, histone H1, MIB1, Fli 1, CD34, and VWF; exemplary QIRS for fibroblasts include but are not limited to fibroblast surface protein, actin, B2 microglobulin, vimentin, desmin, histone H1, and MIB1; and exemplary QIRS for epithelial cells include but are not limited to Her2, EGFR, actin, B2 microglobulin, vimentin, histone H1, and MIB1.

The above-mentioned and other features of this invention and the manner of obtaining and using them will become more apparent, and will be best understood, by reference to the following description, taken in conjunction with the accompanying drawings. The drawings depict only typical embodiments of the invention and do not therefore limit its scope.

DETAILED DESCRIPTION OF THE INVENTION

Figure 1:
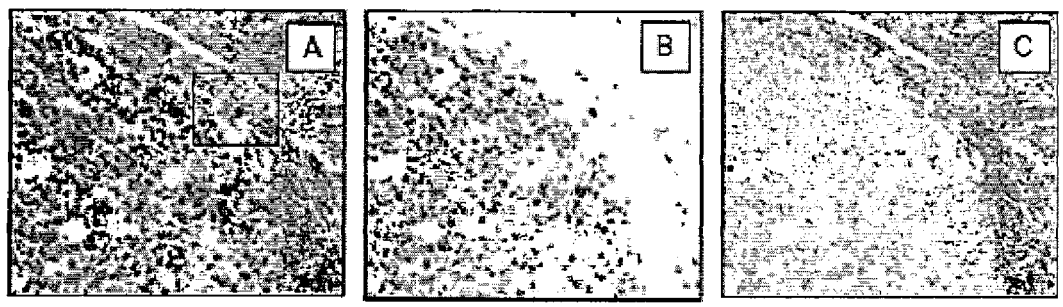
FIG. 1. Unmixing of DAB from hematoxylin: Ki67 in a lymph node germinal center imaged with a Nuance multispectral imaging system. Panel A: visual (RGB) appearance of the sample. Pane B: unmixed DAB signal. Panel C: unmixed hematoxylin signal, which accurately recapitulates the dense staining of the mantle cells and the paler staining of the germinal center. The small box indicates the region highlighted in FIG. 2.

Previous studies have demonstrated a potential approach to standardization of IHC for FFPE tissue based on optimal antigen retrieval (AR), to achieve a maximal degree of retrieval that provides a comparable level of IHC staining among various FFPE tissue sections that have been fixed in formalin from 4 hours to 7 days. On this basis, it is believed that the use of optimized AR protocols permits retrieval of specific proteins (antigens) from FFPE tissues to a defined and reproducible degree (expressed as R %), with reference to the amount of protein present in the original fresh/unfixed tissue. This belief may be explained mathematically. Suppose the amount of a protein in a fresh cell/tissue=Pf, and that Pf produces an IHC signal in fresh tissue of $f(Pf)$. When the IHC signal of FFPE is $f(Pffpe)$, then the retrieved rate of AR (R %) is calculated as: AR rate (R %)=$f(Pffpe)/f(Pf) \times 100\%$, the amount of protein in the FFPE tissue of Pffpe=Pf×R %. In a situation where optimized AR is 100% effective, then Pffpe=Pf if the IHC signal is of equal strength in fresh tissue and FFPE tissue.

The basis of QIRS is then as follows: optimized AR will be carried out for a limited panel of intrinsic tissue proteins that are uniformly present in a wide range of tissues, thereby constituting a panel of internal standards that can be accurately quantified by independent methods to form QIRS. The intensity of IHC staining obtained for other unknown proteins (test analytes) in the same tissue section, after optimized AR, may then be compared with the IHC staining of a comparable QIRS to provide a measure of the amount present of the test analyte.

This invention is comprised of a discovery process whereby certain ubiquitous proteins (analytes) that are present within recognizable cells in surgical biopsy tissues are characterized (precisely measured by weight) in order that they may serve as QIRS.

The QIRS meet two critical requirements for a quantitative assay:

1. measurement of the absolute amount of the QIRS after processing of the biopsy (FFPE) allows for calculation of loss of analytes that occurs during sample preparation (with reference to the amount present in fresh tissue), and 2. measurement of the intensity of the IHC stain reaction of the QIRS as compared to the intensity of reaction for a protein of interest (test analyte), serves as a calibration standard that permits quantification of the test analyte that is present in unknown amounts.

QIRS for IHC provide quality control for the entire staining process and are analogous to the standardized reference materials used in clinical laboratory testing, of blood or serum, where the well characterized reference standard serves as a calibration marker that allows for the precise measurement by weight of an analyte present in unknown amounts.

The essence of the invention is as follows:

1. Proteins (analytes) are selected on the basis of their widespread presence in recognizable cells in all (or almost all) tissues.

2. The exact amount of protein present on a per cell basis (averaged across 100 or 1000 cells) is measured experimentally in fresh tissue, by independent techniques, such as ELISA (enzyme linked immunosorbent assay) assay of extracts containing known numbers of the critical cell type (that contains the protein). This characterized protein constitutes a QIRS. Controlled IHC is performed on the fresh tissue and the intensity of IHC QIRS signal per cell is recorded (by computer assisted quantified image analysis) in relation to the measured amount of protein present.

3. The exact amount of the same protein (QIRS) in the same cell type is then determined experimentally (by the same methods) following sample preparation (FFPE). Controlled IHC is performed on the FFPE tissue and the intensity of IHC signal per cell is recorded (by computer assisted quantified image analysis) in relation to the measured amount of protein present.

4. Comparison of the IHC signal of the QIRS for the FFPE tissue with that of the fresh tissue then allows calculation of the loss of signal intensity attributed to loss of the reference protein during FFPE. This loss can be expressed as a percentage or as a 'coefficient' of loss due to fixation.

5. Selected proteins of interest (test analytes) that are variably present in pathologic tissues, and that require a quantitative analysis for therapeutic decisions (diagnosis or prognosis), are then subjected to the identical process under controlled conditions. The loss during sample preparation for each selected test analyte (coefficient of fixation) is then derived experimentally, and the data recorded.

6. Having established a system of QIRS as described, it is then possible to take a surgical biopsy and determine by weight the exact amount of test analyte of interest present on a cell to cell basis by employing double IHC staining using the QIRS as the calibrator with comparative spectral imaging (computer assisted image analysis).

In simple terms, the intensity of IHC stain reaction of the recognizable cell type (that contains ubiquitous characterized reference standard protein, i.e., the QIRS), is compared with the intensity of IHC stain of the cell(s) containing the 'test analyte'. Because the amount of QIRS can be measured accurately, using the data derived in establishing the QIRS, the amount present of the test analyte can be calculated.

The figures illustrate the principle by which two different IHC stains may be evaluated and compared in the same tissue section; representing the method for comparing the unknown test analyte with the QIRS.

Accordingly, the invention features a method of identifying a QIRS for IHC. The method involves providing multiple samples of cells or tissues, determining the amount of a first antigen and the amount of a second antigen in each of the cell or tissue samples, preparing an FFPE sample from each of the cell or tissue samples, and determining the amount of the first antigen and the amount of the second antigen in each of the FFPE samples by IHC.

Tissues may be obtained from a subject using any of the methods known in the art. As used herein, a "subject" refers to a human or animal, including all mammals such as primates (particularly higher primates), sheep, dog, rodents (e.g., mouse or rat), guinea pig, goat, pig, cat, rabbit, and cow. In a preferred embodiment, the subject is a human. In another embodiment, the subject is an experimental animal or animal suitable as a disease model. A "tissue" sample from a subject may be a biopsy specimen sample, a normal or benign tissue sample, a cancer or tumor tissue sample, a freshly prepared tissue sample, a frozen tissue sample, a primary cancer or tumor sample, or a metastasis sample. Exemplary tissues include, but are not limited to, epithelial, connective, muscle, nervous, heart, lung, brain, eye, stomach, spleen, bone, pancreatic, kidney, gastrointestinal, skin, uterus, thymus, lymph node, colon, breast, prostate, ovarian, esophageal, head, neck, rectal, testis, throat, thyroid, intestinal, melanocytic, colorectal, liver, gastric, and bladder tissues. Cells may be obtained, e.g., from cell culture or breakdown of tissues.

An "antigen" is any substance capable of eliciting an immune response in a subject. Exemplary antigens include but are not limited to peptides, proteins, lipoproteins, and glycoproteins. The amount of an antigen in a cell or tissue sample may be determined by methods commonly known in the art. For example, methods of measuring protein levels in biological samples usually employ antibodies (e.g., monoclonal or polyclonal antibodies) that bind specifically to target proteins. The term "antibody" refers to immunoglobulin molecules and immunologically active portions thereof, i.e., molecules that contain an antigen binding site which specifically binds an antigen. Examples of immunologically active portions of immunoglobulin molecules include F(ab) and F(ab')$_2$ fragments which can be generated by treating the antibody with an enzyme such as pepsin. Alternatively, antigens may be detected by aptamers, which are chemically synthesized (usually short) strands of oligonucleotides (DNA or RNA) that can adopt highly specific three-dimensional conformations.

To determine the amount of an antigen in a cell or tissue sample, an antibody itself, a secondary antibody that binds to the first antibody, or an aptamer can be detectably labeled. Alternatively, the antibody or aptamer can be conjugated with biotin, and detectably labeled avidin (a polypeptide that binds to biotin) can be used to detect the presence of the biotinylated antibody or aptamer. Combinations of these approaches (including "multi-layer sandwich" assays) familiar to those in the art can be used to enhance the sensitivity of the methodologies. Some of these protein-measuring assays (e.g., ELISA or Western blot) can be applied to lysates of test cells or tissues, and others (e.g., immunohistological methods or fluorescence flow cytometry) applied to unlysed tissues or cell suspensions. Methods of measuring the amount of a label depend on the nature of the label and are known in the art. Appropriate labels include, without limitation, radionuclides (e.g., $^{125}I$, $^{131}I$, $^{35}S$, $^{3}H$, or $^{32}P$), enzymes (e.g., alkaline phosphatase, horseradish peroxidase, luciferase, or β-glactosidase), fluorescent moieties or proteins (e.g., fluorescein, rhodamine, phycoerythrin, GFP, or BFP), or luminescent moieties (e.g., Qdot™ nanoparticles supplied by the Quantum Dot Corporation, Palo Alto, Calif.). Other applicable assays include quantitative immunoprecipitation or complement fixation assays.

FFPE cell or tissue samples may be prepared according to protocols commonly used in the art. Typically, sections of paraffin-embedded cells or tissues are obtained by (1) preserving tissue in fixative, (2) dehydrating the fixed tissue, (3) infiltrating the tissue with fixative, (4) orienting the tissue such that the cut surface accurately represents the tissue, (5) embedding the tissue in paraffin (making a paraffin block), (6) cutting tissue paraffin block with microtome in sections of 4-5 µm, and (7) mounting sections onto slides.

IHC is the demonstration of a cell or tissue constituent in situ by detecting specific antibody/aptamer-antigen interactions where the antibody/aptamer has been tagged with a visible label. The visual marker may be a fluorescent dye, colloidal metal, hapten, radioactive marker, or more commonly an enzyme. Experimental samples include FFPE samples. Ideally, maximal signal strength along with minimal background or non-specific staining are required to give optimal antigen demonstration. IHC protocols are well known in the art; see, e.g., Immunocytochemical Methods and Protocols (second edition), edited by Lorette C. Javois, from Methods in Molecular Medicine, volume 115, Humana Press, 1999 (ISBN 0-89603-570-0).

Generally, all paraffin embedded sections are floated on a warm water bath (45° C.) before being picked up onto microscope slides and allowed to drain.

Fixation is the most important step for paraffin embedded material. An ideal fixative should preserve the tissue and cells as life like as possible, without any shrinking or swelling and without distorting or dissolving cellular constituents; prevent putrefaction by bacteria and prevent autolysis by cathepsin containing cells; and stabilize and protect tissues and cells against the detrimental effects of subsequent processing and staining procedures. The most widely used fixatives are formalin based. The three most commonly employed fixatives for general use are neutral buffered formalin, formal saline, or as used in HMDS, 10% formalin in $dH_2O$. Formalin, like other aldehyde fixatives, forms cross linking methylene bridges and Schiff bases between basic amino acid (lysine) residues of proteins. This cross linking stabilizes the proteins in situ, which is the basis of fixation. Formaldehyde produces mild cross linkages when compared to other aldehyde fixatives such as glutaraldehyde. In addition to the choice of fixative, other important factors include fixation time, temperature and pH. Fixation time will depend upon the size of the specimen. In order to achieve adequate and consistent fixation it is essential that tissue specimens be sliced to a maximum thickness of 3 mm.

The vast majority of antigen retrieval studies have been applied to formalin fixed material. When aldehyde-based fixatives are used (e.g., formalin), inter- and intra-molecular cross-links are produced with certain structural proteins, which are responsible for the masking of tissue antigens. With aldehyde based fixatives, this adverse effect has been thought to be due to the formation of methylene bridges between reactive sites on tissue proteins. These reactive sites include primary amines, amide groups, thiols, alcoholic hydroxyl groups, and cyclic aromatic rings. The degree of masking of the antigenic sites depends upon the length of time of fixation, temperature, concentration of fixative, and the availability of other nearby proteins able to undergo cross-linkages. In order to "unmask" these antigenic sites a range of antigen retrieval techniques are available.

For example, the protein cross-links formed during formalin fixation can be partially disrupted by the use of proteolytic enzymes of which trypsin is the most widely used. Trypsinization time is extremely important and is proportional to the specimen fixation time. There is a very fine balance between over and under digestion. Trypsin is optimally active at 37° C. and at pH 7.8. The reaction rate is improved by the addition of the co-enzyme calcium chloride (0.1%). Trypsin only remains active for about 30 minutes; therefore if the incubation time exceeds this, the working solution must be replaced. Not all antigens require proteolytic digestion. Furthermore, care must be taken to avoid creating "false" antigenic sites, as some antigens may be altered or destroyed by trypsinization. In some instances immunostaining may be impaired or completely removed following trypsinization. Proteolytic digestion has largely been replaced by heat mediated antigen retrieval methods.

The rationale behind these heat pretreatment methods is unclear and several theories have been postulated. One theory is that heavy metal salts act as a protein precipitant, forming insoluble complexes with polypeptides and that protein precipitating fixatives frequently display better preservation of antigens than do cross-linking aldehyde fixatives. Another theory is that during formalin fixation inter- and intra-molecular cross methylene bridges form linkages and weak Schiff bases. These cross linkages alter the protein conformation of the antigen such that a specific antibody may not recognize it. It is postulated that heat mediated antigen retrieval removes the weaker Schiff bases but does not affect the methylene bridges so that the resulting protein conformation is intermediate between fixed and unfixed.

Antigens masked during routine fixation and processing can be revealed by using high temperature, heat mediated antigen retrieval techniques; microwave oven irradiation, combined microwave oven irradiation and proteolytic enzyme digestion, pressure cooker heating, autoclave heating, water bath heating, Steamer heating, or high temperature incubator.

One exemplary IHC protocol is as follows:

I. Preparation of Sections

Prepare slides according to A. or B.

A. Deparaffinization

1. Label all slides clearly with a pencil, noting antibody and dilution.
2. Deparaffinize and rehydrate as follows: three times for 5 minutes in xylene; two times for 5 minutes in 100% ethanol; two times for 5 minutes in 95% ethanol; and once for 5 minutes in 80% ethanol.
3. Place all sections in endogenous blocking solution (methanol+2% hydrogen peroxide) for 20 minutes at room temperature.
4. Rinse sections twice for 5 minutes each in deionized water.
5. Rinse sections twice for 5 minutes in phosphate buffered saline (PBS), pH 7.4.

B. Deparaffinization and High Energy Microwave Antigen Retrieval

1. Label all slides clearly with a pencil, noting antibody and dilution.
2. Deparaffinize and rehydrate as follows: three times for 5 minutes in xylene; two times for 5 minutes in 100% ethanol; two times for 5 minutes in 95% ethanol; and once for 5 minutes in 80% ethanol.
3. Place sections in a Coplin jar with dilute antigen retrieval solution of choice (e.g., 10 mM citric acid, pH 6). Completely cover the slide.
4. Place Coplin jar containing slides in vessel filled with water and microwave on high for 2-3 minutes (700 watt oven).
5. Check level of retrieval solution, allow to cool for 2-3 minutes, and repeat steps 3 and 4 four times (depending on tissue). Completely cover the slide.
6. Remove Coplin jar containing sections and allow to cool for 20 minutes at room temperature.
7. Rinse sections in deionized water, two times for 5 minutes.
8. Place slides in modified endogenous oxidation blocking solution (PBS+2% hydrogen peroxide).
9. Rinse slides once for 5 minutes in PBS.

II. Blocking and Staining

1. Block all sections with PBS/1% bovine serum albumin (PBA) for 1 hour at room temperature.
2. Incubate sections in normal serum diluted in PBA (2%) for 30 minutes at room temperature to reduce non-specific binding of antibody. Perform the incubation in a sealed humidity chamber to prevent air-drying of the tissue sections.
3. Gently shake off excess antibody and cover sections with primary antibody diluted in PBA. Replace the lid of the humidity chamber and incubate either at room temperature for 1 hour or overnight at 4° C.
4. Rinse sections twice for 5 minutes in PBS, shaking gently.
5. Gently remove excess PBS and cover sections with diluted biotinylated secondary antibody in PBA for 30 minutes-1 hour at room temperature in the humidity chamber.
6. Rinse sections twice for 5 minutes in PBS, shaking gently.
7. Remove excess PBS and incubate for 1 hour at room temperature in Vectastain ABC reagent (as per kit instructions). Secure lid to humidity chamber to ensure a moist environment.
8. Rinse twice for 5 minutes in PBS, shaking gently.

III. Development and Counterstaining

1. Incubate sections for approximately 2 minutes in peroxidase substrate solution made up immediately prior to use as follows:

10 mg diaminobenzidine (DAB) dissolved in 10 ml 50 mM sodium phosphate buffer, pH 7.4;
   12.5 µl 3% $CoCl_2/NiCl_2$ in deionized water; and
   1.25 µl hydrogen peroxide.

2. Rinse slides well three times for 10 minutes in deionized water.
3. Counterstain with 0.01% Light Green acidified with 0.01% acetic acid for 1-2 minutes depending on intensity of counterstain.
4. Rinse slides three times for 5 minutes with deionized water.
5. Dehydrate two times for 2 minutes in 95% ethanol; two times for 2 minutes in 100% ethanol; and two times for 2 minutes in xylene.
6. Mount slides.

A QIRS is identified by comparing the ratio of the amount of the first antigen to the amount of the second antigen in the cell or tissue samples before and after the FFPE process. The original cell or tissue samples (i.e., before the FFPE process) and the FFPE samples (i.e., after the FFPE process) may be prepared by different people, at different times, in different labs, or following different procedures. If both ratios are consistent (e.g., at least 95% identical) among all samples before and after the FFPE process, respectively, the first antigen is identified as a QIRS for the second antigen in IHC. The ratios of any member of the group consisting of (1) the amount of the QIRS in the original cell or tissue sample, (2) the amount of the second antigen in the original cell or tissue sample, (3) the amount of the QIRS in the FFPE sample, and (4) the amount of the second antigen in the FFPE sample to another member of the group are "standard ratios."

A QIRS so identified may be used to quantify a test antigen by IHC. The method involves providing an FFPE cell or tissue sample prepared from an original cell or tissue sample, determining the amount of a QIRS for a test antigen in the FFPE sample by IHC, and calculating the amount of the test antigen in the FFPE sample or the original cell or tissue sample from the amount of the QIRS in the FFPE sample. For example, when the standard ratios of the amount of the test antigen to the amount of the QIRS in the original cell or tissue sample (A), the amount of the test antigen to the amount of the QIRS in the FFPE sample (B), and the amount of the QIRS in the original cell or tissue sample to the amount of the QIRS in the FFPE sample (C) are known, the amount of the test antigen in the test FFPE sample may be calculated as [the amount of the QIRS in the test FFPE sample]×(B), and the amount of the test antigen in the test original cell or tissue sample may be calculated as [the amount of the QIRS in the test FFPE sample]×(C)×(A).

The following examples are intended to illustrate, but not to limit, the scope of the invention. While such examples are typical of those that might be used, other procedures known to those skilled in the art may alternatively be utilized. Indeed, those of ordinary skill in the art can readily envision and produce further embodiments, based on the teachings herein, without undue experimentation. All publications cited herein are incorporated by reference in their entirety.

EXAMPLES

Example I

Quantification of Immunohistochemistry—Issues Concerning Methods, Utility and Semi-Quantitative Assessment Summary Immunohistochemistry now is entering its fourth decade of use on formalin fixed paraffin embedded tissues. Over this period the method has evolved to become a major part of the practice of diagnostic surgical pathology worldwide. From the beginning immunohistochemistry has been adapted to provide a range of markers of cell lineage and tissue type, with particular application to the diagnosis and classification of tumors. In this modality immunohistochemical methods were employed simply as 'special stains', the results of which were evaluated quantitatively by the pathologist, as for any other stain. More recently, attention has shifted to the demonstration of prognostic markers in tumor cells, driven by the advent of molecular biology and the discovery of numerous regulatory molecules, coupled with manufacture of the corresponding specific antibodies. Immunohistochemistry has rapidly adapted to this new use, but in so doing the demand for some form of quantification has become paramount; it is no longer enough that the 'stain' is there; rather it is a question of "How much is there?" This review explores the limitations of immunohistochemistry when employed in a semi-quantitative mode, and explores the possibility of fulfilling the full potential of immunohistochemistry, as a true quantitative immunoassay applied in a tissue section environment.

Definitions

Quantity (noun): 1 a certain amount or number, 2 the property of something that is measurable in number, amount, size or weight, 3 a considerable number or amount (from Latin, quantitas—how much?).

Quantitative (alt. quantitive) (adjective): of, concerned with, or measured by, quantity. (Oxford Dictionary Compact Edition, Oxford University Press, 2002).

The term "semi-quantitative" lacks clear definition, but would imply having some of the features of "quantitative", as in "semi-precious", or not quite precious.

While these definitions have some clarity in certain contexts, the use of the term "quantitative" in Anatomic Pathology is uncommon and inconsistent. By way of contrast, within the Clinical Laboratory many assays are quantitative, and the characteristics that make up a quantitative assay can there be examined at leisure.

Anatomic pathology (surgical pathology, histopathology) per se is primarily observational, dependent upon pattern recognition in its broadest sense, without overt acknowledgement that within the context of pattern recognition there are elements that are quantitative. Biological stains, introduced in the mid-19$^{th}$ century [review, Conn's Biological Stains (1)], lend tinctorial properties to the tissue section. The interpretation of even the simple routine H&E stain does include elements of a quantitative assessment, albeit mostly at a subconscious level. Are the nuclei more or less blue (hyperchromatic)? Is the cytoplasm of the cardiac myocytes pinker than normal (hypereosinophilic), as in the early phases of myocardial infarction? What amount of atypia is present? These evaluations are made subjectively, with experience as the reference point, and formal quantitative methods are not usually employed, except for particular defined purposes (2). Assessment of the degree of malignancy, formalized in some instances into grading criteria, again includes quantitative elements, such as the number of mitotic figures (sometimes going so far as to offer a count per high-power field), or the number of large cells versus small cells in a population, as in the grading of diagnosed follicular center cell lymphomas of B cell origin. Underlying these "semi-quantitative" approaches there is the subliminal concept of a covert reference standard, against which judgments, rather than "measurements", can be made. Often this standard is crude as in the use of a "normal histiocyte" nucleus to separate large from small in the grading of FCC lymphomas, and the level of diagnostic agreement amongst different observers, including experts, is disturbingly poor [about 60% in this instance—The Non-Hodgkin's-Lymphoma Classification Project (3)].

Faced with the limited application of quantitative methods in day-to-day surgical pathology, a comparison with the quantitative methods in use in Clinical Pathology is of real value in determining how to improve the situation. Biological stains (including those based on aniline dyes) that are the basis of the usual histopathologic stains are somewhat difficult to control in terms of intensity of color (stain), from cell to cell and more so from section to section (different tissues on different days), although this may change with the advent of new generations of automated stainers. An immunohistochemical (IHC) reagent, by contrast, has the potential to provide quantitative data, for although we are not accustomed to thinking of it as such, it is in potential, if not in fact, an "immunoassay" performed in situ on the tissue section. An IHC "stain" is strictly analogous to an ELISA (enzyme-linked immunosorbent assay) test performed in the clinical lab, and ELISA tests are widely recognized as being truly quantitative (if properly performed). Exactly the same reagents that are employed in an ELISA test on serum, for example, an assay for insulin, may be employed to perform an IHC stain for insulin in a paraffin section. It is a curious oversight of scientists in general, and pathologists in particular, that the principles and reagents used in one environment are accepted as providing a strictly quantitative result (ELISA-serum), but when applied to a tissue section (IHC), are addressed only as a "stain".

Factors to be Addressed in Establishing Quantitative IHC Methods; Towards an IHC Assay as Opposed to an IHC Stain There have been several schools of thought as to the reason why IHC "stains" are difficult to run in a manner that lends itself to quantitative analysis. If there is a consensus, it is that several reasons conspire together; these may conveniently be grouped into three general areas (Table 1).

TABLE 1

The Total Test, adapted from the earlier proposal of the US Biologic Stain Commission (4), and modified from "Immunomicroscopy: A Diagnostic Tool for the Surgical Pathologist," Taylor C R and Cote R J (5).
The Total Test Pre-analytical:

Specimen handling, from operating room to histology lab
Fixation: total fixation time, and type of fixative
Paraffin embedding, storage and sectioning
De-paraffinization
Analytical:

Antigen retrieval (exact method)
Assay (staining) method and protocol
Reagent validation
Controls (Reference Standards)
Technologist and laboratory certification
Proficiency testing and quality assurance
Post-analytical:

Reading of result(s)/scoring/quantification
Report
Turn-around time
Outcomes analysis/economics/reimbursement Possibly the overriding factor in effecting significant change would be to transform the mindset of pathologists, at least of the next generation, such that the end-result of an IHC protocol would come to be regarded NOT as just a stain, but rather as a precise immunoassay that is strictly quantifiable, if properly performed and controlled, similar to any other immunologically based assay of like principle (such as ELISA).

It would seem evident that in order to achieve a quantifiable result with an IHC stain, thereby converting it to a quantifiable immunoassay, the total assay (staining process) must itself first be standardized (6-10). Those areas in assay performance that lead to significant variability or errors, and are therefore targets for improvement, are reviewed below.

Pre-Analytic Issues: Transportation, Fixation Sectioning

Pre-analytical issues fall under the broad rubric of "sample preparation" (Table 1). This area is the least well controlled of all phases of the IHC staining process (6,11), and the least controllable, because of the ways in which tissues are obtained from diverse hospital and clinic settings. At long last the importance of good sample preparation in cancer diagnosis, or misdiagnosis, particularly with regard to measurement of prognostic and predictive markers, has reached the national consciousness in the United States, with issuance of requests for proposals from the NCI (RFA-CA-07-003: Innovations in Cancer Sample Preparation, U.S. National Cancer Institute, 2006).

In the 'routine' environment of diagnostic surgical pathology, specimens that ultimately may be subject to IHC analysis may be obtained by fine-needle aspiration, or from the operating room by biopsy, or by more extensive therapeutic surgical procedures. Following removal of the tissue from the body, autolysis generally is arrested by immersion in a fixative. By far the most commonly employed fixative is formalin (in common practice a 4% solution of formaldehyde) (6,11, 12). Other fixatives have been employed, and others are being explored, in order more effectively to meet some of the current needs for performing molecular analyses of tissues or cells (13). Formalin has many advantages, not least a long tradition of use and the fact that it yields good morphologic detail; or rather it yields the morphologic detail we are accustomed to, which is deemed the equivalent of good. Formalin also is inexpensive, easily stored (with some reservations as to quality), and universally available. Formalin, therefore, is what we have, and what we must learn to work with for the immediate future.

Recognizing that the autolytic process begins immediately, the routine practice is to place the excised tissue directly in formalin, prior to leisurely transportation the laboratory, with emphasis on leisurely. Once in the surgical pathology suite ("grossing" room) the specimen is cut in, meaning that if not already sufficiently small it is cut into small blocks to facilitate rapid penetration by the fixative (formalin penetrates relatively slowly), and placed in fresh fixative for further processing. Whereas the ideal time for fixation of a 5-mm-thick tissue block is perhaps 12-24 hours [no uniform agreement here (11,12)], in practice, the total time in fixative is very variable, due to differing transportation times to the laboratory and accumulation of specimens for batch processing. Fixation time in reality is almost entirely uncontrolled, varying anywhere from 6-24 hours, or more. Add to this, questions as to whether the formalin is freshly prepared and adequately buffered, plus variability in the rate of penetration of formalin in different types of tissues and into differently sized blocks, and the result is a major impediment to standardization of an IHC stain, and an obstacle to quantification.

As an aside, in-situ-hybridization (ISH) methods have a probe-target pairing that is not immunologically based, and thus strictly do not fall under the title of IHC. Nonetheless, the principles are closely analogous, particularly with reference to interpretation and scoring. For RNA analysis by ISH methods, there is a further complication, namely the rapid degradation of RNA by intrinsic enzymes, probably beginning as soon as the blood supply to the tissue is interrupted as part of excision. For useful results, and certainly for quantification, it is essential, therefore, to process such materials immediately, and control over transportation time becomes critical so as to minimize the time elapsed prior to complete fixation.

Following fixation, the process of embedding in paraffin, and subsequent de-paraffinization of the cut sections, also involves exposing the tissues (and therefore the analytes) to a series of chemicals and to heat. The end-result is a formalin-fixed paraffin embedded (FFPE) tissue section. While anecdotes exist, there are no good data as to the adverse effects of processing upon the various analytes that might be detected by IHC staining. This aspect, therefore, is usually ignored, but in the absence of data it appears sensible that these steps of the overall preparation of the tissue section are performed as consistently as possible.

The importance of consistent sectioning may also be overlooked. For routine staining a precision microtome is used to achieve a section thickness of about 5 µm. A nucleus that is 5 µm in diameter may thus be entirely within the plane of the section, or only partially included, with effects upon the apparent intensity of a nuclear IHC stain, all other things being equal. Thicker sections may manifest the same problem even for quite large nuclei, whereas generally thinner sections will minimize it. Uniform preparation of FFPE sections that are less than 5 µm in thickness is not possible; plastic embedding media, or other special media, allow consistency in sectioning down to 1 µm, but do not lend themselves well to routine use, or to larger blocks. Even slight variations in thickness, over a 5 µm section, due to "chatter" or unevenness of cut, may also produce changes in intensity of the staining reaction that are inapparent to the naked eye, but are readily appreciable using quantitative imaging techniques. (6).

Analytical Issues: Antigen Retrieval, Protocols, Reagents, Controls

Antigen retrieval, considered here as part of the analytic process, has shown spectacular benefits in terms of the ability of all and sundry to achieve a positively stained FFPE section, but there have been some unexpected and unwanted consequences (5,14,15,16). The fact that many antigens, that hitherto could be stained only with difficulty, now are readily demonstrable following AR has led to renewed laxity with regard to fixation, and to diminished efforts in developing alternative and superior fixatives. The AR method itself is also open to great variation in practical performance, and this may affect the intensity of stain achieved, or even the number of cells that are perceived as demonstrating a positive staining reaction. Also the degree to which any particular antigen is "retrieved" is entirely unknown with reference to the absolute amount present post-fixation (in the FFPE section), and the amount present post-fixation is itself not known with reference to the amount present (per cell) when the tissue was first removed from the body (fresh, prior to sample preparation—"pre-fixation"). Some standardization may be achieved through the practice of testing the different variables in the retrieval process (method of heating, temperature, time, pH, etc.) to achieve the optimal AR protocol for each specific antigen using a defined set of reagents and staining methods (5,15). This approach would seem to risk the possibility of uncovering significantly different AR protocols for many antigens, but in practice yields only three major variations of the basic AR method, one of which will generate excellent results for the great majority of clinically relevant antigens (5,15).

Reagents and staining protocols, once seen as the primary impediment to qualitatively reproducible staining, are now regarded as perhaps the least of the difficulties, providing that certain procedures are followed, a tribute to the fine efforts of the Biological Stain Commission/FDA working groups more than a decade ago (4,17). A common error is to neglect to read the package insert for each new reagent carefully; at a minimum, perusal will provide performance characteristics (does it work on FFPE sections?) and expected patterns of staining. It should also provide a detailed staining protocol, with a judicious reminder that should a laboratory choose to depart from the protocol, then validation becomes the entire responsibility of the performing laboratory. In any event, every new reagent introduced into the laboratory, whether a primary antibody, or a different labeled antibody system, must undergo an initial validation by the laboratory to establish the performance characteristics. So called positive-control tissues serve this purpose, and properly should have been fixed and processed in a manner identical to the test specimens (same fixative, fixation time, etc.) (4, 5, 8, 18,19). Tissue microarrays are useful in evaluating a new primary antibody, allowing a quick and efficient study of the pattern of staining on potentially hundreds of tumor or tissue types, in duplicate or triplicate, deposited on a single slide. These basic control sections serve to validate qualitatively the reagents and protocol, but as usually constituted cannot serve as absolute reference materials for calibration and quantification. This limitation is because the control materials themselves, while demonstrably positive in a qualitative sense, have been fixed and processed in ways that preclude knowing, in absolute terms, how much of the test analyte is present post-fixation; it is merely that there is enough to detect a positive staining reaction with the reagents and protocol employed. Indeed the amount of analyte present pre-fixation (when fresh) also is totally unknown.

From this brief review it is argued that the 'total test' must be standardized in order for any conceivable quantitative scoring method to achieve a useful degree of reliability. Even so, for all the reasons described, the best that can be achieved today is a 'semi-quantitative' type of assay, absent availability of a defined reference standard.

It follows that a primary requirement should be to develop reference materials that can be used to establish the integrity of the sample, as well as to standardize the assay and to calibrate the results. The criteria for such a standard can be derived once more by extrapolation from Clinical Pathology (Table 2).

TABLE 2

Summary of desirable characteristics of any reference standard that would provide a basis for accurate quantification of IHC (or ISH) (19). Immunohistochemical Reference Standard: Requirements It must be subjected to the same rigors of sample preparation (fixation) as the "test" tissue.
It must be integrated into all phases of the test (assay) protocol, including evaluation of the result.
It should contain a known amount of the analyte(s) subject to assay
It should be universally available
It should be inexhaustible and inexpensive For IHC these requirements are exacting, and have yet to be fully met in a practical sense. As discussed above, the usual positive-control tissue employed in laboratories meets only some of these requirements, as does the FDA-approved Her2-kit produced by Dako (HercepTest, Dako, Glostrup, Denmark, or Dako USA). In all instances the most important deficiency is the lack of data relating to the absolute amount of the analyte present in the control material prior to the first step of the total test (i.e., prior to specimen preparation/fixation). Efforts to meet the requirements set forth in Table 2 have been few, but do show some promise in the use either of peptide deposits (20,21), cell lines (including cell-line blocks) (22,23), or faux tissues (histoids) [Marylou Ingram and Ashraf Imam, unpublished collaboration, 2005; see reference (5), p. 35, FIG. 1-27]. Another proposed approach is to use Quantifiable Internal Reference Standards, the characteristics of which have been measured by experimental observation under differing conditions of formalin-fixation, paraffin-embedment and antigen-retrieval (19). Such internal standards, once established in terms of absolute quantity of analyte per specific cell type, have the potential to serve as calibration points for test analytes demonstrated in adjacent cells by double-IHC stain methods, using multiplex-capable imaging techniques that are described later.

Lacking quantifiable internal reference standards for calibration, all IHC stains at best can only be semi-quantitative, comparing the intensity of stain, or the number of positive cells, or both, with the control, or with other cases, with results that are relative, not absolute.

Post Analytic: Results and Interpretation (Scoring)

One school of thought held that the lack of reliability of IHC methods for measurement of estrogen- or progesterone-receptor expression was attributable to the nature of the "semi-quantitative" scoring process, and the intrinsic deficiencies of an observer-based, subjective manual method. The underlying belief was that, however clearly the criteria are set forth, the application of such criteria and the reporting of the outcome will vary from pathologist to pathologist, or even for the same pathologist from day to day. Computer assisted image analysis was a touted solution to the scoring of IHC stains, where a quantifiable result was the desired outcome. Comparative studies (7,9,24,25) indeed do show that under controlled circumstances image analysis is superior to manual methods as performed by most observers.

The problem of interpretation of an IHC stain should not be minimized. With basic lineage-related markers, the problem of consistent evaluation is real, even with reference to relatively simple questions: is the cell or tissue positive for kappa chain or ER or CD30, or is it not? Is specific staining present or not, with reference to the controls? Where is the staining localized? How much staining is there (begging the questions as to whether the amount of staining correlates with the absolute amount of antigen)? What scoring system should be used and how reproducible is it? The general consensus is that IHC methods, applied as qualitative 'special' stains, if properly applied and interpreted, increase the accuracy of diagnosis in surgical pathology, as is well established by studies of lymphoma (3). However, it is known, though not often publicly acknowledged, that the eyes and brains of different observers do not see and interpret the same H&E section the same way (18,26,27). For IHC stains the variability of interpretation may be even greater, as is revealed in some of the proficiency-testing exercises carried out by the CAP (College of American Pathologists, Chicago, USA) and UK NEQAS-ICC (United Kingdom, National External Quality Assessment Scheme Immunocytochemistry). It turns out that the answers are dependent not only upon the experience and acuity of the eye of the beholder, but also upon the integrity of the staining process as already emphasized (6,7,9,10,28,29,30).

With respect to prognostic markers the problem of inter-observer consistency is much greater, requiring not just a decision as to whether there is specific positive staining, or not, but some sort of scored or semi-quantitative result. The inherent difficulties are well recognized for such commonly tested analytes as ER and PR (28), where commercially available reference standards are not usually available, and where both methodology and scoring vagaries contribute to error. The problem is arguably even greater for Her 2 (29, 30). The FDA-approved Dako kit contains a cell-line standard and includes instruction about how to read the result, and most published reports utilize some form of reference control. Even with these important provisions, scoring of the same cases for Her2, ER and PR by residents and pathologists shows clinically important variations and is short of the desired uniformity (28,29,30).

Some investigators believe that the solution to the problem of interpretation, especially the quantitative or scoring aspects of interpretation, may be found in improved methods of image analysis (7,9,24,25). Methods and instruments currently exist that yield improved results; many of these instruments are available commercially. At present, the larger reference laboratories are more likely to use such aids than smaller laboratories, or even academic centers. In part this is a matter of economics; the instruments are expensive and hard to justify where volumes are insufficient, or where special expertise cannot be developed and committed to their operation. In part it is a reflection of the fact that image analysis still requires interactive input by the pathologist, and that often leads to increased time requirements for reading the assay without conclusive evidence that the result is of more value clinically. Nonetheless, a visit to the exhibitor display at any of the major pathology meetings leaves little doubt as to which way the wind is blowing, as reviewed in the following paragraphs.

The last decade has seen enormous advances in the capabilities of image analysis systems applied to tissue sections, both in software and hardware, especially in digital cameras and in data management of the resulting large files. However, realization of the potential for increased accuracy in the post-analytic phase of the assay has served to focus renewed attention on the basic deficiencies of the IHC staining process as a whole, and its intrinsic lack of reproducibility, as discussed in the first part of this article. Even the most sophisticated image analysis hardware/software system cannot produce accurate results if the underlying stain (read immunoassay) itself suffers from non-reproducibility or significant non-linear behavior. In this context accuracy (and reproducibility) can only be determined if rigorous quantifiable reference standards (19) are available and are used to calibrate the system. The notion of accuracy should embrace not only the measurement of an analyte in a particular section, validated against a reference standard, but also the ability to repeat the result on the same case, day to day, in the same and in different laboratories, and the ability to measure the same (and ultimately different) analyte(s) in different specimens and cases, again reproducibly. Thus standardization of the overall assay must proceed hand-in-hand with accurate and reliable reading (scoring) of the assay; both are essential for achievement of an IHC stain, which in practice could be, and should be, more than just a stain but rather a system of controlled and interlocked processes, analogous to immunoassays in the clinical laboratory.

Finally, expression-array-based research has emphasized that pathology and in particular, cancer biology, reflects the simultaneous workings of multiple molecular pathways. For maximum relevance, these should be assessed on a per-cell, rather than a per-tissue-slice basis, since ultimately cells are the units of behavior, and their individual phenotypes are the relevant metric. In a practical sense this implies multiplexed molecular (IHC or ISH) assays in which more than one analyte is assessed on a tissue section at one time, in identifiable individual cells. As can be imagined, in addition to the imaging challenges this may pose, it also amplifies all the demands on controls and standards elaborated above.

Image Analysis, Approaches and Systems

While image analysis of molecular labels can include a number of applications, the following section will be limited to the discussion of the problem of estimating abundance of stains in histological tissue, with an emphasis on IHC as opposed to immunofluorescence. The previous section has addressed issues of sample preparation and provision of appropriate controls that can ensure that the IHC procedures have generated a valid signal for the imaging system to capture. The assumption is made that the signal on the slide is representative and in some way quantitatively related to the abundance of the antigens in the tissue section, which in turn is related, albeit in ways unknown, to the absolute amount of the analyte in the original tissue. The example used herein will be estimation of nuclear antigens rather than membrane-staining, since the latter may require additional considerations beyond simple intensity measurements, such as spatial patterns of expression that have their own subtleties. In addition this review will not dwell on the well-documented subjectivity and intra- and inter-observer variability of manual, visual-based semi-quantitative estimation of intensity or even of per-cent-positivity (31,32), and will simply postulate that properly designed automated imaging methods, because they are immune to the consequences of fatigue and subjectivity, can outperform human observers, certainly in terms of precision and quantitative reproducibility.

Factors that affect performance of the imaging system include the choice of camera and illumination source, the optical performance of the stains themselves, as well as the presence and degree of multiplexing. After image acquisition, it is then necessary to deploy appropriate mathematical techniques to extract quantitative intensity and area measurements from the imaging data.

Imaging Hardware: RGB Vs. Multispectral Approaches

There is a long history of the application of image processing to pathology samples (33). While some early automated imaging systems employed grayscale cameras and filter wheels to collect images, most current brightfield (transmitted light) pathology imaging systems rely on standard color cameras similar in many respects to consumer digital cameras. These typically employ a Bayer-pattern color mask over a CCD or CMOS detector, and use various algorithms to process the raw image data to generate color images that can be presented to the pathologist, and that are also used in downstream automated analysis. Single-chip, Bayer-pattern red-green-blue (RGB) cameras that are often employed, especially in many "home-grown" systems, can generate imaging artifacts, especially with respect to fine structures or edges, and have poorer spatial fidelity than more expensive 3-chip systems in which separate pixel-registered cameras are used to acquire simultaneously red, green and blue images. While the simple acquisition of good-looking color images is appealing, RGB detectors can introduce significant problems when one is trying to achieve quantification and inter-instrument precision. There are a number of ways that variation arises. For example, color values can vary significantly with the color temperature of the illumination source, different color-correction routines in camera firmware can play a role in the exact color values that are reported out, and different camera chips have differing spectral responsiveness. Some cameras employ automatic gain control or related circuitry designed to "optimize" image quality, with unpredictable effects on resulting images.

Even if an RGB imaging system is working perfectly, there are intrinsic limitations to its ability to distinguish between similar chromogens, and even more challengingly, to be able to "unmix" such signals if they overlap spatially. "Unmix" in this sense means to isolate the optical signal from each chromogen so that each can be measured quantitatively, and separately. Signal processing theory suggests that at least n if not n+1 measurements are needed to unmix n signals. In theory, therefore, it is impossible to unmix more than 3 chromogens with an RGB sensor. In practice, while it is possible to do a good job unmixing DAB (brown) from hematoxylin (blue), it has proven extremely difficult to unmix brown from red from blue (a typical combination of stains for a double-labeled sample), using only RGB measurements, due to the color-overlap of the spectral profiles. To accomplish such tasks properly, true multispectral imaging approaches may be necessary.

Spectral Imaging

Spectral imaging microscopy represents a technological advance over visual or RGB-camera-based analyses. By acquiring a stack of images at multiple wavelengths, spectral imaging allows the determination of precise optical spectra at every pixel location. With this spatially resolved spectral information in hand, it is possible to enhance the utility of IHC and ISH stains, and even the standard biologic stains used in surgical pathology. There are a number of ways to perform spectral imaging, reviewed in (24,35). The focus in this review is on the commercially available liquid crystal tunable filter-based system (Nuance™, CRi, Woburn, Mass.), from which all examples here will be drawn; this is not to imply that the Nuance system is the best or only approach, merely that it is the model with which the authors have had most experience. This system is suitable for both brightfield and fluorescence imaging. Under automatic control, a series of images (from 3 to as many as 20 or more) are taken from blue to the red (e.g., 420 nm to 700 nm) and the resulting image "stack" or "cube" is assembled in memory in such a way that a spectrum is associated with every pixel. The ability to sample the spectrum with many discrete wavelength regions spanning the visible wavelength range allows for accurate unmixing of multiple spatially co-localized chromogens, even if they are similar in color and have largely overlapping absorption spectra. Thus, it becomes straightforward to separate dark reds from light browns, or even varieties of blue stains (hematoxylin vs. NBT-BCIP) (36,37).

Image Processing and Unmixing

The key process, either with RGB images or multispectral datasets, is to partition the overall signal in a given pixel correctly into its component species. Linear unmixing algorithms (as described in (38,39,40)) rely on the signals adding together linearly. This is true with fluorescent dyes (which emit light), but this is not the case with chromogens imaged in brightfield, since they absorb light. Fortunately, the Lambert-Beer (or simply Beer's) law relating concentrations to absorbance indicates that when the transmission data is converted to optical density (absorbance) units, linearity is restored, and quantification and unmixing (39) can be successfully achieved. There are many benefits attendant on the conversion to optical density (OD), which is typically performed by taking the negative (base 10) log of the transmitted image divided by the illumination (usually a clear area on the microscope slide). First, absorbance values are an intrinsic property of the sample, and do not depend on vagaries of illumination or camera responsivities. This means that absorbance measurements of a given specimen performed on any appropriate system should, in theory, be comparable. Secondly, in the process of creating an absorbance image, flat-fielding is automatically performed, which removes the effects of uneven illumination and minor flaws in the optical train. Conversion to OD can be performed on monochrome, RGB or multispectral images.

OD (absorbance) units are dimensionless and logarithmic: so that zero absorbance means all photons transmitted; an OD of 1.0 absorbs 90% of all photons, and an OD of 2.0 absorbs 99% of all potentially detected photons. IHC stains can individually generate signals of 1 OD. Accordingly, having 2 or more dense and overlapping stains can result in virtually black deposits from which little or no useful spectral or quantitative data can be recovered. This, plus the lesser dynamic range achievable with IHC vs. fluorescence-based approaches may mean that immunofluorescence may be preferable or necessary for some applications (32). Nevertheless, IHC has some practical advantages over immunofluorescence, including the fact that pathologists prefer it largely because it allows integration of 'phenotypic' features in the IHC stain with the traditional morphologic features, long the 'gold standard' for diagnosis.

An important caveat is that the optical properties of the chromogens will affect the linearity and dynamic range of the assay. The Lambert-Beer law that underlies the unmixing approach applies only to pure absorbers. Some chromogens, most notably the popular brown DAB stain, exhibit scattering behavior similar to that of melanosomes. In fact, it can be impossible to separate DAB from melanin pigmentation spectrally, since their spectra arise from the same optical properties. However, in practice, this does not seem to pose insuperable problems, since linearity and reasonable dynamic range can be achieved using DAB approaches (41). Other chromogens, such as Vector Red, have been shown to have excellent linearity and dynamic range (42).

In addition to the specific molecular labeling procedure, a counterstain is almost always applied. Thus the challenge for quantitation begins with the unmixing of the chromogen (typically DAB) from the counterstain (typically hematoxylin). The latter pair can be successfully unmixed using simple RGB imagery if conversion to OD is performed (39), but other pairs may not be so amenable. One of the challenges (see below) is the accurate determination of the spectra of the chromogens as input values into the unmixing procedure. Small variations in the spectra chosen can have quite dramatic effects on the calculated abundance values. While in many cases it suffices to measure the spectrum of the isolated chromogens (single stain, no counterstain), we have found that it may be necessary to measure the spectrum of the chromogens in the actual sample, after all the staining procedures have been performed, since the spectra can be affected by the presence of other dyes and reagents.

Multiplexing

Typically, only a single IHC-chromogen-antigen combination is used per slide; if more than one antigen is to be analyzed, serial sections are made and a different antibody is applied to each. This procedure benefits from simplified protocols and quality control regimens compared to multicolor techniques, but generates more slides and possibly more preparation steps than if the reagents are 'multiplexed' on a single slide. Moreover, multiple molecular events cannot be evaluated on a per-cell basis when parallel sections are employed, and this capability is very important in establishing the phenotype of individual tumor cells (e.g., lymphoma cells) distributed in a mixed cell population. Multicolor immunohistochemistry is thus an important goal, but is challenging to achieve. The prerequisite to quantitative accuracy in a multiple labeled section is lack of interference between the labels. Not only can one label physically block the successful labeling of the next antigen due to steric hindrance, but the various labeling procedures can be chemically incompatible. Suffice it to say that the performance of multiple labelings on a single specimen increases the demands for appropriate controls (43). Assuming that the labeling procedures have been performed satisfactorily, unmixing of 3 or more chromogens is entirely feasible (38,44) (Levenson, submitted). In addition, multiple chromogenic in situ hybridization signals can be combined with IHC (45, 46).

Examples of Spectral Unmixing and Multiplexing

Figure 2:
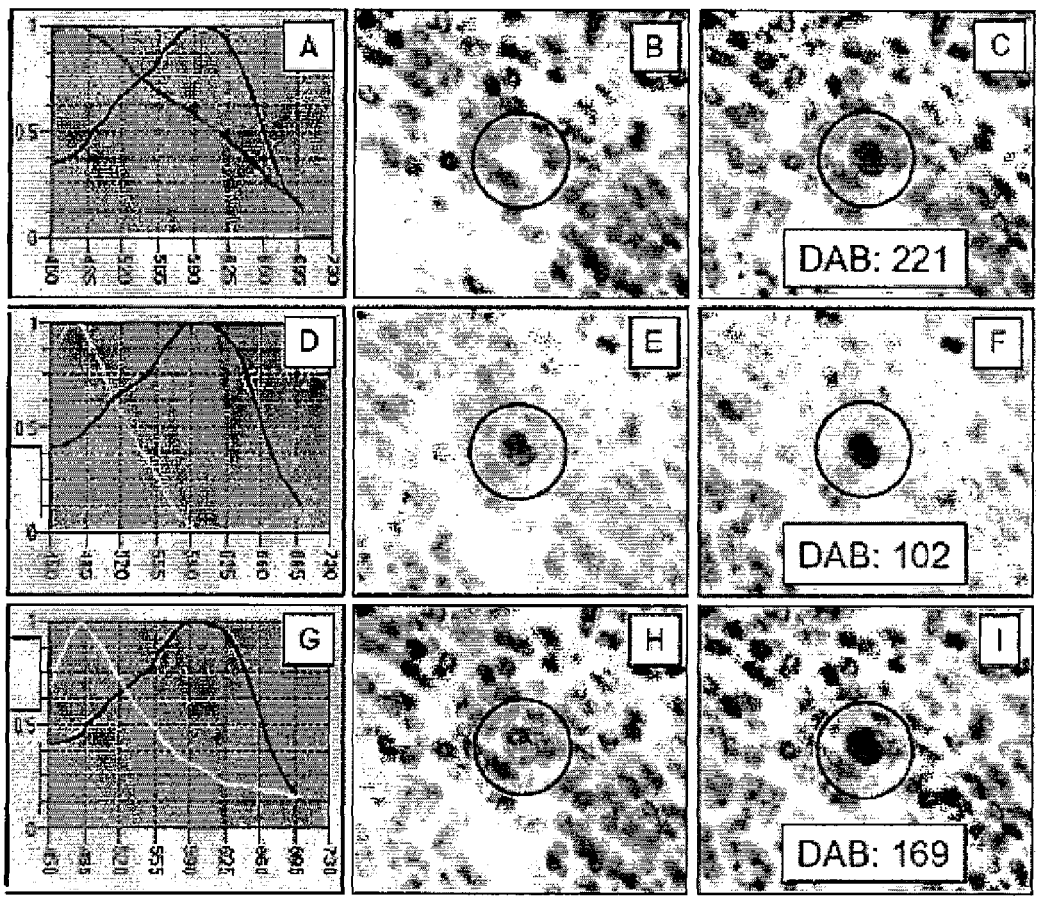
FIG. 2. Unmixing of DAB from hematoxylin: Choice of DAB spectrum affects quantitative results. Differing spectra for the DAB (along with a constant hematoxylin spectrum) are shown in Panels A, D and G, and the respective unmixing results are shown in the corresponding rows. The unmixed hematoxylin channels are shown in the second column (B, E, and H) and the combined DAB plus hematoxylin result is shown in the third column (C, F, and I). The numeric values shown represent the integrated optical density of the DAB signal from the circled nucleus. The third row represents the best DAB spectral estimate, with hematoxylin values for Ki67(+) and (−) nuclei displaying similar intensities. See text for additional discussion.

FIGS. 1 and 2 illustrate the application of spectral imaging to a determination of Ki67 levels in lymph node cells. The Ki67 antigen was visualized using DAB and the sample counterstained with hematoxylin (H). FIG. 1 shows the visual appearance of the sample (Panel A), which, like all the subsequent examples, was spectrally imaged using a Nuance multispectral imaging system. The unmixed DAB and hematoxylin channels are shown in Panels B and C. Note that the hematoxylin staining accurately recapitulates the dense staining of the mantle cells and the paler staining of the germinal center. The small box indicates the detail region highlighted in FIG. 2, which addresses the importance of accurately estimating the "pure" spectrum of the DAB for use in the unmixing procedure. Three different spectra for the DAB component were used as inputs into the unmixing procedure. If one simply captures the spectrum of a DAB-labeled nucleus (top row), unmixes and examines the hematoxylin channel, it can be seen that all of the absorbance (due to DAB plus hematoxylin) ends up in the DAB channel, and a white "hole" is seen in the DAB-positive regions in the H channel. The integrated intensity of the DAB-labeled nucleus is indicated. If one attempts to calculate the "pure" spectrum of the DAB by removing the H component, a variety of curves can be generated, depending on the nature of the algorithm used. The second row shows what happens if overcompensation occurs—in this case, some of the DAB signal remains in the H channel, leading to an overly intense H signal and an underestimation of the DAB intensity. Finally, if the DAB spectrum is correctly estimated, unmixing generates a clean partition of DAB and H signals, in which the H intensity of the labeled nucleus is essentially indistinguishable from that of its neighbors. The integrated intensities of the DAB label in the circled nucleus varied by more than 2-fold depending on the spectra chosen, illustrating the quantitative importance of correct unmixing. Of course, the importance of using appropriate spectra for the unmixing process only increases with the number of chromogens being considered simultaneously.

Figure 3:
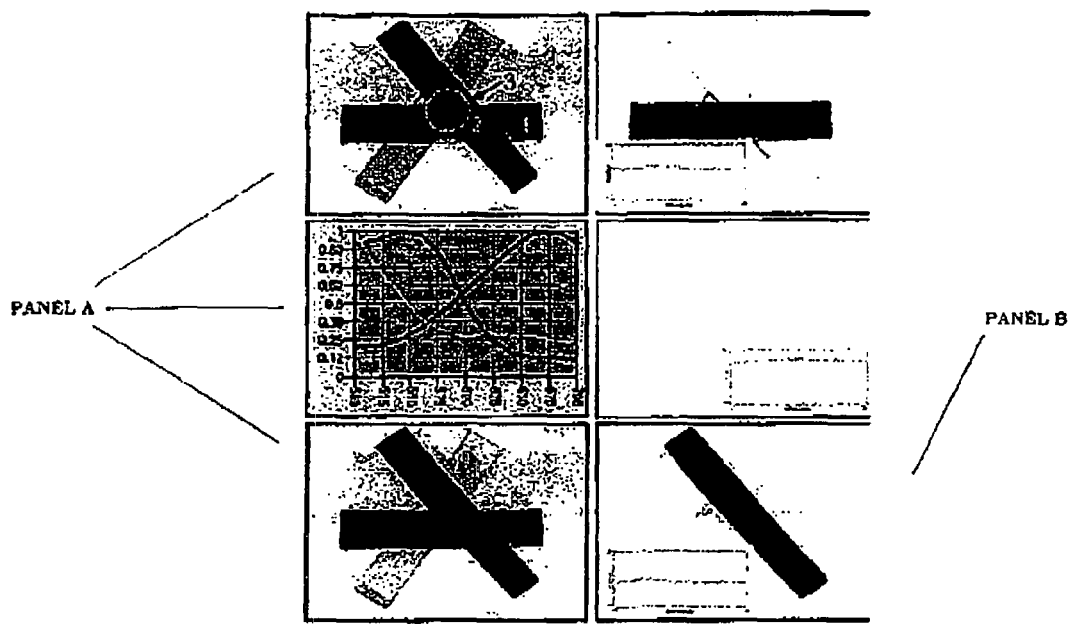
FIG. 3. Three-color unmixing of plastic films with spectra similar to brown and red IHC chromogens and hematoxylin. The strips were arranged so that single, double and triple overlapping regions were present (representative regions are indicate by numbers in Panel A). A spectral data set was acquired; spectra corresponding to the individual plastic strip species are shown in Panel B. Using these spectra, the image cube was unmixed to create individual images of each colored strip by itself (colored in the pseudocolors of the spectral library used for unmixing). Intensity profiles are shown for each strip, indicating that quantitative unmixing could be achieved even when 2 or 3 absorbing species spatially overlapped.

FIG. 3 is intended to demonstrate that 3-color unmixing is feasible, using 3 strips of colored plastic arranged so that all possible combinations of single, double and triple mixtures are captured. The spectra of the individual strips are shown, as are the unmixed images for each strip separately (pseudocolored according to the color of the spectral library curves in Panel B), along with intensity profiles along each strip. As can be seen, calculated absorbance values of each strip are unaffected by the presence of the other absorbers.

Figure 4:
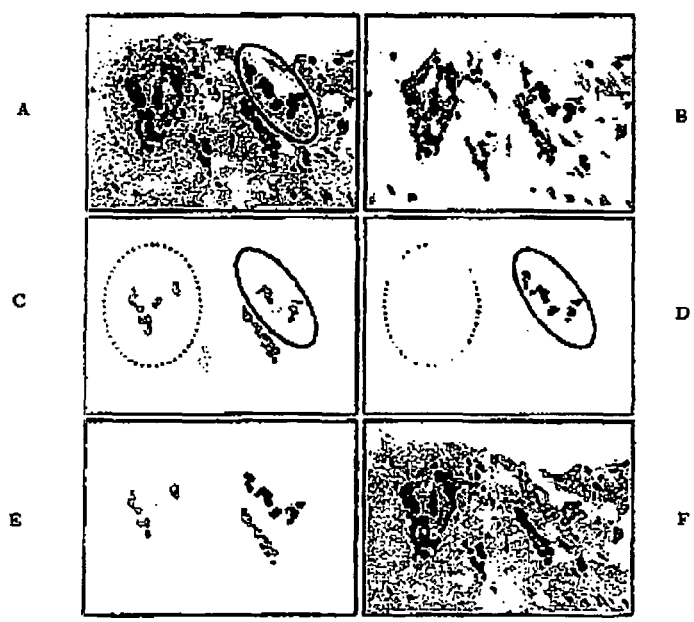
FIG. 4. Detection and unmixing of ER-(DAB) and PR-(Vulcan Red) signals from a breast tissue specimen counterstained with hematoxylin. The 6 panels illustrate the original visual appearance (A), and after unmixing, the H channel (B, which can be used to identify the nuclear compartment for quantitative purposes), and separate channels for ER (C) and PR (D). The dotted oval identifies a region of presumptively normal epithelium, and the solid oval a region of invasive ductal carcinoma. The bottom panels show an overlay of the green and red channels (E), and finally, a depiction of the original image with ER-PR double-positive cells indicated using a yellow mask (F).
Figure 5A:
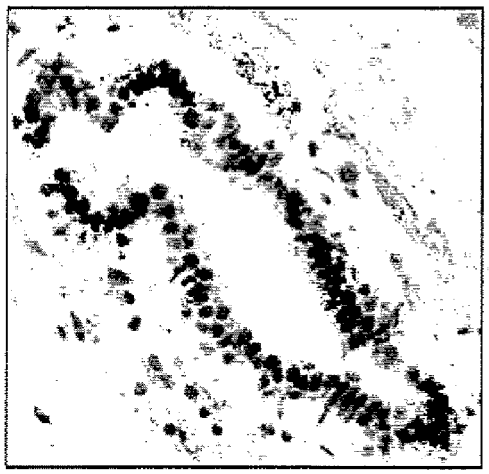
FIG. 5. A. Double IHC stain for ER (DAB-brown) and PR (FAST RED), plus hematoxylin (blue)—cannot be read with naked eye. B. Spectral analysis (unmixing) clearly separates stains; allows comparison and measurement of intensity of peak colors.
Figure 5B:
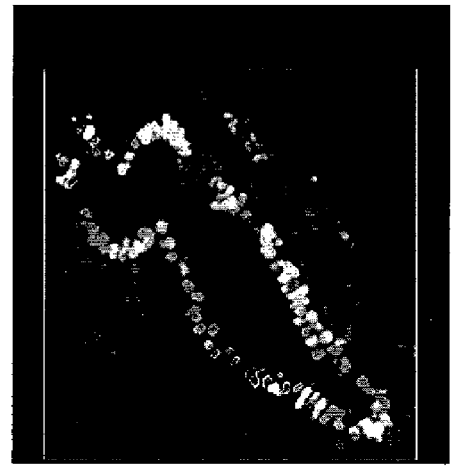
Figure 6:
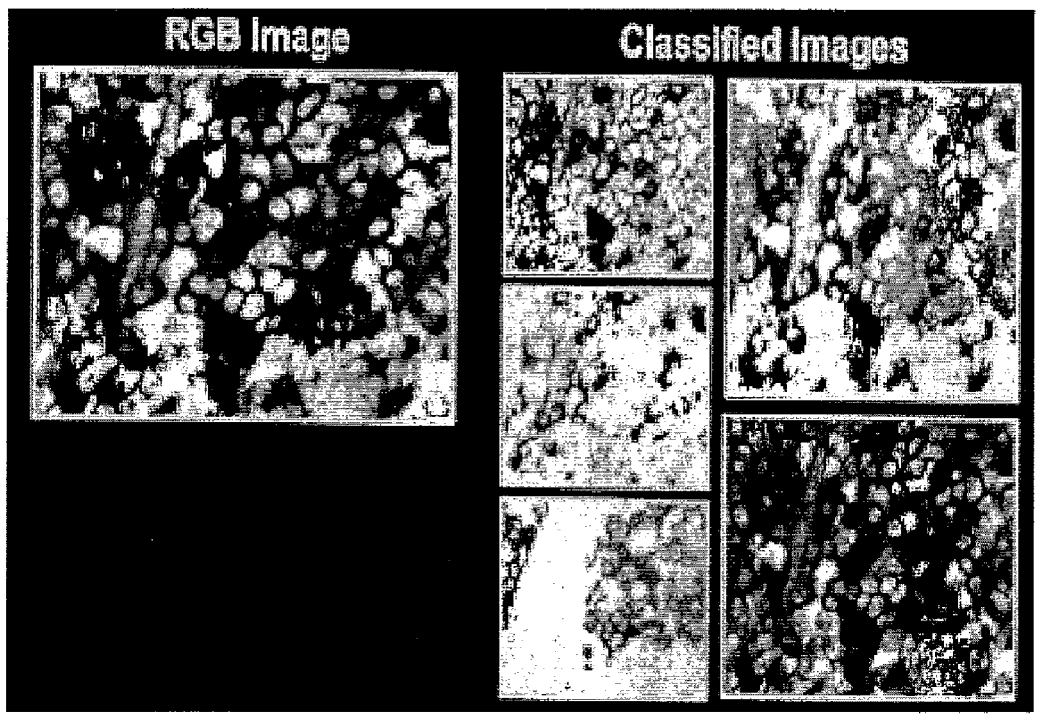
FIG. 6. Triple IHC stain—epithelial cells (brown), Kappa cells (blue), lambda cells (red), showing power of spectral unmixing which allows comparison of intensity of the peak pure colors. By these means test analytes could be measured against a calibrated reference analyte.

Finally, FIG. 4 illustrates the application of unmixing to a histological section of formalin-fixed, paraffin-embedded breast tissue containing both non-malignant and invasive breast epithelial cells, stained for ER and PR, and counterstained with hematoxylin. This example has considerable current relevance because the detection and evaluation of nuclear positivity of breast cancer steroid hormone receptors can affect choice of treatment and is useful in predicting patient outcomes (7,47). Receptor levels are currently evaluated manually, typically using a 0 to 3+ grading system and/or a simple visual estimate of the number of positive nuclei in a relevant cellular population. In this example, ER and PR antigens were visualized with DAB and Vulcan Red chromogens and counterstained with hematoxylin (H). The 6 panels illustrate the original visual appearance, and after unmixing the H channel (which can be used to identify the nuclear compartment for quantitative purposes), and separate channels for ER and PR (green and red, respectively). The dotted oval identifies a region of presumptively normal epithelium, and the solid oval a region of invasive ductal carcinoma. The bottom panels show an overlay of the green and red channels, and finally, a depiction of the original image with ER-PR double-positive cells is indicated using a yellow mask. It is striking that the normal and the malignant regions exhibit different co-localization patterns (normal, ~5%; malignant, ~55%, on a pixel-wise basis).

The biological significance of this and other patterns of markers revealed quantitatively on a per cell basis is currently unknown. What is important is that now there are tools to explore molecular interrelationships in individual cells using multicolor IHC-based techniques, with the potential for quantifiable results, pre-requisites for the beginnings of 'Molecular Morphology' (48).

In conclusion, quantitative immunohistochemistry is not a distant mirage, but is within our grasp. It will require careful attention to the pre-imaging components, including provision of quantitative standards (19) to be included in the entire sample processing pathway, and attention to all parameters of sample acquisition, fixation, and staining, with good QC procedures in place for each probe singly and in combination. For multiplexing, the interaction of one antibody-label combination on all the others must be understood and controlled, and choice of chromogen and counterstains will affect both the visual and quantitative results. Finally, the imaging component has to be carefully performed, with appropriate sensors, exemplified by multispectral, reliable and validated unmixing algorithms. In addition, and not discussed above, it will be essential to incorporate appropriate downstream image analysis and quantification approaches that accurately report molecular events on a per-pixel, per-cell, or per 'relevant tissue component' basis, as appropriate. Ultimately, especially for clinical applications, this task becomes a systems-problem, in which the entire process, from sample acquisition to reporting and interpretation needs to be integrated, standardized (11,19,49), and to the greatest extent possible, automated.

References

1. Horobin R W, Kiernan J A. Editors. Conn's Biological Stains. 10$^{th}$ Edition. Biological Stain Commission, Bios Publishers. Oxford, 2002
2. Becker R L. Standardization and quality control of quantitative microscopy in pathology. J. Cell. Biochem. 1993; 17G: 199-204
3. The Non-Hodgkin's-Lymphoma Classification Project. Clinical Evaluation of the International Lymphoma Group Classification of Non-Hodgkin's Lymphoma. Blood. 1997; 89: 3909-3918
4. Taylor C R. Quality assurance and standardization in immunohistochemistry. A proposal for the annual meeting of the Biological Stain Commission, June, 1991. Biotechnic. Histochem. 1992 (a); 67:110-117
5. Taylor C R, Cote R J. Immunomicroscopy; A Diagnostic Tool for The Surgical Pathologist. 3$^{rd}$ Edition. Elsevier, Edinburgh, 2005
6. Grube D. Constants and variables in immunohistochemistry. Arch. Histol. Cytol. 2004; 67:115-134
7. Diaz L K, Sneige N. Estrogen receptor analysis for breast cancer: current issues and keys to increasing testing accuracy. Adv. Anat. Pathol. 2005; 12(1): 10-9
8. Seidal T, Balaton A J, Battifora H. Interpretation and quantification of immunostains. Am. J. Surg. Patholo. 2001; 25: 1204-1207
9. Umemura S, Itoh H, Serizawa A et al. Immunohistochemical evaluation of hormone receptors in breast cancer: which scoring system is suitable for highly sensitive procedures. Appl. Immunohistochem. Mol. Morph. 2004; 12: 8-13
10. Umemura S, Osamura R Y. Utility of Immunohistochemistry in breast cancer practice. Breast Cancer. 2004; 11: 334-338
11. Leong A S-Y. Quantitation in Immunohistology: Fact or Fiction? A Discussion of Variables That Influence Results. Appl. Immunohistochem. Mol. Morph. 2004; 12:1-7
12. Dapson R W, Feldman A T, Wolfe D. Lessons In Immunohistochemistry. Anatech, Battle Creek, Mich., 2005
13. Nadji M, Nassiri M, Vinceck V et al. Immunohistochemistry of tissue prepared by a molecular friendly fixation and processing system. Appl. Immunohistochem. Mol. Morph. 2006; 115:814-822
14. Shi S R, Cote R J, Young L L, Taylor C R. Antigen retrieval immunohistochemistry: practice and development. J. Histotechnol. 1997; 20: 145-154
15. Shi S R, Cote R J, Chaiwun B et al. Standardization of immunohistochemistry based on antigen retrieval technique for routine formalin-fixed tissue sections. Appl. Immunohistochem. Mol. Morph. 1998; 6: 89-96
16. Shi S R, Gu J, Taylor C R. Antigen Retrieval Techniques: Appl. Immunohistochem. Mol. Morph. Eaton Publishing, Natick, Mass., 2000
17. Taylor C R. Report from the Biological Stain Commission: FDA Issues Final Rule for Classification/Reclassification of Immunochemistry (IHC) Reagents and Kits. Biotechnic. Histochem. 1998; 73:175-177
18. Taylor C R An Exaltation of Experts; concerted efforts in the standardization of Immunohistochemistry. Appl. Immunohistochem. 1993; 1: 232-243
19. Taylor C R. Standardization in immunohistochemistry: the role of antigen retrieval in molecular morphology. Biotechnic. Histochem. 2006 (in press).
20. Sompuram S R, Kodola V, Zhang J et al. A novel quality control slide for quantitative immunohistochemistry testing. J. Histochem. Cytochem. 2002; 50:1425-1433
21. Shi S R, Liu C, Perez J, et al. Protein-embedding technique: a potential approach to standardization of immunohistochemistry. J. Histochem. Cytochem. 2005; 53: 1167-1170
22. Rhodes A, Jasani B, Couturier J, McKinley M J, Morgan J M, Dodson A R, Navabi H, Miller K D, Balaton A J. A formalin-fixed, paraffin-processed cell line standard for quality control of immunohistochemical assay of HER-2/neu expression in breast cancer. Am. J. Clin. Pathol. 2002; 117(1):81-9
23. Shi S R, Cote R J, Liu et al. A modified reduced temperature antigen retrieval protocol effective for use with polyclonal antibody to Cox2 (PG27). Appl. Immunohistochem. Mol. Morph. 2002; 10:368-373
24. Cross S S. Observer accuracy in estimating proportions in images: implications for the semi-quantitative assessment of staining reactions and a proposal for a new system. J. Clin. Pathol. 2001; 54: 385-390
25. Lehr H A, Jacobs T W, Yaziji H et al. Quantitative evaluation of HER-2/neu status in breast cancer by fluorescence in situ hybridization and by immunohistochemistry with image analysis. Am. J. Clin. Pathol. 2001; 115: 814-822
26. Foucar E and Foucar M K. Error in Anatomic Pathology. In Foucar M K. Bone Marrow Pathology. 2nd. Edition. ASCP Press, Chicago, 2000
27. Sirota R L, Error and Error Reduction in Surgical Pathology. Arch. Pathol. Lab. Med. 2005: 129: 1228-1233
28. Rhodes A, Jasani B, Balaton A J, Miller K D. Immunohistochemical demonstration of estrogen and progesterone receptors: correlation of standards achieved on in house tumours with that achieved on external quality assessment material in over 150 laboratories from 26 countries. J. Clin. Pathol. 2000; 53: 292-301
29. Hatanaka Y, Hashizume K, Kamihara Y et al. Quantitative immunohistochemical evaluation of HER2/neu expression with HercepTest™ in breast carcinoma by image analysis. Pathol International. 2001; 51: 33-36
30. Rhodes A, Jasani B, Anderson E et al. Evaluation of Her2/neu immunohistochemical assays sensitivity and scoring on formalin-fixed and paraffin-processed cell lines and breast tumors: a comparative study involving results from laboratories in 21 countries. Am. J. Clin. Pathol. 2002; 118: 408-417
31. Camp R L, Chung G G, Rimm D L. Automated subcellular localization and quantification of protein expression in tissue microarrays. Nat. Med. 2002; 8(11):1323-7
32. Rubin M A, Zerkowski M P, Camp R L et al. Quantitative determination of expression of the prostate cancer protein alpha-methylacyl-CoA racemase using automated quantitative analysis (AQUA): a novel paradigm for automated and continuous biomarker measurements. Am. J. Pathol. 2004; 164(3):831-40
33. Bengtsson E. Computerized Cell Image Analysis: Past, Present, and Future. Image Analysis: 13th Scandinavian Conference, SCIA 2003 Halmstad, Sweden, Jun. 29-Jul. 2, 2003 Proceedings Volume 2749/2003, Lecture Notes in Computer Science Berlin/Heidelberg: Springer 2003; 395-407

34. Bearman G, Levenson R. Biological Imaging Spectroscopy. In: Vo-Dinh T, editor. Biomedical Photonics Handbook. Boca Raton: CRC Press, 2003; 818-26
35. Barber P R, Vojnovic B, Atkin G et al. Applications of cost-effective spectral imaging microscopy in cancer research. J. Phys. D: Appl. Phys. 2003; 36:1729-1738
36. Levenson R M. Spectral imaging perspective on cytomics. Cytometry, Part A. 2006; in press
37. Mansfield J R, Levenson R M. Spectral imaging in biology and medicine: Slices of life. Cytometry, Part A. 2006; in press
38. Zhou R, Hammond E H, Parker D L. A multiple wavelength algorithm in color image analysis and its applications in stain decomposition in microscopy images. Med Phys 1997; 23(12):1977-1986
39. Ruifrok A C, Johnston D A. Quantification of histochemical staining by color deconvolution. Anal. Quant. Cytol. Histol. 2001; 23(4):291-9
40. Farkas D L, Du C, Fisher G W et al. Non-invasive image acquisition and advanced processing in optical bioimaging. Comput Med Imaging Graph 1998; 22(2):89-102
41. Matkowskyj K A, Cox R, Jensen R T et al. Quantitative immunohistochemistry by measuring cumulative signal strength accurately measures receptor number. J. Histochem. Cytochem. 2003; 51(2):205-14
42. Ermert L, Hocke A C, Duncker H R et al. Comparison of different detection methods in quantitative microdensitometry. Am. J. Pathol. 2001; 158(2):407-17
43. Szeszel M K, Crisman C L, Crow L et al. Quantifying estrogen and progesterone receptor expression in breast cancer by digital imaging. J. Histochem. Cytochem. 2005; 53(6):753-62
44. Levenson R, Cronin P J, Pankratov K P. Spectral imaging for brightfield microscopy. Proc SPIE 2003; 4959:27-33
45. Speel E J, Jansen M P, Ramaekers F C et al. A novel triple-color detection procedure for brightfield microscopy, combining in situ hybridization with immunocytochemistry. J. Histochem. Cytochem. 1994; 42(10): 1299-1307
46. Macville M V E, Ried T. Multicolor spectral imaging of chromogenic dyes in cytological specimen. J. Histochem. Cytochem. 1998
47. Press M F, Sauter G, Bernstein L et al. Diagnostic evaluation of HER-2 as a molecular target: an assessment of accuracy and reproducibility of laboratory testing in large, prospective, randomized clinical trials. Clin. Cancer. Res. 2005; 11(18):6598-607
48. Taylor C R. Immunohistochemistry for the age of molecular morphology. Appl. Immunohistochem. Mol. Morph. 2001; 9:1-2
49. O'Leary T J. Standardization in Immunohistochemistry. Appl. Immunohistochem. Mol. Morph. 2001; 9: 3-8

Example II

Quantifiable Internal Reference Standards for Immunohistochemistry; the Measurement of Quantity by Weight Hypothesis Absent uniform sample preparation for formalin paraffin tissues, and absent available tissue reference standards, it is proposed that selected defined analytes (proteins) present intrinsically within tissues may be employed as quantifiable internal reference standards, against which sample quality can be directly assessed and key analytes directly quantified by immunohistochemistry.

Introduction

The poor reproducibility of immunohistochemical (IHC) and molecular methods as applied to formalin fixed paraffin embedded (FFPE) tissue sections, is now recognized as a major impediment to basic research, clinical trials and direct patient care.

In the year 2006, cancer still is diagnosed by the surgical pathologist with his/her microscope using methods that essentially are unchanged over 150 years, from the time that the first histology course was conducted by John Hughes Bennett at Edinburgh, in 1842, and the first major textbook of surgical pathology was drafted by Rudolph Virchow in 1858 (1). That this remains true today, in an era viewed by the public, by politicians and by many scientists, as the era of molecular biology and genetics, is astonishing (2). While several factors contribute, the primary reason for this anachronism is simple. The translation of 'molecular methods' from the bench to 'routine' diagnostic practice in surgical pathology has been greatly hindered by the fact that the usual method of sample preparation for tissue is formalin fixation and paraffin embedment (FFPE). This venerable approach may be satisfactory for the preservation of morphologic detail, but it is certainly not the method of choice for molecular or immunologic assays (including immunohistochemistry—IHC, and in situ hybridization—ISH). The enormous variation in protocols employed for FFPE among different laboratories, or within the same laboratory from specimen to specimen, compounds the problem, and contributes to the current poor reproducibility of these methods.

Over the past two decades many investigators have addressed different aspects of this problem, focusing upon improved sample preparation (fixation), more effective methods of antigen retrieval, and the development of external reference standards or controls. To date, these approaches have failed to produce an overall system of IHC that assures uniform high quality, with a level of reproducibility and reliability, sufficient to allow the possibility of true quantitative analysis.

Some broad conclusions are possible:

for reproducibility of IHC staining techniques overall—current reagents and protocols are probably satisfactory; significant further improvement is dependent upon resolution of the problems of sample preparation, coupled with availability of standard reference materials.

for sample preparation—the scientific aspects of developing a new fixative are challenging and not yet solved; more importantly the logistical and economic obstacles to replacing formalin, worldwide, with something better, even if it became available, are formidable.

for reference standards—the scientific challenges of developing either FFPE cell line blocks, or 'faux' tissues, or protein (or RNA) standards are significant, but again are dwarfed by the logistical and economic obstacles of manufacture, distribution, and inclusion of any external reference material into essentially all FFPE blocks in all laboratories going forward.

Considering the extent of both scientific and economic challenges, the author therefore accepts the following as practical facts:

i. methods of sample preparation of tissues (including fixation) for surgical pathology are unlikely be standardized in the next decade;

ii. universal tissue reference standards will not be available in the foreseeable future;

iii. the scientific and patient care communities will therefore be forced to continue to work with FFPE tissues, in spite of manifold drawbacks;

iv. attempts to standardize IHC on FFPE tissues to a degree that permits quantification are doomed to fail in the absence of reference materials that allow absolute measurement of performance (including reproducibility) of the process as a whole.

These conclusions apply to immunohistochemical (IHC) and in situ hybridization (ISH) methods applied to FFPE tissue sections, and equally to all 'molecular' analyses of proteins, RNA or DNA extracted from FFPE blocks. Even if the problems of sample preparation could be solved, existing archival blocks would still not be addressable for quantitative analysis by any of these methods, and the numerous existing clinical trials that are dependent on data from archival FFPE materials would not be advantaged.

Considering the enormity of the task, Sherlock Holmes would have classified it as "a three pipe problem", where application of the customary methods is of no avail (3). Holmes would have argued as follows: "—when you have eliminated the impossible, whatever remains, however improbable, must be the truth" (4). De Bono (5) may have reached a similar conclusion, again by logic, that when conventional methods have foundered, a radically different approach is necessary. Hence the hypothesis of 'quantifiable internal reference standards' is offered. If we cannot standardize fixation, and if we cannot manufacture a universal FFPE reference material, then the development of a panel of 'quantifiable internal reference standards' for FFPE tissues, 'however improbable' the prospect may seem, should at least be considered. If developed successfully, such a panel would serve to control for the variable effects of sample preparation, and simultaneously would provide a reference base for calibration and quantitative analysis of specific analytes. Like all proper hypotheses, this one is amenable to testing.

Background

"Anatomic pathology changed little in the 100 years preceding 1970. Sequestered in a technologic limbo, it remained relatively untouched by the new methodologies and automated systems that revolutionized the clinical laboratory. The histology laboratory performing only a few simple stains, thereby escaped the rigors of quality assurance in general, and quality control in particular. To dip a slide in hematoxylin for a few minutes, then briefly differentiate it in alcohol, until it looks 'about right' to the technologist and 'makes the pathologist happy' may suffice an H&E stain, but applied to immunohistochemistry it is a recipe for disaster" (6).

More than a decade has passed since these words were put to paper, and at last there are signs that "the times they are a-changin" (7). As ever, necessity may be the mother of invention. The current burgeoning necessity, spawned of a need for clinical accuracy, is that an IHC 'stain' shall provide validated quantifiable results. This necessity is proving to be a potent driver of change, elevating such mundane issues as 'sample preparation' and 'standardization of IHC (and ISH, in situ hybridization) stains' from the status of obscure academic pursuits to real practical problems, demanding of an answer, even warranting requests for proposals for funding from the National Institutes of Health (RFA-CA-07-003. Innovations in Cancer Sample Preparation, U.S. National Cancer Institute, 2006).

Anatomic pathology (surgical pathology, histopathology) is subjective to a degree, based upon pattern recognition and experience (8,9). Quantitative elements often are present, albeit, subliminally, as in gauging the degree of hyperchromatism, or eosinophilia, or even counting mitoses per high power field, but these evaluations are not strictly rule based, not easily reproduced, and they are not quantitative. The usual histopathologic stains [biological stains and aniline dyes, see Conn's Biologic Stains (10)] are qualitative in nature and difficult to perform reproducibly, in terms of intensity of color (stain), from cell to cell and from section to section (different tissues on different days).

Immunohistochemical 'stains' are potentially very different, in that they do contain the inherent elements necessary to provide quantitative data, because each IHC 'stain' is in essence a tissue based 'immunoassay', that is performed in situ on the tissue section. An IHC 'stain' in principle, and in major elements of practice, is identical to an ELISA (enzyme linked immunosorbent assay) test performed in the clinical laboratory, and ELISA based tests are widely recognized as being truly quantitative, if properly performed. Exactly the same reagents that are employed in an ELISA test on serum, for example an assay for insulin, may be employed to perform an IHC stain for insulin in a paraffin section. It is a curious oversight of pathologists, that the principles and reagents used in one environment (serum—ELISA) are universally accepted as providing a strictly quantitative result, but when applied to a tissue section (IHC), constitute only a 'stain', that at best may be employed in some form of semi-quantitative assay, with the intrinsic shortcomings that the term implies.

One object of this invention is to examine the reasons for this conceptual divide. A second goal is to address those aspects of the IHC method that have to date relegated it to the rank of a mere stain, as opposed to a tissue based immunoassay, with a quantitative outcome.

The Immunohistochemical Stain

More then a decade ago the Biologic Stain Commission, in conjunction with the FDA, provided critical leadership in beginning to address the 'standardization' of IHC methods (11,12). Several sponsored conferences focused upon the poor reproducibility of IHC staining methods, prompting a thorough analysis of the possible causal factors. One result was the formulation of the "Total Test Approach", borrowed directly from the rigorous and comprehensive test protocols used in quantitative assays in the clinical laboratory. In the 'Total Test Approach', all aspects of the assay are addressed; pre-analytic, analytic, and post-analytic, including interpreting and reporting of the results (Table 1).

TABLE 1

The Total Test; an IHC (or ISH) stain managed in the same rigorous manner as a clinical laboratory analysis

| Pre-analytic | Test selection |
| --- | --- |
| | Specimen type, acquisition, transport time* |
| | Fixation, type and time* |
| | Processing, temperature* |
| Analytic | Antigen retrieval procedure* |
| | Protocol; control selection |
| | Reagent validation |
| | Technician training/certification |
| | Laboratory certification |
| Post analytic | Control performance |
| | Results |
| | Interpretation/Reporting |
| | Pathologist, experience and CME |

*highly variable elements of in the analytic process Modified from Taylor (11, 13)

While the entire constellation of issues contributing to the performance of an IHC stain was considered (Table 1), the outcome was inevitably somewhat pragmatic, with a focus upon correcting those parts of the process that were most amenable to correction. The quality of reagents was at that time (1992) highly variable, and the validation of reagents by both manufacturers and laboratories left much to be desired. Acting in concert, the BSC and the FDA made recommendations to manufacturers, a number of whom participated in the deliberations. The outcome was an improvement in format and content of package inserts, particularly greater stringency in the claims of manufacturers as to how the their reagents could (and should) be used in diagnostic pathology (11,13).

At about the same time, a second trend was emerging in respect to the practical application of IHC staining, namely the demonstration of prognostic and predictive markers at a cellular level. The availability of numerous new (monoclonal) antibodies facilitated the detection in tissue sections of a variety of molecules that were not directly lineage related, but rather were reflective of the metabolic status of the cell, whether in terms of the phase of cell cycle, or the degree of expression of receptors involved in cell growth. Estrogen receptor (ER) and progesterone receptor (PR) were among the first of these to assume clinical significance, with respect to prognosis and therapeutic response, in this instance in breast cancer (14,15,16). Estimation of Her 2/neu expression by IHC presented similar challenges and soon came to be of paramount importance, with the advent of a therapeutic monoclonal antibody directed against the HER 2 receptor (review, 17). While semi-quantitative IHC studies had been described prior to this time, the shift towards the use of IHC to demonstrate prognostic and 'therapeutic' markers, added real urgency to the need for true quantitative methods. The inherent difficulties are well recognized for ER and PR (18, 19,20), where both methodology and scoring vagaries contribute to error, and where uniform reference standards are not available. The problem is arguably even greater for Her 2 (21,22), where the FDA-approved Dako kit (HercepTest, Dako, Glostrup, Denmark, or Dako USA) does contain a cell line standard and includes instruction about how to read the result. Even with these provisions, scoring of the same cases for HER 2 expression by residents and pathologists shows significant variation, leaving room for improvement.

Towards a Solution

Current approaches to improving the overall quality of IHC staining methods have focused primarily upon sample preparation and quality control or reference standards. The focus of the National Institutes of Health RFA alluded to previously (RFA CA-07-003) is similar: 'enhancement or adaptation of sample preparation methodologies—development of assays to assess sample quality'. This rationale is at first sight sound, in that if these two problem areas are resolved, then developing greater reproducibility of IHC staining should be relatively straightforward. However, it is the view of the author that there is no realistic solution in sight for these key problems.

Sample Preparation

The 'Total Test Approach' served to highlight the importance of specimen acquisition and sample preparation in contributing to the (lack of) quality of the end result of an IHC stain, a deficiency that in turn hampered serious efforts at quantification. In the Clinical Laboratory the response to a specimen that is incorrectly prepared (e.g., in the wrong anticoagulant, or outside of the specified transportation time), is that the specimen (and test) is rejected; not so in surgical pathology, where the general response is to an improperly or poorly fixed specimen is to carry on regardless, seen almost as a challenge to get an acceptable H&E stain, usually without even a notation of a major variance in sample preparation. Where morphologic quality is the only arbiter of 'adequate' processing and handling (for FFPE), the aforementioned response has sufficed for more than a hundred years, but today for IHC and ISH assays, it does not. Now, as IHC methods are being employed in attempts to 'measure' prognostic markers, the traditional cavalier approach to sample preparation (FFPE) has emerged as a critical problem. Today the question is "Exactly how much of the analyte (e.g., ER, HER 2) is present?" Not merely "Is it there, or not there?", as might be sufficient in applying IHC to identify a lineage related marker (e.g. keratin in a putative 'epithelial' cell). The problem reached national attention with the increasing use of IHC findings, as entry criteria for patients into clinical trials (exemplified by staining for Her 2 or CD20, as indicators of possible effectiveness of monoclonal antibody therapy). A NIST (National Institute of Standards) sponsored workshop in Washington (23) cataloged the existing problems, but found no solution at hand.

Sample preparation (including fixation) had been considered by the BSC (as in Table 1), but the problem was deemed complex, without obvious and feasible means of immediate improvement. Over the succeeding decade, 'fixing the fixation problem' was rendered less urgent by the discovery and dissemination of the antigen retrieval (AR) technique (reviews 24,25,26), which had the practical effect that 'useful' IHC staining could be readily achieved by many laboratories for many molecules. Efforts to replace formalin with a new fixative, dubbed by some as more 'molecular friendly' (27), continued, but seemed less urgent. New fixatives, or new formulations of old fixatives, continue to be described, and the prototypic data do indeed suggest that one (or more) of them may be superior to formalin with regard to the capability for subsequent demonstration of tissue analytes (proteins, RNA and DNA) (review, 20). However, even if these claims are granted, and some continue to protest that the fine morphology is 'different', the logistics of converting to a new fixative and new processing method, worldwide, are extremely demanding. History would suggest that if a change did occur, it would occur slowly, randomly, and non-uniformly, and for a time reproducibility would be worse, not better. Also, even if a new fixation and processing method were to be adopted universally, their existence would not enhance access to the huge wealth of data residing in archival FFPE tissues throughout the world, that must form the basis for diagnosis and entry into clinical trials for years to come.

TABLE 2

Summary of desirable characteristics of a 'reference standard' that would provide a basis for accurate quantification of IHC (or ISH) (28)
Immunohistochemical Reference Standard - requirements for calibration of quantitative IHC methods, by analogy with defined standards in clinical laboratories It must be subjected to the same rigors of sample preparation (fixation) as the 'test' tissue.
It must be integrated into all phases of the test (assay) protocol, including evaluation of the result.
It should contain a known amount of the analyte(s) subject to assay.
It should be universally available.
It should be inexhaustible.
It should be inexpensive.

Assay Quality Control—a Reference Standard

The development of a universal external reference standard, sharing the characteristics of calibration standards employed in clinical pathology (Table 2) (28), has encountered difficulties, both scientific and practical. In addition to the commonly employed 'positive control' sections, and tissue micro-arrays (29), different investigators have pursued cell lines or cell line blocks (30), 'faux' tissues or histoids [(2) p 35, FIG. 1-27], and protein 'spots' or deposits (31,32,33). The use of cell lines per se has of course been employed for a FDA approved Her2 'staining test' kit (Dako, HerCept test), with results that are semi-quantitative and, as already noted, may be difficult to reproduce among laboratories and pathologists. With 'faux' tissues or cell line blocks the practical issues of scale up to a commercial level of production and distribution in a form that could incorporated in all stages of sample preparation (FFPE), are at present insurmountable, primarily for economic reasons. The problems of developing purified protein standards, are both similar and different; similar in that the logistics of distributing any reference standard and incorporating the appropriate standard into FFPE blocks routinely (for each different stain) are daunting; different in that the technical challenges to preparing standard protein deposits that will survive FFPE have been explored with limited success (33,34). As currently constituted the usual positive controls, cell lines, or sections, are in reality 'qualitative' controls. They are selected to contain sufficient analyte to produce (usually) intense staining, but exactly how much of the analyte is present in the 'control' is entirely unknown. The best, therefore, that can be achieved is a semi-quantitative result, comparing one section against others, and concluding that staining is more or less intense, or more or less extensive, with the assumption that this relates to the relative amounts of analyte present. This approach fails in significant ways to meet the required characteristics set forth as Table 2, critically, for the purposes of quantification, in lacking data as to the measured amount of the test analyte present in the control.

Lateral Thinking—the Need for a Different and Novel Approach

If sample preparation is unlikely to reach a meaningful level of standardization in the near future (i.e. is presently impossible), and if universal tissue reference standards, meeting the criteria expounded in Table 2, are remote in prospect (i.e. are impossible), what other alternatives are there? Perhaps only those that are 'improbable' [Holmes—(4)], or radically different [De Bono—(5)].

One essential feature of an IHC stain, is that it is performed upon a tissue section that is rich in antigens (proteins, analytes), in addition to the antigen (protein, analyte) under investigation. The question then arises as to whether any one, or more, of these 'background' analytes might be 'universally present' (or nearly so) in diverse cells or tissues, and if so, whether the amount present can be reliably measured, and its survival characterized after fixation and processing (post-FFPE).

Put simply, is it possible to exploit the presence of widely distributed cellular proteins (analytes) to develop a system or panel of 'quantifiable internal reference standards'?

The idea of utilizing 'internal controls' for IHC dates back to the first routine immunperoxidase stains of formalin paraffin tissues (35), exemplified by the use of plasma cell staining in evaluating whether a stain for kappa chain has 'worked', or not [reviewed in 'Immunomicroscopy' (2)]. There is also a precedent in the use of internal controls to assess the extent of overall 'loss of antigenicity' following FFPE, by staining for vimentin, which may be regarded as 'formalin sensitive' and is present in almost all tissue samples (36). The implication is that the degree (intensity) to which vimentin stains, or does not stain, may serve as an indicator ('reporter molecule') of the expected degree of staining of other proteins (analytes). However, these internal controls were used as purely qualitative (not quantitative) controls for sample processing.

Some more recent hint as to the direction that might be taken is gleaned from the work of Dr. R. Singer and colleagues (37), who have commenced a collaboration with our group at USC, with the goal of identifying quantifiable internal standards for FFPE tissues, both proteins and RNA. Singer's group described a method, dubbed RNA peT-FISH (paraffin embedded Tissue) for demonstrating RNA gene expression profiles in individual cells in FFPE sections. The method proved effective on a variety of FFPE tissues, yielding predictive quantitative gene expression signatures. In effect, the method employs ubiquitous house keeping gene RNAs as internal reference standards, that in theory may be developed to provide the basis of a validated quantitative ISH method. By analogy, is it possible to identify equivalent 'house keeping' or structural proteins that are present in relatively constant amounts in specific cell types that enjoy a wide tissue distribution? Given that such analytes and cells could be identified in all (almost all) tissue sections, they could provide the basis for an internal control system as described below.

Quantifiable Internal Reference Standards for IHC—a Proposed System of Use

For an internal reference standard to be effective it should ideally be demonstrated in the same FFPE section, alongside the antigen under study (test analyte). It is proposed that every IHC stain (read—'assay'), for which the goal is a quantifiable result, should be in the form of standardized controlled 'double IHC stain reaction', including a 'stain' for the unknown 'test' analyte, and a second 'stain' for an internal reference analyte. The amount present of the unknown 'test' analyte (protein) might then be measured with some accuracy (degree thereof to be established) by comparison of the intensity of IHC staining of the 'test' analyte with the intensity of staining of the reference analyte, using validated quantitative IHC protocols and computer assisted image analysis, as by comparative quantitative spectral imaging (28).

Admittedly this approach requires a 'leap of faith'; several leaps, and quite big ones at that. But what is there to lose? None of the proposed external standards discussed previously come close to meeting the requirements set forth in Table 2 (28), and conventional positive control sections fall well short. Even a modest improvement upon the current mode of practice would be worthwhile.

Some assumptions are necessary, but these are amenable to testing. It is proposed to proceed as follows. One or more candidate reference analytes must be selected on the basis of its presence in relatively constant amounts in specific cell types that are easily recognized and widely distributed (such as endothelial cells or lymphocytes). This predicate is easily tested. In establishing a standard, the absolute amount of the candidate reference analyte in fresh tissue must be determined by experiment using independent methods, for example, on a per cell basis. It will then be necessary to establish the extent to which the reference analyte(s) is preserved following FFPE with optimized antigen retrieval. These data will again be derived experimentally and may be expressed as a 'fixation coefficient' (FxC), encoding the relationship of the absolute amount of analyte (antigen) present in the fresh tissue (cell) and the intensity of the corresponding IHC signal, with the amount of analyte present in the FFPE tissue and the intensity of its IHC signal, by identical IHC protocols. Similar data will be collected, again by experiment, for various test analytes for which a quantitative result is required (e.g., ER, Her2), relating the experimentally derived 'fixation coefficient' for each potential test analyte with that established for one or more reference analytes, that show similar behavior when subject to FFPE. With such data in hand, measurement of the reference analyte IHC signal and the test analyte IHC signal on a double stained slide would allow a more accurate calculation of the amount present (e.g., on a per cell basis) than is achievable by current 'semi-quantitative' scoring methods.

This approach also exploits the idea that the adverse effects of different FFPE methods during sample preparation may be minimized by the use of an optimized-AR protocol, resulting in improved reproducibility of IHC staining, presumably reflective of some consistency in recovery of antigen. This strategy was pioneered by our group (38), and has been proven effective for qualitative IHC studies among different laboratories. It offers the possibility that for one of more candidate reference analytes the 'fixation coefficient' may show acceptable consistency across the usual variations encountered in formalin fixation and paraffin embedment. A perfect answer is not expected, merely something better than the 'uncontrolled controls' available to us today. Ultimately it should be possible to provide a reliable measurement (by calculation) of the amount of unknown test analyte present in the cells/tissue prior to the initiation of sample preparation (i.e., when it was removed from the patient).

While absolute accuracy is not envisaged, it is at least possible that results can be achieved that are superior to current semi-quantitative IHC measurements, that make little attempt to control for vagaries in sample preparation, and lack any objective (quantifiable) reference standard whatsoever. Once a 'quantifiable internal reference standard' is established in a cell adjacent to another cell containing the 'test' analyte within an FFPE section, then other confounding issues, such as variation in section thickness, or the exact plane of transection of individual cells, can be addressed, in the manner of 'background noise', by computer assisted image analysis systems.

While the above argument may constitute a 'leap of faith' for establishing protein based standards, encouragement may be drawn from the application of a similar rationale to the development of internal RNA reference standards, in the design of the peT-FISH method for FFPE tissues, using house keeping gene RNAs as internal reference standards, as already described (37). Also there is the analogy of the standardized RT-PCR (StaRT PCR) method, which can be rendered quantitative by the use of internal actin RNA (widely distributed in different cells) as the reference control (39). We have successfully employed this approach in our laboratories to quantify transcripts in bladder cancer cell lines and tumor tissues, and demonstrated its superior reproducibility and consistency in relation to real time PCR (40).

"Immunohistoalchemy"—a Place for the Alchemist

Alchemy—the 'art' of transmuting base metals into gold. Transmutation of an IHC 'Stain' to an IHC 'Analysis'

The availability of effective, reliable, quantitative IHC and ISH methods would allow visualization and ultra-cellular localization of key analytes, important to the diagnosis and prognosis of cancer, in conjunction with traditional surgical morphology criteria used for cell recognition and diagnosis. The potential offered by this combined dual capability is becoming known as Molecular Morphology. It is the raison d'etre of this journal, Applied Immunohistochemistry and Molecular Morphology, and in rudimentary form is the basis of 80% or more of scientific papers published today in diagnostic surgical pathology. Few would argue against the notion that surgical pathology (particularly cancer diagnosis) has been transformed by the advent of IHC methods. Rendering the method both reproducible and quantitative would mean that both IHC and ISH 'stains' would function not just stains, but as tissue based assays, to be managed with the same rigor as any other immune based quantitative assay in the laboratory. It would mean that the future has arrived; pathology would never be the same again.

Transmutation of Base Pathologists into Gold

Ultimately it would be possible reliably to measure RNA and protein, the end products of gene action, in situ within individual cells, leading to new criteria for cancer diagnosis and prognosis. In research the significance is profound, in that evaluation of gene activity, by the quantifiable demonstration of RNA expression and protein production, would allow scientists (read—pathologists) to gain information at the molecular level regarding the functioning of genes, not just their presence. The combination of these capabilities, for localization and quantification at a sub-cellular level, will open new fields of study, with regard to the pathogenesis of disease in general, and cancer in particular. If successful, it will provide the basis for establishing Quantitative Molecular Morphology (the combination of quantitative molecular and morphologic criteria) as the method for cancer diagnosis, prognosis and therapy selection. More important than any of these potential gains, is the possibility that the development of these methods will change the mindset of pathologists, from dealing simply with stains and patterns, to a modality that allows for the performance of direct quantitative assays on individual cells in tissue sections. If in the fullness of time it transpires that pathologists come to regard IHC (and ISH) methods not simply as stains, but as cell based quantitative assays, then we will have achieved more than transforming the concept of the stain, we will have accomplished the transmutation of the pathologists themselves.

References (1) Rudolph Virchow. Die Cellularpathologie. Verlag von August Hirschwald, Berlin, 1858.
(2) Taylor C R and Cote R J. Immunomicroscopy; A Diagnostic Tool for The Surgical Pathologist. $3^{rd}$ edition. Elsevier, Edinburgh. 2005.
(3) Doyle Sir Arthur Conan. Sherlock Holmes, in the "Redheaded League". Ed. H Greenhough Smith. Newnes, London. Strand Magazine. August: 1891.
(4) Doyle Sir Arthur Conan. Sherlock Holmes, in the "Sign of Four. Spencer Blackett, London (also in Lipincott's Magazine, same year). 1890.
(5) De Bono, Edward. Lateral Thinking. Pelican Books. London. 1970.
(6) Taylor C R. An Exaltation of experts: concerted efforts in the standardization of immunohistochemistry. Appl Immunohistochem 1993; 1:232-243.
(7) Dylan Bob (Zimmerman, Robert Allen). The Times They Are A-changin'. Columbia Studios, New York. 1964.
(8) Hensen D E. Studies in observer variation. Arch Pathol Lab Med. 1991; 115, 991-992.
(9) Foucar E and Foucar M K. Error in Anatomic Pathology. In Foucar M K. Bone Marrow Pathology. 2nd Edition. ASCP Press, Chicago, 2000.
(10) Horobin R W and Kiernan J Editors. Conn's Biological Stains. $10^{th}$ edition. Biological Stain Commission, Bios publishers. Oxford. 2002.
(11) Taylor C R. Quality assurance and standardization in the immunohistochemistry. A proposal for the annual meeting of the Biological Stain Commission, June 1991. Biotech Histotech. 1992; 67:110-117.
(12) Taylor C R. Report from the Biological Stain Commission: FDA Issues Final Rule for Classification/Reclassification of Immunochemistry (IHC) Reagents and Kits. Biotechnic & Histochem. 1998; 73:175-177.
(13) Taylor C R. Standardization in immunohistochemistry: the role of antigen retrieval in molecular morphology. Biotechnics and Histochemistry. 2006 (in press).
(14) Henry J A, McCarthy A L, Angus B et al. Prognostic significance of Estrogen Regulated Protein, Cathepsin D, in Breast Cancer. Cancer. 1990; 65: 265-271.

(15) Elias J M, Cartun R A, England D M, et al. Interlaboratory Comparison of Estrogen Receptor Analysis in Paraffin Sectitons by a Monoclonal Antibody to Estrophilin (H222). J Histochnol. 1993, 16: 57-63.
(16) Battifora H, Mehta P, Ahn C. Oestrogen receptor immunohistochemical assay in paraffin-embedded tissue: a better gold standard? Appl Immunohistochem. 1993; 1: 39-45.
(17) Piccart M, Lorisch c, Di Leo A et al. The predictive value of HER 2 in breast cancer. Oncology. 2001; 61 (suppl. 2):73-82.
(18) Rhodes A, Jasani B, Balaton A J, Miller K D. Immunohistochemical demonstration of estrogen and progesterone receptors: correlation of standards achieved on in house tumours with that achieved on external quality assessment material in over 150 laboratories from 26 countries. J Clin Pathol. 2000; 53: 292-301.
(19) O'Leary, T. J. Standardization in immunohistochemistry. Appl Immunohistochem. Mol. Morph. 2001; 9: 3-8.
(20) Leong A S-Y. Quantitation in Immunohistology: Fact or Fiction? A Discussion of Variables That Influence Results. Appl Immunohist Mol Morph. 2004; 12:1-7.
(21) Rhodes A, Jasani B, Anderson E et al. Evaluation of Her2/neu immunohistochemical assays sensitivity and scoring on formalin-fixed and paraffin-processed cell lines and breast tumors: a comparative study involving results from laboratories in 21 countries. Am J Clin Pathol. 2002; 118: 408-417.
(22) Bilous M, Dowsett M, Hanna W. et al. Current perspectives on HER 2 testing: A review of national testing guidelines. Mod Pathol. 2003; 16: 173-182.
(23) Hammond M E H, Barker P, Taube S et al. Standard Reference Material for Her2 Testing: Report of a National Institute of Standards and Technology-Sponsored Consensus Workshop. Appl Immunohist Mol Morph. 2003; 11: 103-106.
(24) Shi S R, Cote R J, Taylor C R. Antigen Retrieval Immunohistochemistry: Past, Present and Future. J Histochem Cytochem 45:327-343, 1997.
(25) Shi S R, Gu J, Taylor C R. Antigen Retrieval Techniques: Immunohistochemistry and Molecular Morphology. Eaton Publishing, Natick, Mass. 2000.
(26) Shi S-R, Cote R J, and Taylor C R. Antigen Retrieval Immunohistochemistry and Molecular Morphology in the Year 2001. Appl Immunohist Mol Morph. 2001; 9:107-116.
(27) Nadji M, Nassiri M, Vinceck V et al. Immunohistochemistry of tissue prepared by a molecular friendly fixation and processing system. Appl Immunohistochem Mol Morph. 2005: 13: 277-283.
(28) Taylor C. R. and Levensen R. M. Quantification of immunohistochemistry—issues around methods, utility and semi-quantitative assessment. Histopathology. 2006 (in press).
(29) Zu, Y., Steinberg, S. M., Campo, E., Hans, C. P., Weisenburger, D. D., Braziel, R. M., Delabie, J., Gascoyne, R. D., Muller-Hermlink, K., Pittaluga, S., Raffeld, M., Chan, W. C., and Jaffe, E. S. Validation of tissue microarray immunohistochemistry staining and interpretation in diffuse large B-cell lymphoma, Leukemia & Lymphoma. 2005: 46: 693-701.
(30) Riera, J., Simpson, J. F., Tamayo, R., and Battifora, H. Use of cultured cells as a control for quantitative immunocytochemical analysis of estrogen receptor in breast cancer. The Quicgel method, Am. J. Clin. Pathol. 1999; 111: 329-335.
(31) Sompuram, S. R., Kodela, V., Zhang, K., Ramanathan, H., Radcliffe, G., Falb, P., and Bogen, S. A. A novel quality control slide for quantitative immunohistochemistry testing, Journal of Histochemistry & Cytochemistry. 2002; 50: 1425-1434.
(32) Sompuram, S. R., Kodela, V., Ramanathan, H., Wescott, C., Radcliffe, G., and Bogen, S. A. Synthetic peptides identified from phage-displayed combinatorial libraries as immunodiagnostic assay surrogate quality-control targets. Clinical Chemistry. 2002; 48: 410-420.
(33) Shi, S.-R., Liu, C., Perez, J., and Taylor, C. R. Protein-Embedding Technique: A Potential Approach to Standardization of Immunohistochemistry for Formalin-Fixed, Paraffin-Embedded Tissue Sections, J. Histochem. Cytochem. 2005; 53: 1167-1170.
(34) Shi, S.-R., Liu, C., Balgley, B. M., Lee, C., and Taylor, C. R. Protein extraction from formalin-fixed, paraffin-embedded tissue sections: quality evaluation by mass spectrometry, J. Histochem. Cytochem. JHC express. 2006; DOI: 10.1369/jhc.5B6851.
(35) Taylor, C. R. and Burns, J. The demonstration of plasma cells and other immunoglobulin containing cells in formalin-fixed, paraffin-embedded tissues using peroxidase labeled antibody, J Clin Pathol. 1974; 27: 14-20.
(36) Battifora, H. Assessment of antigen damage in immunohistochemistry. The vimentin internal control, American Journal of Clinical Pathology. 1991; 96: 669-671.
(37) Capodieci, P., Donovan, M., Buchinsky, H., Jeffers, Y., Cordon-Cardo, C., W., G., J., E., M., S. S., and Singer, R. H. Gene expression profiling in single cells within tissue. Nature Methods. 2005; 2: 663-665.
(38) Shi, S. R., Cote, R. J., Yang, C., Chen, C., Xu, H. J., Benedict, W. F., and Taylor, C. R. Development of an optimal protocol for antigen retrieval: a 'test battery' approach exemplified with reference to the staining of retinoblastoma protein (pRB) in formalin fixed paraffin sections, J Pathol. 1996; 179: 347-52.
(39) Willey, J. C., Crawford, E. L., Jackson, C. M., Weaver, D. A., Hoban, J. C., Khuder, S. A., and DeMuth, J. P. Expression measurement of many genes simultaneously by quantitative RT-PCR using standardized mixtures of competitive templates, Amer. J. Respiratory Cell Mol. Biol. 1998; 19: 16-24.
(40) Pagliarulo, V., George, B., Beil, S. J., Groshen, S., Laird, P. W., Cai, J., Willey, J., Cote, R. J., and Datar, R. H. Sensitivity and reproducibility of standardized-competitive RT-PCR for transcript quantification and its comparison with real time RT-PCR, Mol. Cancer. 2004; 3: 5.

Example III

IHC/ISH in Archival Tissues: Quantifiable Internal Reference Standards

"Development of Quantifiable Internal Reference Standards (QIRS) in Normal and Pathologic Tissues for Control of Sample Preparation and Calibration of Immunohistochemical and In Situ Hybridization Assays (Stains) in Formalin Fixed Paraffin Embedded Tissues".

Specific Aims
Hypothesis:
Absent improved and uniform sample preparation for formalin paraffin (FFPE) tissues, and absent available tissue reference standards, we present the hypothesis that analytes (proteins and RNAs) present intrinsically within tissues may be employed as 'Quantifiable Internal Reference Standards', against which sample quality can be directly assessed and key analytes can be directly quantified[94].

Novel Features:

1. A panel of Quantifiable Internal Reference Standards (QIRS) will be assembled based upon the accurate measurement of proteins (and RNAs) present in consistent amounts in common identifiable cells. A primary goal of this research is to demonstrate feasibility in establishing this panel.

2. Because the Quantifiable Internal Reference Standards (QIRS) are an intrinsic part of the tissue, they will have undergone identical sample preparation and IHC protocols to the test analyte, and thus will serve both to validate sample preparation and also to calibrate the IHC stain, in effect converting it to an immunoassay for quantification.

3. Quantification of RNA transcripts in FFPE will be based on comparison to Quantifiable Internal Reference Standards (QIRS), and will be reproducible from tissue to tissue, despite differences in fixation. The highly variable degradation of RNA in sample preparation will be will be evaluated by using internal standards intrinsic to the StaRT PCR method. This is in contrast to other methods of RNA analysis, which have focused on improved methods of extraction from FFPE, but do not measure degradation.

4. All IHC immunoassays (stains for protein), for which the goal is a quantifiable result, will be in the form of 'double IHC stain reactions', including a 'stain' (IHC immunoassay) for a Quantifiable Internal Reference Standard (protein), and a second 'stain' (immunoassay) for the unknown 'test' analyte.

5. The amount present of the unknown 'test' analyte (protein) may then be measured with accuracy (degree thereof to be established) by comparison of the intensity of stain of the 'test' analyte with the intensity of stain of the Reference Standard, using validated quantitative IHC protocols and existing image analysis equipment and software.

6. Having previously established the extent to which the reference standard(s) is preserved following FFPE, then a 'correction factor' (Aim 5) and a 'relative loss factor' (R33 Aim 1) can be applied to provide a quantitative measurement of the amount of unknown test analyte present in the tissue prior to sample preparation (i.e., when it was removed from the patient).

A parallel rationale and method is proposed to develop quantitative ISH assays (stains) for RNA.

Part I

The lack of reproducibility of immunohistochemical (and molecular) methods as applied to formalin fixed paraffin embedded (FFPE) tissue sections, or extracts thereof, constitutes a major obstacle to basic research, clinical trials and direct patient care. RFA CA-07-003/015 is a constructive response by the NCI to this problem, by recognizing that non-uniform sample preparation is a major contributing factor—'the development of assays to assess sample quality, and studies designed to elucidate the criteria by which to judge sample quality.'

Our earlier work in this area[1] has led us to conclude, based on scientific and economic considerations, that i. methods of sample preparation of tissues (including fixation) for surgical pathology will not be standardized in the next decade;

ii. universal external tissue reference standards also will not be available in the foreseeable future; and iii. the scientific and patient care communities will therefore be forced to continue to work with FFPE tissues, in spite of manifold drawbacks.

These conclusions apply to immunohistochemical (IHC) and in situ hybridization (ISH) methods applied to FFPE tissue sections, and to all analyses of proteins, RNA or DNA extracted from FFPE blocks. Furthermore, even if these problems could be solved, existing archival blocks would still not be addressable for quantitative analysis, and the numerous existing clinical trials (current and planned) that are dependent on data from archival FFPE materials would not be advantaged.

A completely different and entirely novel approach, that requires neither standardized fixation nor external reference materials, is therefore necessary to allow for quantitative assays on FFPE tissues. It is proposed to accomplish this goal by establishing Quantifiable Internal Reference Standards in FFPE tissues, thereby serving two purposes simultaneously: (i) to control for the effects of variable sample preparation, and (ii) to provide the reference base for calibration and quantitative analysis of specific analytes.

The overall goal is to establish the initial feasibility of this approach for both proteins and RNA molecules using FFPE cell line block preparations (R21), following which the lessons learned will adapted to the development of Quantifiable Internal Reference Standards in normal and pathologic human tissues (R33). If successful the end result will be the conversion of the established qualitative IHC 'tissue stain' into a quantifiable tissue based immunoassay, just like ELISA. Similarly existing qualitative ISH and FSH stains will be rendered quantitative.

The Specific Aims are as follows:

Specific Aim 1—to select 2 analytes (each, for proteins and RNAs) as candidates for Quantifiable Internal Reference Standards, that are expected to be present at relatively constant concentrations within cell types that are common to (almost) all tissues, and to demonstrate that these proteins and RNAs are present during the steps of sample preparation (fixation/processing) in a consistent/predictable manner. FFPE blocks prepared from cell lines (Table 4) will be used as the model in this phase. Aim 1 will employ basic qualitative IHC and ISH to demonstrate presence of the analyte—exactly how much of each analyte can be detected before and after FFPE is the object of Aims 2, 3 and 4.

Specific Aim 2—to make extracts from the cell line blocks at different steps of sample preparation and measure accurately the amount per cell of (a) each selected protein using standard ELISA methods, and (b) each selected mRNA using a standardized competitive RT-PCR (quantitative StaRT-PCR).

Specific Aim 3—to construct quantitative IHC methods, using the same antibody reagents as in the ELISA assays, and to validate IHC derived measurements of protein per cell by comparison to the ELISA data at each stage of sample preparation (Aim 2). This aim includes testing the IHC method for consistent generation of label (chromogen), to allow for strict quantification in cell block sections by image analysis methods.

Specific Aim 4—to test the quantitative peT-FISH RNA method developed by the consortium collaborator, Dr. Robert Singer for reproducibility at the different steps of FFPE, with respect to quantification of selected RNA per cell with validation in comparison to Start PCR data (Aim 2).

Specific Aim 5—to determine whether the candidate protein and RNA analytes, once identified and quantified, show consistency in behavior when tested by quantitative IHC and ISH following FFPE in different cell line blocks, as would be required of a candidate tissue internal reference standard (i.e., is the loss/recovery of each candidate analyte consistent to a useful degree across different FFPE blocks).

Specific Aim 6—to extend the range of protein and RNA analytes studied (under Aims 1-4) in order to construct a panel of 3 protein analytes (ideally one each of cytoplasmic, cell surface and nuclear proteins) and 3 RNA analytes as candidate internal reference standards in the FFPE cell line blocks.

These prototypic 'internal reference' panels, validated on FFPE cell line blocks, will then be subjected to further testing and expansion in the phase 33 study, with application to normal and pathologic human FFPE tissues.

Background and Significance

For reasons described herein, it is our belief that methods of sample preparation of tissues (including fixation) for surgical pathology will not be significantly improved (or standardized) in the next decade, and universal reference materials will not be available in the foreseeable future.

We therefore propose an entirely novel approach, that utilizes FFPE tissues and does not require external reference materials, namely establishing Quantifiable Internal Reference Standards to address the major problem of non-reproducibility of IHC, ISH methods and to render them quantifiable.

From our ongoing experience of applying immunohistochemistry (IHC) and molecular methods to formalin fixed paraffin embedded (FFPE) tissues over 30 years[1-7], and our development of the Antigen Retrieval (AR) method over 15 years[8-13], we believe that the impediments to achievement of reproducible IHC and ISH methods, that can yield quantitative results, fall into three areas:

1. lack of standardization of sample preparation (FFPE) within and across different laboratories, with variable and unknown degradation of both protein and RNA, 2. lack of reproducibility of AR, IHC and ISH methods within and across different laboratories, 3. failure to identify and establish universal reference materials (standards) for the major classes of analytes that would permit calibration of the analytical method and quantification of the analyte.

These three problems clearly are interconnected. It is now generally accepted that attempts to standardize either, (1) methods of sample preparation, or (2) IHC/ISH staining protocols, are doomed to fail in the absence of widely available standard reference materials (3), that would allow absolute measurement of performance (including reproducibility) of the process as a whole.

Current approaches to improving the overall quality of IHC (and ISH) staining methods revolve around solving one or more of the three problems described above. RFA CA-07-015 addresses in particular problems 1 and 3—'enhancement or adaptation of sample preparation methodologies—development of assays to assess sample quality'.

The rationale is sound, in that if these two problem areas (sample preparation and reference standards) are resolved then the solution to problem #2 should be relatively straightforward. However, we have concluded that there is no practically applicable solution in sight for these key problems.

Our work in this area, over many years, including our existing IMAT R33 award (Retrieval of DNA, RNA and Protein from Archival Tissues), has followed the conventional approaches outlined above. Significant advances have resulted from these efforts, including the first application of IHC to routine FFPE by the PI[2], the development of Antigen retrieval (AR) methods for IHC by another of our group[8], and the adaptation of AR for extracting proteins, RNA and DNA[14, 15]. However, we are forced to recognize that these conventional approaches, to improved sample preparation, antigen retrieval and reference standards, have failed to produce an overall system of IHC that assures quantitative results of uniform high quality, with reproducibility and reliability.

We have therefore concluded:

1. for sample preparation—that the scientific issues of developing a new fixative are challenging and not yet solved; more importantly the logistical and economic obstacles to replacing formalin, worldwide, with something better are formidable, such that there will not be an improved widely used sample preparation (fixation) procedure in the next decade.

2. for reproducibility of AR and IHC protocols—that current reagents and protocols are probably satisfactory, but further progress is dependent upon resolution to the problems of sample preparation and standard reference materials.

3. for reference standards—that the scientific issues of developing either FFPE 'faux' tissues or protein or RNA standards are significant, but again are dwarfed by the logistical and economic obstacles of manufacture, distribution and inclusion of any external reference standard into essentially all FFPE blocks going forward. Reference standards for IHC or ISH on FFPE tissues will thus not become widely available in the foreseeable future.

These conclusions apply both to IHC and ISH on tissue sections and to all analyses of proteins, RNA or DNA extracted from FFPE blocks. Even if these problems could be solved, existing archival blocks would still not be addressable for quantitative analysis by any of these methods, and the numerous existing clinical trials that are dependent on data from archival FFPE materials would not be advantaged.

The focus of this new proposal is therefore radically different. It accepts the following as practical facts:
that we are going to be working with FFPE tissues for years to come,
that a universally available external reference standard for most IHC and ISH analytes will not become available the foreseeable.

The proposal emphasizes IHC methods, because IHC methods are currently widely used, and problematic in surgical pathology. However, ISH methods (for RNA or DNA) are included in parallel with the belief that ISH would also be widely used in if attendant problems of reproducibility and quantification could be resolved. Thus, while gene expression profiling has shown great promise in diagnosis, prognosis and therapy selection, the great impediment has been variable and unknown RNA degradation if FFPE tissues and extracts thereof, a problem that we plan to address using StaRT PCR, which because it includes internal standards can measure these effects, unlike other existing RT PCR methods.

Changing the Mindset from an IHC 'Stain' to an IHC 'Analysis'

More then a decade ago the Biologic Stain Commission, in conjunction with the FDA, provided critical leadership in addressing the 'standardization' of IHC[1, 16, 17], Several conferences led to greatly improved standards for reagent validation package inserts[17-28]. One contribution from our group was the recognition that an IHC stain could be more than just a simple stain; it should be viewed as an 'in situ' immunoassay in the tissue section environment, and should be managed in a manner identical to any other laboratory analysis. This led in turn to the formulation of the "Total Test Approach"[29, 30], borrowed directly from the rigorous and comprehensive test protocols used in quantitative assays in the clinical laboratory. In the 'Total Test Approach', all aspects of the assay are addressed; pre-analytic, analytic, and post-analytic, including interpreting and reporting of the results (Table 1), reviewed by the PI in Immunomicroscopy, A Diagnostic Tool for Surgical Pathologists[1].

TABLE 1

The Total Test: an IHC (or ISH) stain managed in the same rigorous manner as a clinical laboratory analysis

| Pre-analytic | Analytic | Post analytic |
|---|---|---|
| Test selection | Antigen retrieval procedure* | Control performance |
| Specimen type, acquisition, transport time* | Protocol; control selection | Results |
| Fixation, type and time* | Reagent validation | Interpretation/Reporting |
| Processing, temperature* | Technician training/certification | Pathologist, experience and CME |
| | Laboratory certification | |

*Highly variable elements of 'sample preparation'.

Sample Preparation

One result of adopting the 'Total Test Approach' was to highlight the importance of specimen acquisition and sample preparation in contributing to the (lack of) quality of the end result of an IHC stain. In the Clinical Lab the response to a specimen that is incorrectly prepared (e.g., in the wrong anticoagulant, or outside of the specified transportation time), is that the test is rejected; not so in surgical pathology, where the general response is to embed the tissue and perform the stain, usually without even a notation of major variance in sample preparation. Where morphologic quality is the only arbiter of 'adequate' processing and handling (FFPE), the aforementioned response has sufficed for more than a hundred years, but today for IHC and ISH assays, it does not. This shortcoming has been recognized, albeit at subliminal level, for some time, with regard to the lack of reproducibility of the usual qualitative IHC, but little has been done about it, apart from recommendations from the BSC, CLSI (formerly NCCLS), UK-NEQAS and others[1, 17-19, 29-33]. Now, however, as IHC and ISH methods are being employed in attempts to measure prognostic markers, the traditional cavalier approach to sample preparation (FFPE) has emerged as a critical problem. Now the question is "Just how much of the analyte (e.g., Her2) is present?" Not merely is it there, or not there, as might be sufficient in applying IHC to identify a lineage related marker (e.g. keratin in a putative 'epithelial' cell). The problem reached national attention with the increasing use of IHC findings, as entry criteria for patients into clinical trials (exemplified by staining for Her 2 or CD20, as indicators of possible effectiveness of monoclonal antibody therapy). The challenge became to 'standardize' the IHC or ISH stain (i.e., in effect, turn it into an assay), which in turn led to the recognition and then the affirmation that 'sample preparation' was a critical part of the process, and hence the issuance of the RFA CA 06-007 the essence of which is as follows 'enhancement or adaptation of sample preparation methodologies and technologies—, the development of assays to assess sample quality'.

Preliminary Studies:

Under our previous award (NIH 1 R33 CA103455-01—R21/R33 "Retrieval of DNA and RNA and Protein from Archival Tissues") the possibilities of using AR derived methods for recovery and/or extraction of major classes of analytes from FFPE tissues have been extensively explored. Feasibility has been shown for qualitative demonstration of representative key analytes in tissue sections using Antigen Retrieval (AR) methods followed by IHC for protein, or ISH for RNA and DNA, using methods that are in general use in Pathology departments worldwide. Furthermore we have shown that extraction protocols derived from these same basic AR methods have been successful in recovery of proteins for Western blots and mass spectrometry analysis, and in recovery of DNA for Southern blots and PCR based methods[14, 15, 34]. Dr Singer, an IMAT investigator and our consortium collaborator has shown initial successes for the demonstration of RNA in FFPE tissue sections[35].

As noted above, we have concluded that the scientific and practical problems fall into three major areas:
1. lack of standardization of sample preparation,
2. lack of reproducibility of AR and IHC (ISH) protocols,
3. lack of available universal reference materials (standards) for the major classes of analytes that would permit calibration of the analytical method and quantification.

Most approaches to improving the overall quality of IHC and ISH staining methods have revolved around solving one or more of the three problems described above. To date our approach has been different. We have recognized the intrinsic difficulties of achieving uniform improved sample preparation, and have instead used AR to 'repair' or 'minimize' the resultant variations.

AR ('Antigen Retrieval') for IHC, ISH and Extraction of Analytes.

We have taken the approach that the problem of improved and standardized sample preparation (for FFPE), has not yet been solved. In addition, we recognize that solving the problem of 'sample preparation' going forward, still will not address the issue of performing studies on existing archival tissues, which form the basis for evaluating entry to current clinical trials. For these reasons we chose in our existing R33 proposal to focus upon the antigen retrieval (AR) approach, attempting to reverse the effects of formalin fixation, while possibly also minimizing the effects of varying fixatives and fixation times. In this regard the AR method has had major impact upon the application of IHC techniques to archival FFPE tissues, beginning in 1992, extending to today, when AR is in routine use in essentially all surgical pathology laboratories worldwide[1, 36-63]. We have also reported success in adapting the basic AR methodology to extraction of proteins from FFPE sections for SDS-PAGE and mass spectrometric analysis and in extraction of DNA and RNA for PCR based analyses[14, 15, 34]. However in the conduct of these studies we encountered significant limitations, namely that for all of these analyses, from IHC and ISH 'stains' in tissue sections, to mass spectrometry and PCR of tissue extracts, reproducibility remained poor and results that were qualitative rather than quantitative.

Reference Standard—'Faux' Tissue and Protein Standards.

To begin to address the issues of reproducibility and quantification, we had also proposed (in the existing R33 award) to explore simultaneously the third problem area, namely the development of a universal reference standard. In this context we have reported the development of 'faux' tissues or histoids in collaboration with Drs. Imam and Ingram at the Huntington Research Institute[1, 64]. We have prepared multiple batches of 'histoids' containing 2 and 3 different cell types, that have been pelleted, formalin fixed and paraffin embedded (FFPE) to yield 'faux' tissue blocks. We have further analyzed the FFPE histoid blocks from within the same batch, and batch to batch, for reproducibility of IHC staining, and for quantification of extractable selected proteins, by reference to 'fresh unfixed' samples. The conclusions are that standardization of analyte (protein) content from batch to batch, while encouraging, is at present still unsatisfactory (the use of cell lines per se has of course been employed for a FDA approved Her2 'staining test' (Dako), but the results are only crudely quantitative and are notoriously difficult to reproduce among labs and pathologists). Also the practical issues of 'scale up' to a level of production and development of methods of distribution that would make standardized histoids widely available, are at present insurmountable, primarily for economic reasons. We are confident that these scientific and practical problems could be resolved over time, but have been unable to identify a source of funding (either by grants of industrial sponsorship) for such prolonged work project. We also have described prototypic work employing 'protein embedded' materials as a reference standard for defined antigens[65]. The problems of developing purified protein standards, are both similar and different; similar in that the logistics of distributing any reference standard and incorporating the appropriate standard into FFPE blocks routinely (for each different stain) are daunting; different in that the technical challenges to preparing standard protein blocks that will survive FFPE, plus sectioning and staining have been explored by us, and others, with very limited success[1, 57, 65-71]. The initiation of this work and the Total Test Approach was presented by the PI at a NCI/EORTC sponsored conference held at NIST (National Institute of Standards and Technology, Washington D.C., June, 2002), where the problems of sample preparation and lack of reference controls again emerged as critical and unresolved issues.

Quantitative StaRT-PCR: Preliminary Data

StaRT PCR, a standardized multi-gene expression analysis system that is an established technique in our laboratories[78]. StaRT-PCR (Standardized Reverse Transcription Polymerase Chain Reaction developed by Gene Express Inc. Toledo, USA) offers a quantitative approach to measure gene expression and has been employed by us to generate data here at USC, and in collaboration with the Standardized Expression Measurement (SEM) Center at Toledo. The platform technique employs competitive templates incorporated into standardized mixtures of internal standards (SMIS) at precisely predetermined concentrations. These SMIS include internal standards for both the target and reference genes (e.g., ACTB). The data are represented as true numerical values that can be mathematically manipulated, allowing calculation of gene expression indices for the direct comparison of experimental results. Each gene expression result is reported as "number of molecules mRNA for gene per $10^6$ molecules of reference gene such as ACTB. Serial dilutions of the standardized mixes allow quantitative measurements over the 6 log range of gene expression. The StaRT PCR method will be made quantitative by use of ubiquitous or house-keeping RNAs as internal reference standards, such as beta actin or GAPDH (Table 4), and can compare transcript values numerically both within samples as well as across samples, providing a uniquely quantitative assay. The fixation and other preparatory steps of sample preparation leading to FFPE tissues will cause variable (and unknown) degradation of RNA. Our preliminary work leads us to believe that degradation is likely to affect different RNAs relatively uniformly, such that the internal reference standard RNA(s) and the test analyte RNAs will be affected similarly, allowing for quantification across different FFPE tissues, because the StaRT PCR quantification of target analyte depends upon comparison with the internal reference standard (the degree of validity of this notion will become apparent through the work on Aims 2 and 4). Real time Q-RT-PCR is different; while it may be quantitative, it does not include this intrinsic control, and does not therefore lend itself to evaluating the different effects of degradation of different tissues.

Our proposal, which is entirely novel, is to combine the advantages of StaRT PCR with SMIS (standardized mixtures of internal standards), selecting the internal standards from within the FFPE tissues (i.e., QIRS or Quantifiable Internal reference Standards) in order to quantify RNA from tissue fixed under differing (unknown) conditions, such that starting copies of target (test) analytes are expressed relative to a known copy number (1,000,000) of the internal standard. Thus for this study the SMIS will in practice be the native templates within the FFPE tissues, that are subjected to exactly the same preparation steps as the test analyte, allowing quantification.

StaRT PCR is less than 10 years old has a technique, and has been little used. We have employed it in novel studies relating to clinical applicability and validation[78]. We examined its applicability for molecular stage prediction in bladder cancer, employing both supervised and unsupervised data analysis through an iterative learning process called genetic programming. Transcript profiling data from bladder tumor tissue of 60 patients was examined by a N-fold cross validation technique for 'genetic programming', demonstrating 81% accuracy and 90% specificity in predicting nodal status. The StaRT PCR method proved to be reliable and reproducible in our hands, especially with respect to producing quantitative data[78].

RNA peT-FISH

This method for demonstrating gene expression profiles in individual cells in FFPE sections has been developed in the laboratory of our consortium collaborator, Dr. Singer[35], and was presented at the September 2005 IMAT meeting. The method was effective on a variety of FFPE tissues, yielding predictive quantitative gene expression signatures. This method provides the basis for development of a rigorously validated quantitative ISH method that will be intrinsic to this proposal.

Need for a Different and Novel Approach

Hypothesis:

Absent improved and uniform sample preparation for FFPE, and absent available reference standards, we present the hypothesis that analytes (proteins and RNAs) present intrinsically within tissues and common to all (almost) tissue types may be employed as quantifiable internal reference standards, against which sample quality can be directly assessed and key analytes can be directly quantified.

It is proposed that at all IHC assays (stains for protein), for which the goal is a quantifiable result, will be in the form of 'double IHC stain reactions', including a 'stain' for a Quantifiable Internal Reference Standard, and a second 'stain' for the unknown 'test' analyte. The amount present of the unknown 'test' analyte (protein) may then be measured with accuracy (degree thereof to be established) by comparison of the intensity of stain of the 'test' analyte with the intensity of stain of the internal reference standard, using validated quantitative IHC protocols and existing image analysis equipment and software. Having previously established the extent to which the internal reference standard(s) is preserved following FFPE with optimized AR, then a 'correction factor' (Aim 5) and a 'relative loss factor' (R33 Aim 1) can be applied to provide a quantitative measurement of the amount of unknown test analyte present in the tissue prior to the initiation of sample preparation (i.e., when it was removed from the patient). A similar rationale can be applied to the development of internal RNA reference standards, as was incorporated in the design of the peT-FISH method by Dr. Singer.

The idea of utilizing 'internal controls' for simple qualitative assessment has wide prior use in traditional qualitative IHC, as exemplified by plasma cell staining in evaluating whether a stain for kappa chain has 'worked', or not (reviewed in[1]). There is also precedent in the use of internal controls to assess crudely the extent of overall 'loss of antigenicity' following FFPE, by staining for vimentin, which is 'formalin sensitive' and is also present in almost all tissue samples[72]; the implication being that the degree to which vimentin 'stains' may serve as an indicator of the expected degree of staining of other proteins (analytes). Also the idea that the effects of different FFPE processing during sample preparation may be minimized by the use of an optimized-AR protocol, resulting in improved reproducibility of IHC staining was pioneered by our group[1, 41, 66, 73], and has been proven effective for qualitative IHC studies among different laboratories[33, 74-76]. There is also the important precedent in a prior IMAT sponsored study, of the work of Dr. Robert Singer, collaborator on the present proposal, using house keeping gene RNAs (e.g., SMG mRNA, a gene expressed by all cells and detected in 40% of the cells in the tissue), as internal references standards the peT-FISH method applied to paraffin embedded tissues[35]. Last there is the analogy of the standardized RT-PCR (StaRT PCR) method, which is quantitative by virtue of incorporation of standardized mixtures of internal standards (SMIS) at predetermined concentrations and comparison with internal actin mRNA transcripted (widely distributed in different cells) as the reference control[77]. As described above we have successfully employed this technology to quantify transcripts in bladder cancer cell lines and tumor tissues, and demonstrated its superior reproducibility and consistency in relation to real time PCR[78]. The quantitative character of StaRT PCR as applied to extracts y our laboratory make it the method of choice for independent validation of RNA degradation/recovery during sample preparation in establishing the FFPE FSIH quantifiable internal reference standards in this proposal.

Overall Significance—Towards the Ultimate Goal of Molecular Morphology

In the year 2006, cancer still is diagnosed by the surgical pathologist with his/her microscope using methods that essentially are unchanged over 150 years, from the teaching of the first histology course (John Hughes Bennet, Edinburgh, 1842) to the first textbook of surgical pathology (Rudolph Virchow, Cellularpathologie, Berlin, 1858)[1, 94,95]. That this remains true in 2006 is astonishing, in an era viewed by the public, politicians and many scientists, as the era of molecular biology and genetics. The primary reason for this anachronism is simple, that translation of 'molecular methods' from the bench to 'routine' diagnostic practice, has been greatly hindered by the fact that, worldwide, the method of sample preparation for surgical pathology is FFPE, which is satisfactory for the preservation of morphologic details, but is certainly not the method of choice for molecular immunologic assays (including ISH and IHC)[94-97]. The enormous variation in the actual protocols for FFPE employed in different labs, or in the same lab from specimen to specimen, compounds the problem and is a major factor in the current poor reproducibility of these methods. The availability of effective, reliable, quantitative IHC and ISH methods would allow visualization and ultra-cellular localization of key analytes, important to the diagnosis and prognosis of cancer, in conjunction with traditional surgical morphology criteria used for cell recognition and diagnosis. This combined dual capability is becoming known as Molecular Morphology. It is the raison d'etre of Applied Immunohistochemistry and Molecular Morphology), the journal of which the PI is the editor in chief. Molecular Morphology is in fact the basis of 80% of scientific papers published today in diagnostic surgical pathology. Surgical pathology (cancer diagnosis) has thus been totally transformed by the advent of IHC and AR methods to date[1]. Rendering the method both reproducible and quantitative would mean that both IHC and ISH stains function as tissue based assays, not just stains, and that the future has arrived[94,95,97]. Ultimately it will be possible reliably to measure RNA and protein, the end products of gene action, in situ within individual cells, leading to new criteria for cancer diagnosis and prognosis. In research the significance is equally profound, in that evaluation of gene activity (by RNA expression and protein production) allows scientists and clinicians to gain information at the molecular level regarding the function of genes. To be able to combine this capability with localization and quantification at a sub-cellular level will open new fields of study, particularly with regard to the pathogenesis of cancer.

Research Design and Methods

The feasibility of using internal analytes (proteins and RNAs) as reference standards will be established. Coupled with the necessity for internal reference standards is the requirement for assay methods that lend themselves to quantification. The construction and validation of quantitative IHC and ISH methods is thus intrinsic to this proposal. Once established and tested with the corresponding reference standards, these methods will permit the localization and measurement of a wide range of key analytes (proteins, RNAs and DNAs) within recognizable cell types in normal and pathologic tissues, combining the specificity of immunologic and molecular methods with morphologic criteria, for the diagnosis and prognosis of cancer, namely 'molecular morphology'.

Specific Aim 1—to select 2 analytes (each, of proteins and RNAs) as candidate Quantifiable Internal Reference Standards, that are expected to be present at relatively constant concentrations within cell types that are common to (almost) all tissues, and to demonstrate that these proteins and RNAs are present during the steps of sample preparation (fixation/processing) in a consistent/predictable manner.

The proteins for initial study will be selected on the basis of our in house experience and the literature (e.g., CD45, CD20, vimentin, Her2)[1, 79-82]. For other proteins preliminary IHC studies will be conducted to confirm reported ranges of tissue distribution, (e.g., endothelial markers, CD31 and Fli1 widely distributed, CD34 and VWF variable[83]), and to study the quality of available reagents (e.g., fibroblast surface protein using the Sigma IB10 antibody). In parallel to the protein analyte studies the intent is to select 2-4 RNA analytes (such as house keeping gene RNAs—see below) that are expected to be present at relatively constant concentrations within cell types that are common to (almost) all tissues, and to determine whether these RNAs are affected by the steps of sample preparation (fixation/processing) in a consistent/predictable manner. FFPE preparations (cell blocks) from cell lines have been chosen for this initial R21 phase study, as opposed to the use of either natural murine tissues or human tissues. This decision was based upon the relative simplicity of ensuring a single cell type in FFPE cell line blocks, as opposed to tissue samples. Cell line blocks yield pure cell populations for extraction of protein and RNA, to calculate the amount of analyte per cell, which is considered essential to validate the quantitative IHC and ISH analyses that will be performed on the FFPE sections of the cell blocks. Tissue sections with LCM methods will not yield pure cell populations, and the cells that are obtained will not represent intact whole cells, having been cross cut in preparation of the section; they would not therefore be suited to calculating quantities of analyte on a per cell basis. It is proposed that based upon 'proof of principle' in this cell block study, the work will be extended to normal and pathologic human tissues in the subsequent studies, using the per cell quantitative data from this study. Two to four cell lines will be selected as representative of four cell types commonly present in surgical pathology tissue sections; namely lymphocytes, endothelial cells, fibrocytes and epithelial cells (Table 4). These cell lines are all available in the USC laboratories and have been employed for the production of FFPE cell line blocks, by collecting aliquots of cells from culture, embedding in agar, fixing in 4% formaldehyde and then following 'routine' processing and paraffin embedment, with passage through xylene and graduated alcohols. In preliminary studies the selected cell lines will be grown in large batches and aliquots will be reserved for the different processing steps of FFPE. Fresh' samples taken directly from active culture to liquid nitrogen will represent the 'absolute' reference standard for quantitative measurements. Other aliquots will be processed through the different steps of 'routine sample preparation' to FFPE pellet blocks as described above. Loss of analytes (protein or RNA) may be anticipated to occur at different steps in the sample preparation process, differing somewhat for proteins as a class, as opposed to RNA as a class (Table 2).

TABLE 2

Comparison of anticipated extent of loss/degradation of proteins and RNA in sample preparation

| Analytes | Pre-fixation steps (degradation) | Fixation/processing steps ('formalin masking') |
|---|---|---|
| Proteins | + to ++ | +++ to +++++ |
| RNA | +++++ | + to ++ |

(+, minor loss, to +++++, major loss)

In order to study these effects (losses of analyte) during the different steps of sample preparation different cell line aliquots will be subjected to differing 'pre-fixation' or hold periods (simulating time elapsed for removal of tissues from body and for transport to lab), with fixation time held constant, and to different fixation times, with the 'pre-fixation' (transport) step as time 0 (zero) minutes. The experimental construct is summarized in Table 3. Times will be adjusted to focus on 'key areas of loss' as preliminary results are obtained. The AR protocol to be employed will be determined for each analyte by our published 'test battery' approach[41, 57, 73, 84, 85] that has been widely adopted by research and service laboratories. The work will first be performed for 2 or 3 selected proteins, with aliquots reserved for subsequent study of the corresponding RNAs. The initial proteins to be studied will be from the cytoplasmic group, such as actin, vimentin, and B2 microglobulin, because of their ubiquity, relative abundance, established IHC staining protocols and reagents. A similar process will then be followed for RNA analytes. While exact correlations between the amount of protein and amount of RNA for any particular analyte are not expected, and losses may occur at differing steps in sample preparation, general trends may be observed for the corresponding analyte (e.g., Her2 protein and Her2 RNA) justifying the selection of protein/RNA pairings where ever feasible. Specific Aim 1 will be considered complete when 2 different protein analytes and 2 different RNA analytes have been identified in at least two different cell lines and have been shown to be present (qualitatively) for each of the listed steps of sample preparation.

TABLE 3

Summary of study design

| Sample Prep'n Steps | Absolute fresh (unfixed) min | Pre-fix period (delays/transport, etc.) mins | | | FFPE fixn time | | | | AR - Optimized for each analyte |
|---|---|---|---|---|---|---|---|---|---|
| | | mins | Hr | hrs | hrs | hrs | hrs | Hrs | |
| Procedure | | | | | | | | | |
| for FFPE section | 0 | 30 | 1 | 2 | 4 | 8 | 12 | 24 | AR + or − |
| for extract | 0 | 30 | 1 | 2 | 4 | 8 | 12 | 24 | AR + or − |
| A. PROTEIN analytes | | | | | | | | | |
| FFPE section IHC | 0 | 30 | 1 | 2 | 4 | 8 | 12 | 24 | AR + or − |
| Extract ELISA | 0 | 30 | 1 | 2 | 4 | 8 | 12 | 24 | AR + or − |
| B. RNA analytes | | | | | | | | | |
| FFPE section PeT-FISH* | 0 min | 30 | 1 | 2 | 4 | 8 | 12 | 24 | AR + or − |
| Extract StaRT-PCR | 0 min | 30 | 1 | 2 | 4 | 8 | 12 | 24 | AR + or − |

*Tissues as much as 22 years old were used in pilot studies

Specific Aim 2—to make extracts from the cell line blocks at different steps of sample preparation and measure accurately the amount per cell of (a) each selected protein using standard ELISA methods, and (b) each selected RNA using quantitative Start PCR.

(a) Protein. ELISA methods (enzyme linked immuno-sorbent assays) comprise one of the 'standard methods' for accurate measurement of proteins in serum in clinical laboratories, including our own clinical laboratories here at USC. The accuracy of ELISA is well established, with quantitative results derived by densitometric/colorimetric measurement of the unknown test analyte sample against a reference calibration curve generated from known (reference) standards (of the purified protein analyte) under strict protocol conditions. In this proposal, ELISA will be developed and performed to quantify the selected analytes in the 'Extract' aliquots, reflective of the different steps of sample preparation (Table 3). The ELISA assay will be established with the same reagents (primary antibodies) as are employed for the IHC stain protocols (see below), and the methods will be cross validated. By use of extracts of cell line preparations containing known numbers of cells, the 'average' amount of the reference analyte in an individual cell will be determined by the ELISA assay, and will then be used to calibrate the IHC method for amount analyte in a single cell as determined by quantitative image analysis (Aim#3). It is believed that the calibration of the IHC method versus ELISA can be established even in the event that FFPE processing renders protein extraction difficult, because calibration can also occur using the non-fixed materials. In addition, we believe that we will extract sufficient immunologically intact protein for ELISA studies, based on our experience in our existing R33 study (Retrieval of DNA, RNA and Protein from Archival Tissues), where this approach has in fact yielded sufficient amounts of intact protein for SDS PAGE analysis and for mass spectrometry, both in our laboratory and in collaboration with Calibrant, using their mass spectrometry system (both studies reported at the Sixth Principle Investigators Meeting IMAT Program, Sep. 7-9, 2005). ELISA also will be compared with calibrated Western blot gel methods[34]; if the latter are more accurate and more cost effective then this approach may replace ELISA where possible.

(b) RNA. The same FFPE blocks will be used as for protein studies. Extracts of RNA will be made from cell line blocks using modified AR methods developed for recovery of analytes from archival tissues. The amount per cell of each selected mRNA will be measured using StaRT PCR, a standardized multi-gene expression analysis system that is an established technique in our laboratories[78]. The StaRT PCR method will be made quantitative by use of ubiquitous or house-keeping RNAs as quantifiable internal reference standards (QIRS) as described. We will employ specific transcripts (e.g., actin, Table 4) as targets for StaRT PCR amplification in order to establish internal quantifiable standards; the transcript numbers will be expressed per million actin mRNA molecules. We will also investigate the use of beta-2-microglobulin and GAPDH transcripts as internal housekeeping gene quantifiers besides actin. Effects of variations in pre-fixation periods, nature of fixatives, and presence or absence of antigen retrieval procedures on the quantitative presence of the analytes will be assessed. The PCR method will be adapted for FFPE cell line blocks by use of competitive templates and target amplicons that are shorter than usual. This is because some degree of RNA degradation is expected during FFPE and the analytic method must address this degradation. We have found that the design and use of short competitive templates is straightforward, which makes the method uniquely amenable to the assay of partially degraded mRNA templates.

We recognize that StaRT PCR method was first published almost a decade ago, but our work is the first time that it has been adapted to extracts of FFPE sections. StaRT PCR is being used here as an independent measure of RNA degradation and recovery (for comparison with ISH data), in parallel to the use of ELISA to measure protein (for comparison with IHC). We have chosen to use StaRT PCR to measure RNA during the steps of sample preparation because intrinsic to the method is the use of internal controls, which allows assessment of variability of RNA degradation from FFPE block to FFPE block. Real time PCR has of course been used to quantify RNA in extracts of FFPE tissue, but it does not allow direct comparison of quantitative data from block to block and therefore does not allow for assessment of RNA degradation during sample preparation, a factor which is key to the current proposal. In addition, we have direct experience in quantitative and comparative use of the StaRT PCR method in our laboratory[78].

Start PCR-Concise Method[77, 78]

FFPE tissue sections will be lysed in TRIzol®, 400 μL of chloroform is then added, followed by centrifugation to separate the RNA-containing aqueous phase. Following addition of linear acrylamide (Ambion, Austin, Tex., USA) as a carrier and 1 mL of isopropanol to precipitate RNA, incubation at −80° C. for two hours, washing in cold 70% ethanol, and drying the RNA is resuspended in DEPC-treated water, for DNase treatment using DNA-free™ (Ambion, Austin, Tex., USA). cDNA is prepared using Superscript II as prescribed by the manufacturer (Invitrogen, Carlsbad, Calif., USA). Internal standard competitive template (CT) mixtures over 6 logs of concentration (A-F) will be obtained from Gene Express, Inc. (Toledo, Ohio). Each of the six mixtures contains internal standard CTs for nearly 400 target genes; our study will target a list of specific up to 6 transcripts (beginning with Table 4). Thus each sample will undergo six separate PCR analyses; each separate reaction containing the ready-to-use master mixture, cDNA sufficient for expression measurements of the target transcripts, primers for the target transcripts and one of the six CT mixes (including β-actin CT at a fixed concentration of $10^{-12}$ M). The competitive PCR products will be electrophoresed using capillary electrophoresis in collaboration with Gene Express Inc. and image analysis and quantification of band fluorescence intensities will be done as prescribed by GeneExpress Inc. Specific Aim 2 will be considered complete with the successful measurement of the average analyte per cell for 2 or more candidate reference proteins and 2 or more RNAs in 2 or more different cell line blocks at different stages of sample preparation as delineated in Table 3.

Specific Aim 3—to construct quantitative IHC methods, using the same antibody reagents as in the ELISA assays, and to validate IHC derived measurements of protein per cell by comparison to the ELISA data. This aim includes testing the IHC method for consistent generation of label (chromogen), to allow for strict quantification in cell block sections.

IHC Staining Protocols and Reagents; Validation and Calibration to Elisa Methods IHC methods as applied to tissue sections are strictly analogous to existing ELISA methods and will be constructed using the same reagents (primary antibodies) as are employed for the ELISA assay protocols (Aim #2). The IHC method will be calibrated for the amount analyte in a single cell as compared to the single cell average measured by ELISA. Quantitative image analysis will be employed to 'read' the IHC staining results, using image analysis software and hardware available in our laboratory (the FDA approved Clarient/ChromaVision image analysis system will be used, with the addition of Spectral Analysis). Tests will be conducted on multiple replicate cell block FFPE sections to assure reproducibility of the IHC staining result (run to run, and batch to batch), including evaluation of consistency in generation of chromogenic product by the enzyme label (peroxidase or alkaline phosphatase), which may vary with time and temperature of incubation and is more difficult to standardize in tissue sections than in ELISA assays. In the event that consistent label generation proves difficult, immunogold methods will be employed, with a known and fixed average particle number per antibody molecule[86-88]. The IHC single and double stain methods in daily use in our laboratories will be used directly in this study, using the basic ABC method with peroxidase/DAB and alkaline phosphatase/fast red, performed on a Biogenex automated immunostainer with an open software program that allows for specifically tailored protocols to incorporate directly reagents identical to those used in the ELISA protocol. Mixed polymer based labels (from Biocare Medical) will also be employed for double IHC methods, because of their excellent reproducibility in our hands, coupled with clear signals that have shown good results by differential spectral analysis proposed for the R33 phase. All of these methods are described in more detail by reference to the standard text—'Immunomicroscopy". A Diagnostic Tool for the Surgical Pathologist' (Edited by the PI—Chapter 1)[1]. Specific Aim 3 will be considered complete with the demonstration of a direct quantifiable relationship between IHC and ELISA for 2 (or more) analytes in corresponding FFPE sections and extracts.

Specific Aim 4—to construct quantitative ISH methods and to validate ISH derived measurements of protein per cell by comparison to the StaRT PCR data.

ISH Staining Protocols and Reagents, Validation and Calibration to Start PCR Methods This aim includes testing the peT-FISH quantitative RNA method developed by the consortium collaborator, Dr. Robert Singer for reproducibility at the different steps of FFPE, with respect to quantification of selected mRNAs per cell, in comparison to the StaRT PCR data generated previously from the same FFPE cell line blocks (Aim 2). This goal will be accomplished by means of a 'consortium/contract' with Dr. Robert Singer using the quantitative peT-FISH method[35], developed in a prior IMAT supported study described at the Sixth Principal Investigators Meeting IMAT Program, Sep. 7-9, 2005. The method utilizes FFPE sections with an in situ AR process employing sodium borohyride and high heat. In Dr. Singer's hands this method has provided good quality RNA, excellent hybridization characteristics, and excellent sensitivity, without troublesome autofluorescence. In initial studies house-keeping genes, such as ACTB and SMG1 were used as quality control standards, with staining results interpreted by image analysis. Other recent studies also describe methods for optimizing FISH in FFPE tissues, providing alternative approaches should validation prove difficult[89]. Dr. Singer's laboratory has in place the Nuance spectral analysis system that is proposed for the higher level analysis. The availability of the peT-FISH method for RNA quantification, also provides an alternative experimental approach for establishing internal RNA reference standards in the event that difficulties are encountered in validating the quantitative StaRT PCR method. The goal is to make an initial determination of the feasibility of developing internal RNA standards, and to assess the complexity of the task in comparison to the development of protein standards already described, retaining the flexibility to move RNA to the forefront, if the methodology proves more tractable than protein based methods.

Specific Aim 5—to determine whether the candidate protein and RNA analytes, once identified and quantified, show consistency in behavior when tested by quantitative IHC and ISH at different stages of FFPE and in different FFPE cell line blocks, as would be required of a candidate tissue internal reference standard (i.e., is the loss/recovery of each candidate analyte consistent to a useful degree across different FFPE blocks).

By application of the validated quantitative ELISA and IHC methods (Aim 3) and the validated quantitative StarRT PCR and ISH methods (Aim 4) the actual amounts and 'loss' of measurable reference analyte can be determined on a cell to cell basis at each step of sample preparation in 'extracts' and 'sections' (Table 3), by comparison with the corresponding fresh unfixed (0 min. time) aliquot as the 'starting standard'. Furthermore the absolute and proportionate losses can be determined for each preparation step for different reference analytes in several cell lines, to determine whether a consistent and predictable pattern exists. While this initial phase assesses multiple steps in the FFPE process to facilitate understanding of the process in this early phase of the study, the key data are of course for the first 'unfixed' (0 time) step and the FFPE step. If a consistent relationship can be demonstrated experimentally then this relationship can be calculated and codified as the 'correction factor' for that reference analyte (i.e., proportionate difference between unfixed and FFPE material). This experimentally derived 'correction factor' can then be used in conjunction with the controlled IHC stain (or ISH stain as appropriate) and quantitative image analysis to calculate the absolute amount of the reference analyte present in the cells of the original sample. It is to be expected that for any single analyte (protein or RNA) the experimentally derived 'correction factor' will vary under different sample preparation conditions, and that different candidate reference analytes will also show differing 'correction factors'. One of the goals of Aim 5 is to determine experimentally how great such variations are, what can be done to minimize or compensate for such effects, and whether certain proteins and RNAs can be identified that show minimal variation across a broad range of sample preparation modalities (i.e. show the least change in experimentally derived 'correction factor'); such analytes can provide the best candidates as standards.

Under Specific Aim 5 the ELISA/IHC and StaRT PCR/ISH methods will be applied systematically and in parallel for one selected analyte in one cell line block at each stage of sample preparation (Table 3). The following describes the process for protein analytes, and will be repeated in analogous fashion for RNA analytes. For proteins it is proposed to begin with actin, B2 microglobulin or vimentin (for proteins), the initial choice being predicated upon findings of preliminary studies in Aims 1-4. With successful completion of one analyte in one type of cell block the same study will be repeated for the same analyte in a second and third type of cell block (Table 3), and then for a second analyte in the same 3 types of cell blocks. In each example the results will be confirmed by repeating the assays in triplicate on different days to test reliability. The measured amount of each protein per cell (by ELISA and IHC) will be assessed at every stage of the preparation process for each analyte in an effort to identify analytes that are ubiquitous and are affected consistently and reproducibly by the sample preparation process (i.e., under experimental conditions show a constant calculated 'correction factor'). Such analytes, when identified, are considered candidate internal reference standards for incorporation in a reference standard panel (Aim 6). Other immediate goals for Aim 5 are to confirm the validity of the experimental construct, to fine tune it if necessary, and to confirm the reproducibility of the ELISA and IHC methods (run to run variation) under closely monitored conditions. Also as noted, the commonly employed IHC methods employ peroxidase or alkaline phosphatase to develop the appropriate chromogens. Although well controlled in ELISA protocols, these reactions may not be sufficiently well controlled in a tissue section environment to assure uniform development of the chromogen as will allow quantification. If this proves a problem in examination of multiple samples (including always a constant reference standard—the 0 min time aliquot), other chromogens that rapidly reach reaction end point will be tested, or immunogold or silver labels will be employed, with the advantage of a known direct and fixed relationship between the number of gold particles and the target antigen[88, 90]. Parallel studies (Table 3) will be carried out for the candidate RNA reference standards, comparing the StaRTPCR data on extracts (USC) with the peT-FISH data on sections (Dr. Singer at AECOM), using the same FFPE cell line blocks. Again data will be shared to cross validate the methods, and run to run reproducibility will be tested. Specific Aim 5 will be considered complete upon validating the design and the ELISA/IHC methods for two analytes in 2 different types of cell blocks; and similarly the StaRT PCR/peT-FISH methods for 2 analytes in 2 cell line blocks.

Specific Aim 6—to extend the range of protein and RNA analytes studied (under Aims 1-5) in order to construct a panel of 3 protein analytes (ideally one each of cytoplasmic, cell surface and nuclear proteins) and 3 RNA analytes as candidate internal reference standards in the FFPE cell line blocks. The goal of assembling a 'panel' is to maximize the chances of finding a standard with similar characteristics (after FFPE) to clinically important test analytes (R33 Aim 1). Note that while the R21 aim is to establish a panel of 3 analytes, all promising candidate standards will be carried forward for testing on human tissues (Aims 3-6, Part II). In the case of proteins those analytes identified in Aim 5 as having consistent and predictable patterns of behavior during sample preparation, will be considered as candidate reference standards. Additional cytoplasmic proteins, and then cell surface and nuclear proteins will then be examined by ELISA and IHC on FFPE 'extracts' and in 'sections' in an identical fashion (Tables 3 and 4), again with the immediate goal of determining whether each or any of these additional analytes also show patterns of loss and recovery, after sample preparation and AR, that are consistent from block to block, within the same cell line and in different cell lines (i.e., constant correction factors). The end goal of Aim 6 is to establish a panel of 3 (or more) reference proteins that behave consistently in FFPE cell blocks and also are expected to be widely distributed in surgical pathology tissues. Analysis of the measured amount of 'analyte per cell' from the ELISA and IHC studies for aliquots of the same cell line subjected to the same and different steps of sample preparation (Table 3) will provide the necessary data set to determine whether any of the tested proteins show a reproducible and predictable pattern of loss or retention under different conditions, such that correction factors (Aim 5) can be derived to allow for accurate calculation of the amount of the protein in the original fresh cell line preparation. As a final qualification, the validity of the candidate reference proteins will then be tested by preparation of new cell line FFPE blocks, measurement by quantitative IHC of the amount of the protein in FFPE blocks, calculation by use of the correction factor of the protein expected to be present in the original unfixed cells, and comparison of this result with direct measurement of protein per cell by ELISA. Parallel studies will be conducted for candidate RNA analytes by StaRT PCR on extracts (USC) and peT-FISH on FFPE sections (AECOM by Dr. Singer) to construct a RNA reference panel.

It is recognized that statistical treatment of the data and experimental design will be necessary to assure significance and validity of the findings on human tissues, once initial feasibility is established in cell line block studies; this design and work is reserved to the Part II phase. In addition as the work proceeds through Aims 1-4, if either of the protein of RNA methods show greater facility for the development of reference standard panels, then this aspect of the study will be advanced with the goal of testing human tissues at the earliest valid opportunity. Specific Aim 6 will be considered complete when 2 panels, one consisting of 3 (or more) reference proteins and another consisting of 3 (or more) reference RNAs, are assembled and tested in cell line blocks, by both IHC and ISH, according to the overall schematic shown in Table 4, recognizing that as the work proceeds it may be necessary to explore additional analytes, than those named. These will be selected for clinical utility and based upon initial findings as to which classes of proteins and RNAs show most promise after preliminary studies.

TABLE 4

Internal reference standards: candidate cell types and analytes having broad tissue distribution

| Cell type (Cell lines*) | Lymphocyte (Raji or HL60) | Endothelial cell (HuVEC) | Fibroblast (LD419) | Epithelial (breast) (MCF7, MDA, MB468) |
|---|---|---|---|---|
| Analytes Proteins | | | | |
| Cell Surface | CD45 CD20 | CD31 | Fibroblast "surface protein" | Her2 EGFR |
| Cytoplasm | Actin B2 microglobulin Vimentin | Actin B2 microglobulin Vimentin Factor VIII | Actin B2 microglobulin Vimentin Factor VIII Desmin | Actin B2 microglobulin Vimentin |
| Nucleus | Histone H1 MiB1 (Ki-67) | Histone H1 MiB1 (Ki-67) | Histone H1 MiB1 (Ki-67) | Histone H1 MiB1 (Ki-67) |

TABLE 4-continued

Internal reference standards: candidate cell types and analytes having broad tissue distribution

| Cell type (Cell lines*) | Lymphocyte (Raji or HL60) | Endothelial cell (HuVEC) | Fibroblast (LD419) | Epithelial (breast) (MCF7, MDA, MB468) |
|---|---|---|---|---|
| RNAs | | | | |
| Cell Surface | CD45 CD20 | CD31 | Fibroblast "surface protein" | Her2 EGFR |
| Cytoplasm | Actin B2 microglobulin Vimentin | Actin B2 microglobulin Vimentin Factor VIII | Actin B2 microglobulin Vimentin Desmin | Actin B2 microglobulin Vimentin |
| Nucleus | Histone H1 SMG1 | Histone H1 SMG1 | Histone H1 SMG1 | Histone H1 SMG1 |

*All the cell lines listed are available in active growth at the KSOM Department of Pathology, either in the PI's laboratory or in collaboration with Dr. Alan Epstein, whose laboratory is located on the adjacent floor.

Part II

Specific Aims:

In brief, Specific Aim 1 will take the 2 prototypic panels of Quantifiable Internal reference Standards (one for protein and one for RNAs developed in Part I, Aim 6) and, still using FFPE cell line blocks, test the utility of these panels to serve as reference materials for a range of non-ubiquitous tissue (test) analytes. Specific Aim 2 will convert and validate the FISH method in FFPE sections to a method using orthodox light microscopy. Aims 3-6 will test and extend the reference panels in the more complex environment of normal and pathologic human FFPE tissues.

Specific Aim 1—to determine using the same cell line blocks as in Part I whether the 2 prototypic panels of 'reference' analytes (one for proteins, one for RNAs), once identified and quantified, can serve in a consistent predictive manner for other analytes, selected on the basis of being present only in some normal and pathologic tissues (i.e., does the quantified % loss of the reference analyte(s) have any predictive relationship to the % loss of other analytes [of similar class]—'relative loss factor')? Specific Aim 2—to explore conversion of the quantitative peT-FISH method to a chromogenic label system, (CISH—chromogenic ISH), compatible with orthodox light microscopy on FFPE sections; and to validate the selected method as described in Part I (Aim 4). Should the chromogenic method not lend itself to strict quantification then a gold or silver label system will be used— GOLDFISH[91] or SISH (silver ISH), both of which have been employed to demonstrate RNA qualitatively in FFPE sections.

Specific Aims 3-6 are the key aims that seek to establish the validity of the candidate reference standards in human tissues for 'routine' surgical pathology.

Specific Aim 3—to duplicate and extend using selected normal human tissue, the study design that was employed for protein on FFPE cell blocks' (Table 5A), in order to establish the validity and utility of the reference panels for proteins (developed for FFPE cell blocks) in the FFPE tissue section environment.

Specific Aim 4—to duplicate and extend using selected normal human tissue, the study design that was employed for RNA on FFPE cell blocks' (Table 5B), in order to establish the validity and utility of the reference panels for RNAs (developed for FFPE cell blocks) in the FFPE tissue section environment.

Specific Aim 5—to examine abnormal pathologic tissues, using the panels of internal reference standards established for protein in FFPE cell line blocks and FFPE normal human tissue and to test for the ability to quantify protein analytes by calculation of the amount of analyte per cell using correction and relative loss factors (as described for cell line blocks in Part I, Specific Aim 5 and Part II, Aim 1). Double IHC stains will be employed, to allow comparison of the stain reaction for the reference analyte (per cell) with the staining reaction for the test analyte (per cell), using quantitative spectral analysis.

Specific Aim 6—to examine abnormal pathologic tissues, using the panels of internal reference standards established for RNA in FFPE cell line blocks and FFPE normal human tissue and to test for the ability to quantify protein analytes by calculation of the amount of analyte per cell using correction and relative loss factors (as described for cell line blocks in Part I, Specific Aim 5 and Part II, Aim 1). Double ISH stains will be employed, to allow comparison of the stain reaction for the reference analyte (per cell) with the staining reaction for the test analyte (per cell), using quantitative spectral analysis. For this purpose the chromogenic/gold peT-ISH method developed under Aim 3 will be employed.

Background and Significance:

The Background and Significance is essentially as described in Part I, and if successful will provide the basis for establishing Molecular Morphology (the combination of quantitative molecular and morphologic criteria) as the method for cancer diagnosis, prognosis and therapy selection[94,95].

Establishing consistent patterns of retention and/or loss of protein or RNA analytes in cell line blocks (Part I) is of theoretic interest, but will only have real practical value if the findings translate to human tissues. Part II, Aims 3 to 6 therefore are the ultimate key aims of this proposal, but can only be approached by careful and rigorous performance of all of the validation steps described in the R21 and in Aim 1 of the R33 for protein and RNA.

The ability to construct a panel of Quantifiable Internal Reference Standards, employing protein (and/or RNA) analytes that have a wide distribution in human tissues, and that have predictable behavioral characteristics when undergoing sample preparation (FFPE) will provide the universal reference standards that these methodologies hitherto have lacked. Demonstrating the ability to construct panels of internal reference standards that can be applied to with IHC or ISH methods to measure accurately those analytes that do require accurate quantification will have enormous significance, greatly advancing the discovery and use of prognostic markers. The practical application is best illustrated by an example: IF it can be shown that an internal reference protein (e.g., vimentin) is (1) consistently detectable after FFPE at a level of, say, 50-60% of the amount originally present (in cells of fresh tissue) (i.e., has a stable correction factor), and (2) has a consistent relationship following FFPE and AR with a second (test) protein (e.g., Rb protein) (i.e., has a stable relative loss factor), then in a controlled double IHC stain the intensity of stain per cell for vimentin by comparison with the intensity of stain per cell for Rb protein, could be used to calculate the amount of vimentin per cell present prior to fixation (by use of the 'correction factor'), as well as the amount of Rb present by calculation (the 'relative loss factor'). On this basis it would then be possible to seek internal reference standards for key analytes, where quantification is critical. Again, by specific example, in order to develop an internal reference standard for, say, Her 2, an experimental search could be instituted for a ubiquitous protein that has a 'relative loss factor' in comparison with Her 2 protein that is consistent, and in addition has a stable 'correction factor' for sample preparation; double IHC staining of a FFPE section for Her 2 and the 'standard' would then allow accurate calculation of the amount of Her 2 present, using this internal control method, obviating therefore the errors contingent upon different methods of sample preparation. Distinction between two or more chromogens (or labels) will be needed, as will corrections for variations in section thickness and cell cuts across the section. It is envisaged that these steps will be accomplished by image analysis methods, including spectral imaging, which will be used to measure the intensity of stain of the reference standard on a mean cell basis, as the calibration marker for comparison with the intensity of stain of the test analyte.

It is emphasized that the proposed panels of Quantifiable Internal Reference Standards (QIRS) differ from 'external standards' (either proteins or cell lines) in the following important ways: 1. QIRS provide quality control of sample preparation; 2. QIRS provide a calibration standard for true quantitative assays; 3. QIRS, because they are intrinsic to the tissue section being 'stained', are inexhaustible, inexpensive and are universal, being automatically available for every IHC and ISH assay (stain). Quantifiable Internal Reference Standards thus meet all the requirements for a practical system of standards for IHC and ISH on FFPE sections[94-97].

Preliminary Studies/Progress:

As described in Part I, we have performed preliminary studies that address this proposal specifically; at USC in our current R33 award (Retrieval of DNA, RNA and Protein from Archival Tissues) and at AECOM through our collaborator Dr. Robert Singer, in developing the quantitative peT-FISH method for RNA on FFPE tissues. However, to establish credible and useful internal reference standards major validation is required, and the studies that establish 'proof of principle' and feasibility are part of Part I. In addition four peer reviewed papers from our group have been published (or are in press) in 2006 supporting the validity of the proposed approach[94-97], already resulting in invitations to present these ideas in Key Note presentations at international meetings.

Research Design and Methods:

The research design parallels that described in detail in Part I, whereby the protein and RNA panels developed in the cell line study are tested on normal and pathologic human tissues for their utility as reference standards for a range of protein and RNA analytes by quantitative IHC and ISH methods.

Specific Aim 1—to determine using the same cell blocks as in the R21 phase whether the 2 prototypic panels of 'reference' standards (one for proteins, one for RNAs), once identified and quantified, can serve in a consistent predictive manner for other analytes that are present in normal and pathologic tissues, i.e., does the quantified % loss of the reference standards(s) have any predictive relationship to the % loss of other analytes [of similar class]—'relative loss factor'?

The answer to this question will determine whether one (or more) of the proteins (and/or RNAs) in these initial panels can serve as an internal reference standard, to assess the impact of sample preparation methods upon a broad range of proteins (antigens) (or RNAs) and to permit accurate quantification of such.

It is known that not all proteins behave in identical fashion during FFPE, so called formalin 'sensitive', 'non-sensitive' etc[66, 92]. These classes of proteins show differing degrees of 'loss/recovery' after FFPE and AR; the goal of this study is to determine whether such 'loss/recovery' for a candidate reference protein analyte has consistency following sample preparation, such that the amount of analyte remaining in FFPE blocks after AR shows an acceptably consistent relationship to the amount originally present in the unfixed cell; as described previously (Aim 4); if such a consistent relationship can be demonstrated experimentally then this relationship can be calculated and codified as the 'correction factor' for that reference analyte. The correction factor can then be applied to the IHC stain reaction observed in FFPE cells (using image analysis) to calculate the amount of the reference analyte present in the unfixed state.

As part of Specific Aim 1, each of the candidate reference analytes will be compared with each of the others in FFPE human tissues to determine whether there is a consistent relationship of each one, with any of the other reference standards thus far explored. For simplicity the experimentally determined relationship between a reference analyte and any other (test) analyte is herein termed the 'relative loss factor', and is a coefficient that codifies the effect of FFPE/AR on any one test protein as it relates to the effect of FFPE/AR on a selected reference standard that shows similar behavior during FFPE. It is intended that the test analytes (proteins and RNAs) selected and studied under Specific Aim 1 will be chosen from those with clinical relevance in surgical pathology diagnosis. With protein analytes these could include PSA, p53, Rb, estrogen receptor, again selected on the basis of current diagnostic utility. Her 2 would be included here if not already evaluated. Also it is recognized that 'non-ubiquitous' analytes will include a large number of 'mutant' proteins that are the product of gene mutations or translocations common in cancer cells, as well as novel RNA expression products. It is proposed that 'relative loss factors' may also be established by experimental demonstration for many of these proteins, and their corresponding RNAs. Data from our earlier published AR studies[73, 93] suggest that the variety of responses of proteins to FFPE and the degree of recovery by AR is limited, and may allow most proteins of interest to be segregated into a small number of classes with regard to their behavior under these conditions. Such groupings might include, for example, formalin non-sensitive (<10% 'loss' after FFPE without AR), or formalin sensitive (with optimal AR at low pH, or mid-range pH, or high pH), or formalin sensitive with no useful recovery after AR. The exact categories are to be determined by experiment using data from the study, with the goal to identify and include in the panel at least one internal reference analyte from each category, which then would serve as the internal reference standard for other proteins in that category (also determined by experiment). By measurement of the intensity of IHC stain of the reference standard and comparison with the intensity of stain of the test analyte, and applying the derived 'correction factor' and 'relative loss factor' it would be possible to reach a calculated quantitative result. While absolute accuracy is not envisaged, it appears highly probable that results can be achieved that are far superior to current so called quantitative IHC measurements, that make no attempt to control for vagaries in sample preparations, and lack any objective reference standard whatsoever.

It is proposed that measurement of the intensity of staining reaction of the reference standard in comparison to the test analytes in a double IHC stain will be performed using the Clarient system, but will be supplemented by spectral analysis using the Nuance Instrument and software[95]. It is expected that this latter system (or others with like capabilities) will become the preferred approach because of accuracy and ease of application. The Nuance instrument and accompanying image analysis software allows for recognition, separation and measurement of different color signals (stains) and provides a means of quantifying any one against any other (see FIGS. 5-6). Our laboratory has a basic Nuance instrument and has been collaborating with Dr. Levenson (Cambridge Research Instruments, the manufacturer) for several years and is satisfied with the capability of this instrument. A dedicated system will be purchased. Dr. Singer already has a Nuance, which equally is adaptable to multiple fluorescence signals. Common instrumentation among the collaborators will facilitate completion of the work.

We have no direct comparable data for how different RNA molecules might behave in response to variations in FFPE and AR. However our existing R33 'retrieval grant' has shown that RNA, that is sufficiently intact for StaRT PCR can be extracted from FFPE tissues, while Dr. Singer has demonstrated that FISH methodology can be adapted successfully to demonstrate at least some RNA molecules in FFPE tissues. What remains is to establish whether patterns of loss (or recovery/retention) of RNA in FFPE are consistent to a degree that allows for their use as general standards.

Specific Aim 1 will be considered complete when a minimum of 3 'non-ubiquitous' (test) proteins and 3 non-ubiquitous (test) RNAs, have been examined in comparison with the panel of internal reference standards, to determine whether consistent patterns and relationships exist, that allow accurate measurement by IHC (using correction and relative loss factors) of the amount of each analyte per cell, as compared to the corresponding ELISA and StaRT PCR measurements of the same analyte in the same cell population.

TABLE 5

Summary of study design for R33 phase - applied to normal and pathologic human tissue blocks (tonsil)

| Sample Prep'n Steps | Absolute fresh (unfixed) min | Pre-fix period (delays/transport, etc.) | | | FFPE fixn time | | | | AR - Optimized for each analyte |
|---|---|---|---|---|---|---|---|---|---|
| | | mins | hr | hrs | hrs | hrs | hrs | hrs | |
| Procedure | | | | | | | | | |
| for FFPE section | 0 | 30 | 1 | 2 | 4 | 8 | 12 | 24 | AR + or − |
| for extract A. PROTEIN analytes | 0 | 30 | 1 | 2 | 4 | 8 | 12 | 24 | AR + or − |
| FFPE section IHC/Image Analysis | 0 | 30 | 1 | 2 | 4 | 8 | 12 | 24 | AR + or − |
| Extract ELISA B. RNA analytes | 0 | 30 | 1 | 2 | 4 | 8 | 12 | 24 | AR + or − |
| FFPE section peT-CISH/Image Analysis | 0 min | 30 | 1 | 2 | 4 | 8 | 12 | 24 | AR + or − |
| Extract* StaRT-PCR | 0 min | 30 | 1 | 2 | 4 | 8 | 12 | 24 | AR + or − |

*Parallels design for cell blocks - Table 3*

Specific Aim 2—to explore conversion of the peT-FISH method to a chromogenic label system compatible with orthodox light microscopy on FFPE sections—CISH (chromogenic ISH) which have been employed to demonstrate DNA amplification in FFPE sections; and to validate the selected method as described in Part I (Aim 4) (or gold or silver label based method, as in GOLDFISH[91] or SISH (silver ISH) if the chromogenic method does not lend itself to strict quantification).

The peT-FISH method will be adapted to a light microscopic environment that is compatible with detailed morphologic examination as in surgical pathology diagnosis, by replacing the fluorescent label with a stable chromogenic label (peT-CISH). If the chromogenic enzymatic label method does not allow strict quantification then we will move to labeling with gold particles (peT-GOLDFISH) or silver particles (peT-SISH). For these basic methodologies the reagents are widely available[1] and are already in use in our laboratory for research application in a non-quantitative manner. Our goal will be to adapt these qualitative methods to a rigorous quantitative assay, with validation for performed as described in Part I for the IHC method and for peT-FISH. The primary reason for converting the assay relates to its practical utility for surgical pathology, where light microscopy is the norm and immunofluorescence methods are employed only for limited applications, primarily because of incompatibility of the fluorescence method with evaluation of histologic criteria critical to the diagnosis. This modus operandi for surgical pathologist has not changed in 5 decades since immunofluorescence became available, and it is not going to change now. A second reason relates to the desire for a common 'image analysis' (hardware/software) approach to quantification, that is applicable both to IHC and ISH assays (stains), and will therefore be readily available to surgical pathologists. It is envisaged that automated assay protocols and computer assisted image analysis will be required for these quantitative methods. We believe that this outcome will be consistent with the new guidelines under development by the Clinical Lab Standards Institute (CLSI) and will likely be required by the FDA for approval of 'quantitative' IHC or ISH tests.

Specific Aim 3—to duplicate and extend using selected normal human tissue and the study design that was employed for protein on FFPE cell blocks' (Table 5A and 5B), in order to establish the validity and utility of the reference panels for proteins (developed for FFPE cell blocks) in the FFPE tissue section environment.

Specific Aim 4—to duplicate and extend using selected normal human tissue and the study design that was employed for RNA on FFPE cell blocks' (Table 5A and 5B), in order to establish the validity and utility of the reference panels for RNAs (developed for FFPE cell blocks) in the FFPE tissue section environment.

It is proposed to use tonsil tissue as the prototypic normal human tissue, because of the presence cell types that are candidates for the 'ubiquitous' cell types that would be expected to contain the reference analytes (lymphocytes, fibroblasts, endothelial cells and epithelial cells). Other candidate normal tissues include normal prostate, breast and spleen, that becomes routinely available in surgical pathology at USC affiliated hospitals, and is 'surplus' to the diagnostic process. USC Norris Comprehensive Cancer Center has a NCI funded core tissues bank for the accrual, banking and distribution of both normal and pathologic tissues. The analytes to be studied are listed in Table 4 in preliminary form, but are subject to change, addition or deletion, based upon the cell line block studies described in Part I. The goal is to employ the validated protein and RNA panels of internal reference standards derived in cell line FFPE blocks to tonsil (and then other normal tissues), in order to validate these same methods anew on tissues. The goal is perhaps best illustrated by example—can the cytoplasmic vimentin present in a population of ubiquitous cells (such as lymphocytes) be employed as an internal reference standard? Is it present in sufficiently constant amounts? Is the vimentin loss following FFPE and AR sufficiently consistent, that it can serve across routine FFPE methods among different labs and different tissues? Does the loss of vimentin relate in any constant way to any other test proteins? We propose that by the careful validation procedures described it will be possible in the R33 to ask and answer these questions for a wide variety of clinically useful analytes (proteins and RNA). If we can do that the world of IHC, ISH and indeed surgical pathology will have changed.

Specific Aim 5—to examine abnormal pathologic tissues, using the panels of internal reference standards established for protein in FFPE cell line blocks and FFPE normal human tissue (Aims 1 and 3), to test for the ability to quantify protein analytes by calculation of the amount of analyte per cell using correction and relative loss factors (as described for cell line blocks in Part I, Specific Aim 5 and Part II, Aim 1). Double IHC stains will be employed, to allow comparison of the stain reaction for the reference analyte (per cell) with the staining reaction for the test analyte (per cell), using quantitative spectral imaging and image analysis.

Specific Aim 6—to examine abnormal pathologic tissues, using the panels of internal reference standards established for RNA in FFPE cell line blocks and FFPE normal human tissue (Aims 1 and 4), to test for the ability to quantify protein analytes by calculation of the amount of analyte per cell using correction and relative loss factors (as described for cell line blocks in Part I, Specific Aim 5 and Part II, Aim 1). Double ISH stains will be employed, to allow comparison of the stain reaction for the reference analyte (per cell) with the staining reaction for the test analyte (per cell), using quantitative spectral imaging and image analysis. For this purpose the chromogenic/gold peT-ISH method developed under Aim 3 will be employed.

For both Aims 5 and 6 the experimental design and methodology recapitulate the R21 phase (Tables 3 and 4), and the studies of normal human tissues (Part II, Aims 3 and 4—Table 5). With respect to pathologic tissues, additional challenges exist and there are additional questions to ask, and answer. It is anticipated that most pathologic tissues will contain common cell types (lymphocytes, fibroblasts, endothelial cells, often epithelial cells) that in turn express one or more of the reference standard analytes (proteins and RNA). It will be necessary to establish through experimentation that these analytes are present and that their expression and behavior following FFPE is consistent (i.e., stable correction factor) so as to allow their use as internal standards. A larger challenge will be that many of the 'test' analytes will be uncommon in distribution, or even unique to particular tumor types, or to particular cells within the tumor. By the methods described in Part II, Aim 1, it will be necessary to determine, again experimentally, that consistent relationships exist between and test analyte (protein or RNA) and one or more of the established internal reference standards (i.e., stable relative loss factor). It should be emphasized that the investigators do recognize that the number of protein and RNA analytes that have been discovered, and will continue to be discovered, is very large, and that the scope of this grant is to establish the feasibility of this approach and to set up methods and protocols for determining the relevant correction and relative loss factors for new internal standards and for new test analytes. It is proposed to share data ongoing with NIST (the National Institute of Standards and Technology, 100 Bureau Drive, Gaithersburg, Md.) and seek their guidance in Aims 5 and 6 as to procedures for qualifying candidate reference analytes as NIST Certified Values (strictest criteria) or NIST Reference Values (the most likely outcome for analyses that are method dependent). The eventual scope of this work extends beyond this study in resources and expertise and for this reason Dr. P. Barker of NIST has already been invited and has accepted a role of advisor and consultant in this project. Once the principles and methods are established, the generation of this data could become a standard part of the discovery and descriptive process of potential new markers, and could be monitored and managed by, for example, NIST.

Cell lines will be used in this study, and these are processed into formalin paraffin blocks. Formalin paraffin blocks of normal and pathologic human tissues will be used. These will be obtained from the Norris Cancer Center Tumor Tissues bank (of anonymized specimens) or from the archival formalin paraffin blocks of the Pathology Department at the Norris Cancer Hospital. All such blocks will be obtained either at completion of the diagnostic process or at the time of expiry of such blocks when they would otherwise be discarded. All material will be rendered anonymous by the staff before release to the study. No additional tissues will be taken and there is no risk to patients.

The study may help us to develop improved methods for cancer diagnosis and prognosis by means of standardized immunohistochemical and in situ hybridization methods applied to formalin paraffin sections. This is an area of serious deficiency today, as directly reference in the NCI RFA to which this application responds. Patient care and entry data to clinical trials would be greatly advantaged.

References

[1] Taylor, C. R. and Cote, R. J. Immunomicroscopy. A Diagnostic Tool for the Surgical Pathologist, 3rd edition. Philadelphia: Elsevier Saunders, 2005.

[2] Taylor, C. R. and Burns, J. The demonstration of plasma cells and other immunoglobulin containing cells in formalin-fixed, paraffin-embedded tissues using peroxidase labeled antibody, J. Clin. Pathol. 27: 14-20, 1974.

[3] Taylor, C. R. The nature of Reed-Sternberg cells and other malignant "reticulum" cells, Lancet. 2(7884): 802-807, 1974.

[4] Taylor, C. R. A history of the Reed-Sternberg cell, Biomedicine. 28: 196, 1978.

[5] Taylor, C. R. Immunohistologic studies of lymphomas: New methodology yields new information and poses new problems, J. Histochem. Cytochem. 27: 1189-1191, 1979.

[6] Taylor, C. R. Immunohistologic studies of lymphoma: Past, present and future. J. Histochem. Cytochem. 28: 777-787, 1980.

[7] Taylor, C. R. and Kledzik, G. Immunohistologic techniques in surgical pathology. A spectrum of new special stains, Hum. Pathol. 12: 590-596, 1981.

[8] Shi, S. R., Key, M. E., and Kalra, K. L. Antigen retrieval in formalin-fixed, paraffin-embedded tissues: an enhancement method for immunohistochemical staining based on microwave oven heating of tissue sections, J. Histochem. Cytochem. 39: 741-748, 1991.

[9] Shi, S. R., Cote, C., Kalra, K. L., Taylor, C. R., and Tandon, A. K. A technique for retrieving antigens in formalin-fixed, routinely acid-decalcified, celloidin-embedded human temporal bone sections for immunohistochemistry, J. Histochem. Cytochem. 40: 787-792, 1992.

[10] Shi, S. R., Chaiwun, B., Young, L., Cote, R. J., and Taylor, C. R. Antigen retrieval technique utilizing citrate buffer or urea solution for immunohistochemical demonstration of androgen receptor in formalin-fixed paraffin sections, J. Histochem. Cytochem. 41: 1599-1604, 1993.

[11] Shi, S. R., Chaiwun, B., Young, L., Imam, A., Cote, R. J., and Taylor, C. R. Antigen retrieval using pH 3.5 glycine-HCl buffer or urea solution for immunohistochemical localization of Ki-67, Biotech. Histochem. 69: 213-215, 1994.

[12] Shi, S.-R., Gu, J., Kalra, K. L., Chen, T., Cote, R. J., and Taylor, C. R. Antigen retrieval technique: a novel approach to immunohistochemistry on routinely processed tissue sections, Cell Vision. 2: 6-22, 1995.

[13] Shi, S. R., Cote, R. J., Young, L., Imam, S. A., and Taylor, C. R. Use of pH 9.5 Tris-HCl buffer containing 5% urea for antigen retrieval immunohistochemistry, Biotech. Histochem. 71: 190-196, 1996.

[14] Shi, S.-R., Cote, R. J., Wu, L., Liu, C., Datar, R., Shi, Y., Liu, D., Lim, H., and Taylor, C. R. DNA extraction from archival formalin-fixed, paraffin-embedded tissue sections based on the antigen retrieval principle: heating under the influence of pH, J. Histochem. Cytochem. 50: 1005-1011, 2002.

[15] Shi, S.-R., Datar, R., Liu, C., Wu, L., Zhang, Z., Cote, R. J., and Taylor, C. R. DNA extraction from archival formalin-fixed, paraffin-embedded tissues: heat-induced retrieval in alkaline solution, Histochem. Cell Biol. 122: 211-218, 2004.

[16] Taylor, C. R. Report of the Immunohistochemistry Steering Committee of the Biologixal Stain Commission. "Proposed Format: Package Insert for Immunohistochemistry Products", Biotech. Histochem. 67: 323-338, 1992.

[17] Taylor, C. R., Shi, S. R., Chaiwun, B., Young, L., Imam, S. A., and Cote, R. J. Strategies for improving the immunohistochemical staining of various intranuclear prognostic markers in formalin-paraffin sections: androgen receptor, estrogen receptor, progesterone receptor, p53 protein, proliferating cell nuclear antigen, and Ki-67 antigen revealed by antigen retrieval techniques [see comments], Hum. Pathol. 25: 263-270, 1994.

[18] Taylor, C. R. The current role of immunohistochemistry in diagnostic pathology, Advan. Pathol. Lab. Med. 7: 59-105, 1994.

[19] Taylor, C. R., Shi, S.-R., Chaiwun, B., Young, L., Imam, S. A., and Cote, R. J. Correspondence. Standardization and reproducibility in diagnostic immunohistochemistry, Hum. Pathol. 25: 1107-1109, 1994.

[20] Battifora, H. Quality assurance issues in immunohistochemistry, J. Histotechnol. 22: 169-175, 1999.

[21] Bhan, A. K. Chapter 38, Immunoperoxidase, 2nd edition, p. 711-723. New York: Raven Press, 1995.

[22] Colvin, R. B., Bhan, A. K., and McCluskey, R. T. Diagnostic Immunopathology, 2nd edition. New York: Raven Press, 1995.

[23] Dapson, R. W. Fixation for the 1990's: a review of needs and accomplishments, Biotech. Histochem. 68: 75-82, 1993.

[24] DeLellis, R. A., Sternberger, L. A., Mann, R. B., Banks, P. M., and Nakane, P. K. Immunoperoxidase techniques in diagnostic pathology. Report of a workshop sponsored by the National Cancer Institute, Am. J. Clin. Pathol. 71: 483-488, 1979.

[25] DeLellis, R. A. Advances in Immunohistochemistry. p. 1-45. New York: Raven Press, 1988.

[26] Elias, J. M. Immunohistopathology: A Practical Approach to Diagnosis, 1st edition, p. 1-9. Chicago: ASCP Press, 1990.

[27] Elias, J. M. Commentary: Immunohistochemistry: a brief historical perspective. In: S.-R. Shi, J. Gu, and C. R. Taylor (eds.), Antigen Retrieval Techniques: Immunohistochemistry and Molecular Morphology, pp. 7-13, 2000.

[28] Larsson, L.-I. Immunocytochemistry: Theory and Practice, p. 41-170. Boca Raton, Fla.: CRC Press, 1988.

[29] Taylor, C. R. Quality assurance and standardization in immunohistochemistry. A proposal for the annual meeting of the Biological Stain Commission., Biotech. Histochem. 67.110-117, 1992.

[30] Taylor, C. R. An exaltation of experts: concerted efforts in the standardization of immunohistochemistry, Hum. Pathol. 25: 2-11, 1994.

[31] Taylor, C. FDA issues final rule for classification of reclassification of immunochemistry reagents and kits, Am. J. Clin. Pathol. 111: 443-444, 1999.

[32] Rhodes, A., Jasani, B., Balaton, A. J., and Miller, K. D. Immunohistochemical demonstration of oestrogen and progesterone receptors: correlation of standards achieved on in house tumours with that achieved on external quality assessment material in over 150 laboratories from 26 countries, J. Clin. Pathol. 53: 292-301, 2000.

(33) Rhodes, A., Jasani, B., Balaton, A. J., Barnes, D. M., Anderson, E., Bobrow, L. G., and Miller, K. D. Study of interlaboratory reliability and reproducibility of estrogen and progesterone receptor assays in Europe: documentation of poor reliability and identification of insufficient microwave antigen retrieval time as a major contributory element of unreliable assays, Am. J. Clin. Pathol. 115: 44-58, 2001.

(34) Shi, S.-R., Liu, C., Balgley, B. M., Lee, C., and Taylor, C. R. Protein extraction from formalin-fixed, paraffin-embedded tissue sections: quality evaluation by mass spectrometry, J. Histochem. Cytochem. JHC exPress, DOI:10.1369/jhc.5B6851.2006.

(35) Capodieci, P., Donovan, M., Buchinsky, H., Jeffers, Y., Cordon-Cardo, C., W., G., J., E., M., S. S., and Singer, R. H. Gene expression profiling in single cells within tissue, Nature Methods. 2: 663-665, 2005.

(36) Taylor, C. R., Shi, S.-R., and Cote, R. J. Antigen retrieval for immunohistochemistry. Status and need for greater standardization, Appl. Immunohistochem. 4: 144-166, 1996.

(37) Shi, S. R., Cote, R. J., and Taylor, C. R. Antigen retrieval immunohistochemistry: past, present, and future, J. Histochem. Cytochem. 45: 327-343, 1997.

(38) Shi, S.-R., Cote, R. J., Young, L. L., and Taylor, C. R. Antigen retrieval immunohistochemistry: practice and development, J. Histotechnol. 20: 145-154, 1997.

(39) Shi, Y., Li, G.-D., and Liu, W.-P. Recent advances of the antigen retrieval technique, Linchuang yu Shiyan Binglixue Zazhi (J. Clin. Exp. Pathol.). 13: 265-267, 1997.

(40) Shi, S. R., Cote, R. J., and Taylor, C. R. Antigen retrieval immunohistochemistry used for routinely processed celloidin-embedded human temporal bone sections: standardization and development, Auris Nasus Larynx. 25: 425-443, 1998.

(41) Shi, S.-R., Cote, R. J., and Taylor, C. R. Standardization and further development of antigen retrieval immunohistochemistry: strategies and future goals, J. Histotechnol. 22: 177-192, 1999.

(42) Shi, S.-R., Cote, R. J., Shi, Y., and Taylor, C. R. Antigen retrieval technique. In: S.-R. Shi, J. Gu, and C. R. Taylor (eds.), Antigen Retrieval Techniques: Immunohistochemistry and Molecular Morphology, 1st. edition. Natick, Mass.: Eaton Publishing, 2000.

(43) Boon, M. E. and Kok, L. P. Breakthrough in pathology due to antigen retrieval, Mal. J. Med. Lab. Sci. 12: 1-9, 1995.

(44) Brown, C. Antigen retrieval methods for immunohistochemistry, Toxicol. Pathol. 26: 830-831, 1998.

(45) Cuevas, E. C., Bateman, A. C., Wilkins, B. S., Johnson, P. A., Williams, J. H., Lee, A. H., Jones, D. B., and Wright, D. H. Microwave antigen retrieval in immunocytochemistry: a study of 80 antibodies, J. Clin. Pathol. 47: 448-452, 1994.

(46) Evers, P., Uylings, H. B., and Suurmeijer, A. J. Antigen retrieval in formaldehyde-fixed human brain tissue, Methods. 15: 133-140, 1998.

(47) Gown, A. M., de Wever, N., and Battifora, H. Microwave-based antigenic unmasking. A revolutionary new technique for routine immunohistochemistry, Appl. Immunohistochem. 1: 256-266, 1993.

(48) Gown, A. M. Unmasking the mysteries of antigen or epitope retrieval and formalin fixation, Am. J. Clin. Pathol. 121: 172-174, 2004.

(49) Grabau, K. A., Nielsen, O., Hansen, S., Nielsen, M. M., Lankholm, A. V., Knoop, A., and Pfeiffer, P. Influence of storage temperature and high-temperature antigen retrieval buffers on results of immunohistochemical staining in sections stored for long periods, Appl. Immunohistochem. 6: 209-213, 1998.

(50) Hopwood, D. Epitope retrieval—survey and prospect, Eur. J. Morphol. 32: 317-324, 1994.

(51) Krenacs, L., Krenacs, T., and Raffeld, M. Antigen retrieval for immunohistochemical reactions in routinely processed paraffin sections, Methods Mol. Biol. 115: 85-93, 1999.

(52) Leong, A. S. Microwaves in diagnostic immunohistochemistry, Eur. J. Morphol. 34: 381-383, 1996.

(53) Leong, A. S.-Y., Lee, E. S., Yin, H., Kear, M., Haffajee, Z., and Pepperall, D. Superheating antigen retrieval, Appl. Immunohistochem. Mol. Morphol. (AIMM). 10: 263-268, 2002.

(54) Miller, R. T. and Estran, C. Heat-induced epitope retrieval with a pressure cooker-suggestions for optimal use, Appl. Immunohistochem. 3: 190-193, 1995.

(55) Miller, R. T., Swanson, P. E., and Wick, M. R. Fixation and epitope retrieval in diagnostic immunohistochemistry: a concise review with practical considerations, Appl. Immunohistochem. Mol. Morphol. (AIMM). 8: 228-235, 2000.

(56) Newman, S. J. and Gentleman, S. M. Microwave antigen retrieval in formaldehyde-fixed human brain tissue, Methods Mol. Biol. 72: 145-152, 1997.

(57) O'Leary, T. J. Standardization in immunohistochemistry, Appl. Immunohistochem. Mol. Morphol. (AIMM). 9: 3-8, 2001.

(58) Pileri, S. A., Roncador, G., Ceccarelli, C., Piccioli, M., Briskomatis, A., Sabattini, E., Ascani, S., Santini, D., Piccaluga, P. P., Leone, O., Damiani, S., Ercolessi, C., Sandri, F., Pieri, F., Leoncini, L., and Falini, B. Antigen retrieval techniques in immunohistochemistry: comparison of different methods, J. Pathol. 183: 116-123, 1997.

(59) Reynolds, G. M., Young, F. I., Young, J. A., Williams, A., and Rowlands, D. C. Microwave oven antigen retrieval applied to the immunostaining of cytopathology specimens, Cytopathology. 5: 345-358, 1994.

(60) Rocken, C. and Roessner, A. An evaluation of antigen retrieval procedures for immunoelectron microscopic classification of amyloid deposits, J. Histochem. Cytochem. 47: 1385-1394, 1999.

(61) Stirling, J. W. and Graff, P. S. Antigen unmasking for immunoelectron microscopy: labeling is improved by treating with sodium ethoxide or sodium metaperiodate, then heating on retrieval medium, J. Histochem. Cytochem. 43: 115-123, 1995.

(62) Swanson, P. E. Microwave antigen retrieval in citrate buffer, Lab. Med. 25: 520-522, 1994.

(63) Werner, M., Von Wasielewski, R., and Komminoth, P. Antigen retrieval, signal amplification and intensification in immunohistochemistry, Histochem. Cell Biol. 105: 253-260, 1996.

(64) Ingram, M., Techy, G. B., Saroufeem, R., Yazan, O., Narayan, K. S., Goodwin, T. J., and Spaulding, G. F. Three-dimensional growth patterns of various human tumor cell lines in simulated microgravity of a NASA bioreactor, In Vitro Cellular & Developmental Biology. Animal. 33: 459-466, 1997.

(65) Shi, S.-R., Liu, C., Perez, J., and Taylor, C. R. Protein-Embedding Technique: A Potential Approach to Standardization of Immunohistochemistry for Formalin-Fixed, Paraffin-Embedded Tissue Sections, J. Histochem. Cytochem. 53: 1167-1170, 2005.

(66) Shi, S.-R., Gu, J., Cote, R. J., and Taylor, C. R. Chapter 16. Standardization of routine immunohistochemistry: where to begin? In: S.-R. Shi, J. Gu, and C. R. Taylor (eds.), Antigen Retrieval Technique: Immunohistochemistry and Molecular Morphology, First edition, pp. 255-272. Natick, Mass.: Eaton Publishing, 2000.

[67] Risio, M. Methodological aspects of using immunohistochemical cell proliferation biomarkers in colorectal carcinoma chemoprevention, J. Cell Biochem. Suppl. 19: 61-67, 1994.

[68] Riera, J., Simpson, J. F., Tamayo, R., and Battifora, H. Use of cultured cells as a control for quantitative immunocytochemical analysis of estrogen receptor in breast cancer. The Quicgel method, Am. J. Clin. Pathol. 111: 329-335, 1999.

[69] Mighell, A. J., Hume, W. J., and Robinson, P. A. An overview of the complexities and subtleties of immunohistochemistry, Oral Dis. 4: 217-23, 1998.

[70] Sompuram, S. R., Kodela, V., Zhang, K., Ramanathan, H., Radcliffe, G., Falb, P., and Bogen, S. A. A novel quality control slide for quantitative immunohistochemistry testing, J. Histochem. Cytochem. 50: 1425-1434, 2002.

[71] Sompuram, S. R., Kodela, V., Ramanathan, H., Wescott, C., Radcliffe, G., and Bogen, S. A. Synthetic peptides identified from phage-displayed combinatorial libraries as immunodiagnostic assay surrogate quality-control targets, Clin. Chem. 48: 410-420, 2002.

[72] Battifora, H. Assessment of antigen damage in immunohistochemistry. The vimentin internal control, Am. J. Clin. Pathol. 96: 669-671, 1991.

[73] Shi, S.-R., Cote, R. J., Chaiwun, B., Young, L. L., Shi, Y., Hawes, D., T., C., and Taylor, C. R. Standardization of immunohistochemistry based on antigen retrieval technique for routine formalin-fixed tissue sections, Appl. Immunohistochem. 6: 89-96, 1998.

[74] Rhodes, A., Jasani, B., Andersion, E., Dodson, A. R., and Balaton, A. J. Evaluation of HER-2/neu Immunohistochemical Assay Sensitivity and Scoring on Formalin-Fixed and Paraffin-Processed Cell Lines and Breast Tumors, Am. J. Clin. Pathol. 118: 408-417, 2002.

[75] Jacobs, T. W., Gown, A. M., Yaziji, H., A M., B., and Schnitt, S. J. HER-2/neu Protein Expression in Breast Cancer Evaluated by Immunohistochemistry, Am. J. Clin. Pathol. 113: 251-258, 2000.

[76] Lambkin, H. A., Dunne, P., and McCarthy, P. M. Standardization of estrogen-receptor analysis by immunohistochemistry—an assessment of interlaboratory performance in Ireland, Appl. Immunohistochem. 6: 103-107, 1998.

[77] Willey, J. C., Crawford, E. L., Jackson, C. M., Weaver, D. A., Hoban, J. C., Khuder, S. A., and DeMuth, J. P. Expression measurement of many genes simultaneously by quantitative RT-PCR using standardized mixtures of competitive templates, Am. J. Res. Cell Mol. Biol. 19: 16-24, 1998.

[78a] Pagliarulo, V., George, B., Beil, S. J., Groshen, S., Laird, P. W., Cai, J., Willey, J., Cote, R. J., and Datar, R. H. Sensitivity and reproducibility of standardized-competitive RT-PCR for transcript quantification and its comparison with real time RT-PCR, Mol. Cancer. 3: 5, 2004.

[78b] Mitra A P, Almal A A, George B, Fry D W, Lenehan P F, Pagliarulo V, Cote, R J, Datar, R H, Worzel W P. The use of genetic programming in the analysis of quantitative gene expression profile for nodal status in bladder cancer. BMC Cancer. 6: 159, 2006.

[79] Leong, A. S.-Y. Immunostaining of Cytologic Preparations: A Review of Technical Problems, Appl. Immunohistochem. Mol. Morphol. 7: 214-220, 1999.

[80] Grizzle, W. E., Myers, R. B., and Oelschlager, D. K. Prognostic biomarkers in breast cancer: factors affecting immunohistochemical evaluation, Breast. 1: 243-250, 1995.

[81] Zu, Y., Steinberg, S. M., Campo, E., Hans, C. P., Weisenburger, D. D., Braziel, R. M., Delabie, J., Gascoyne, R. D., Muller-Hermlink, K., Pittaluga, S., Raffeld, M., Chan, W. C., and Jaffe, E. S. Validation of tissue microarray immunohistochemistry staining and interpretation in diffuse large B-cell lymphoma, Leukemia & Lymphoma. 46: 693-701, 2005.

[82] Downs-Kelly, E., Yoder, B. J., Stoler, M., Tubbs, R. R., Skacel, M., Grogan, T., Roche, P., and Hicks, D. G. The influence of polysomy 17 on HER2 gene and protein expression in adenocarcinoma of the breast: a fluorescent in situ hybridization, immunohistochemical, and isotopic mRNA in situ hybridization study, Am. J. Surg. Pathol. 29: 1221-1227, 2005.

[83] Pusztaszeri, M., Chaubert, P., Seelentag, W., and Bosman, F. T. Immunohistochemical Expression of Endothelial MARKERS CD31, CD34, von Willebrand Factor, and Fli-1 in Normal Human Tissues, JHC exPRESS doi: 10.1369/jhc.4A6514.2005, 2005.

[84] Shi, S. R., Cote, R. J., Yang, C., Chen, C., Xu, H. J., Benedict, W. F., and Taylor, C. R. Development of an optimal protocol for antigen retrieval: a 'test battery' approach exemplified with reference to the staining of retinoblastoma protein (pRB) in formalin-fixed paraffin sections, J. Pathol. 179: 347-352, 1996.

[85] Shi, S.-R., Gu, J., Kalra, K. L., Chen, T., Cote, R. J., and Taylor, C. R. Chapter 1. Antigen retrieval technique: a novel approach to immunohistochemistry on routinely processed tissue sections. In: J. Gu (ed.) Analytical Morphology, Theory, Applications & Protocols, 1st edition, pp. 1-40. Natick, Mass., USA: Eaton Publishing Co., 1997.

[86] Berger, A. J., Camp, R. L., Divito, K. A., Kluger, H. M., Halaban, R., and Rimm, D. L. Automated quantitative analysis of HDM2 expression in malignant melanoma shows association with early-stage disease and improved outcome, Cancer Res. 64: 8767-8772, 2004.

[87] Kaur, R. and Raje, M. A solid-phase method for evaluation of gold conjugate used in quantitative detection of antigen by immunogold-labeling electron microscopy, J. Immunol. Methods. 279: 33-40, 2003.

[88] Ramandeepa, Dikshita, K. L., and Rajea, M. Optimization of Immunogold Labeling TEM: An ELISA-based Method for Rapid and Convenient Simulation of Processing Conditions for Quantitative Detection of Antigen, J. Histochem. Cytochem. 49: 355-368, 2001.

[89] Petersen, B. L., Sorensen, M. C., Pedersen, S., and Rasmussen, M. Fluorescence in situ hybridization on formalin-fixed and paraffin-embedded tissue: optimizing the method., Appl. Immunohistochem. Mol. Morphol. 12: 259-265, 2004.

[90] Robinsona, J. M., Takizawab, T., and D., V. D. Enhanced Labeling Efficiency Using Ultrasmall Immunogold Probes: Immunocytochemistry, J. Histochem. Cytochem. 48:487-492, 2000.

[91] Tubbs, R., Pettay, J., Skacel, M., Powell, R., Stoler, M., Roche, P., and Hainfeld, J. Gold-facilitated in situ hybridization: a bright-field autometallographic alternative to fluorescence in situ hybridization for detection of Her-2/neu gene amplification, Am. J. Pathol. 160: 1589-1595, 2002.

[92] Chaiwun, B., Shi, S.-R., Cote, R. J., and Taylor, C. R. Chapter 2. Major factors influencing the effectiveness of antigen retrieval immunohistochemistry. In: S.-R. Shi, J. Gu, and C. R. Taylor (eds.), Antigen Retrieval Techniques: Immunohistochemistry and Molecular Morphology, pp. 41-53. Natick, Mass.: Eaton Publishing, 2000.

(93) Shi, S. R., Imam, S. A., Young, L., Cote, R. J., and Taylor, C. R. Antigen retrieval immunohistochemistry under the influence of pH using monoclonal antibodies, J. Histochem. Cytochem. 43: 193-201, 1995.

(94) Taylor, C. R. Quantitative Internal Reference Standards for Immunohistochemistry. The measurement of quantity by weight. Appl Immunohistochem Mol Morph. 14: 253-259, 2006.

(95) Taylor, C. R. and Levenson, R. M. Quantification of immunohistochemistry—issues concerning methods, utility and semi-quantitative assessment. Expert Opinion. J Histopath (in press) 2006.

(96) Shi, S. R., Cheng, L and Taylor, C. R. Standardization of Immunohistochemistry for Formalin-Fixed Paraffin-Embedded Tissue Sections Based on the Antigen Retrieval technique; from Eperiments to Hypothesis. J Histochem Cyto Chem (in press) 2006.

(97) Taylor, C. R. Standardization in Immunohistochemistry: the role of antigen retrieval in Molecular Morphology. Biotechnic and Histochem. 8:3-12, 2006.

Example IV

The Key Message Underlying the ASCO/CAP TASK-Force Guideline Recommendations for Her2 Testing Background:

The recently released ASCO/CAP Task-Force Guideline Recommendations, published simultaneously in the Journal of Clinical Oncology (1) and Archives of Pathology and Laboratory Medicine (2), address issues relevant to improving the accuracy of HER2 testing in breast cancer. These recommendations represent a serious effort by the CAP, providing concrete and practical solutions to real problems in HER2 testing. Significant components of this 47-page document can be summarized as follows:

1. These recommendations will become mandatory requirements on Jan. 1, 2008 to all CAP-certified laboratories.

2. Testing algorithms were established for both IHC and FISH. The report includes a statement recognizing that HER2 "test results represent a continuous rather than a categoric variable", i.e., these results simply can no longer be reported as binary. The Task Force, for the first time, recognizes that an "equivocal" gray zone exists, containing tumors with borderline scores of both IHC and FISH assays. Equivocal IHC samples (2+ score) must be confirmed by FISH analysis of the sample. Equivocal FISH samples are to be confirmed by counting additional cells or repeating the FISH test. If the FISH results remain equivocal, confirmatory IHC testing should be performed. "Equivocal" for FISH is defined by the Task Force as "moderate or weak complete staining in 10-30% of tumor cells or complete, non-uniform staining in >10% of cells.

3. By 2008, all CAP-accredited pathology laboratories performing HER2 testing must have validated their HER2 assay against either a different validated in-house assay or a validated similar assay done by another laboratory. A minimum of 25 invasive breast cancers is required. Practically speaking, if a pathology laboratory offers HER2 testing by IHC, it must validate its assay using results from another laboratory that has an established, clinically validated IHC assay. The same requirement applies for laboratories that offer both IHC and FISH assays, neither of which is clinically validated; a laboratory can only validate an assay internally, against another assay, if the other assay is itself clinically validated.

4. Importantly the guidelines also include a requirement that pathology laboratories must ensure that all breast excision specimens subject to HER2 testing are fixed in 10% neutral buffered formalin for 6-48 hours, and that core biopsies are fixed for at least 1 hour. Any and all alternative fixatives must be validated to ensure satisfactory "performance against the results of testing of the same samples fixed also in buffered formalin and tested with the identical HER2 assay, and concordance in this situation must also be 95%".

5. The Task Force also raised the bar for the positive cutoff for the percentage of cells with 3+ score, from the previously FDA-approved 10% cutoff to a new 30% cutoff. The underlying rationale is that "very rarely . . . invasive tumors can show intense [3+], complete membrane staining of 30% or fewer tumor cells".

6. Also for the first time, the Task Force accepts the fact that there is no gold standard assay for HER2 in breast cancer, not FISH and not IHC. While FISH technique has been viewed as a gold standard by some, evidence-based data do not confirm that notion.

7. Intrinsic to these guidelines is the acceptance that "no assay currently available is perfectly accurate to identify all patients expected to benefit or not from anti-HER2 therapy". In other words, when we measure and achieve 95% concordance between two assays, we are not measuring the predictive value of each assay; merely that they are concordant.

8. New test rejection criteria were also established, and summarized in Tables 1 and 2, for IHC and FISH respectively.

9. These recommendations will undoubtedly undergo periodic reviews by the Task Force with expected revisions.

10. While the guidelines represent an important 'leap forward', some unresolved issues remain.

Items Requiring Further Clarification:

The guidelines are for the most part specific and of real practical value. Nonetheless, in the opinion of the authors points for clarification include:

1. Test validation must be done "before offering the test clinically". In reality, a good fraction of pathology laboratories in the US have been offering HER2 testing for clinical use prior to publication of these guidelines. The Task Force did not specify any concrete steps for these labs to validate the test retroactively; possibly the best that can be achieved is for all laboratories intending to offer either IHC or FISH HER2 assays to be in compliance by January 2008. The alternative is to cease testing.

2. The Task Force does not specify how the competency of the pathologists interpreting HER2 testing should be measured and monitored, particularly with regard to the reproducibility of scoring by both the IHC and FISH methods. Will an expanded CAP external evaluation program be available to meet this need? The UK NEQAS model (3) surely is the best available, requiring central consensus value reading of specific sample sections by experienced pathologists. Such a system may be hard to replicate in the larger diverse environment of the US, and who will pay for the costs of achieving this new better assay? Absent appropriate reimbursement success may be long coming.

3. There is no practical strategy in place for ensuring that specimens have been properly fixed; a minimum requirement would seem to be that the times of placement and removal of the tissue/biopsy into and from 10% formalin should be recorded (vide infra).

4. Then there is the practical problem in studies, and especially in clinical trials, of integrating the results of the 'new improved' guideline compliant test result, with the old. Going forward the decision is made for us by the mandate; but uncertainties will exist with regard to patients currently on, or not on, Herceptin therapy, especially those with equivocal tumors, and simple repeat testing will not necessarily solve the problem in the face on unknown tissue fixation conditions.

Items Requiring Modification:

It is agreed that most breast cancers that are positive (3+) for HER2 over expression by IHC, give a quite uniform positive result across the tumor section, and in practice it is uncommon that the positive signal is patchy, or observed in <50% of cells (4). Nonetheless tumors do exist, albeit rarely, where there is clear and definite positive reaction (both by IHC and FISH) in a fraction ('clone') of tumor cells that overall averages much less than 30%. By the proposed guidelines, these tumors would be classified as negative. Most tumor biologists would concur that the HER2 positive tumor clone is likely to be more aggressive (than the HER2 negative component) and will ultimately dictate the biologic and clinical behavior of the tumor. Further consideration should be given as to whether such focally 3+ tumors should be classified as at least as equivocal, if not as positive.

The guidelines correctly imposed stringent requirements for the 6-48 hour-fixation window on excision specimens (lumpectomies, mastectomies); however, based on these guidelines recommendations, core biopsies require only a minimum of one-hour fixation. While formalin infiltration through the entire core biopsy may be effected within 1 hour, formalin is a very slow fixative and infiltration is not equivalent to fixation (4). We believe that the minimum fixation-time requirements for core biopsies should be as much as 6 hours, instead of one hour and that data exist to support this contention (5). Certainly we are not aware of convincing data that one hour fixation is sufficient. Ensuring the propriety of this fixation guideline is particularly important given that an increasing number of pathology laboratories are already performing HER2 IHC testing on the core biopsy rather than the excision specimen. It may be that a 6 hour fixation will preclude meeting the 'requirements' of our clinical colleagues in some situations; however, in the context of these new guidelines, reliable performance should govern practice, rather than expediency. Some have argued, with justification, that pressure from our clinical colleagues for the patient's results 'yesterday', has driven the use of abbreviated and unproven 'rapid fixation' protocols. If so, it is remarkable that now these same clinical colleagues are the major driving force behind recognition of the overriding necessity for improving the reliability of the HER2 assays, and we should thank them for it. In the final analysis the patient is likely to benefit from the right result, rather than the rapid one, and informed of the choice the patient undoubtedly would tell us that we need 'to do it right'.

Conclusion:

We applaud and endorse the work of the ASCO/CAP Task Force. It is long awaited, and it is here; so we all need to deal with it. Perhaps the two items that have the biggest impact on pathology laboratories overall are tissue handling requirement and test monitoring requirements. Now the largest regulatory body in US pathology is finally recognizing that we, as pathologists, have been inflicting unknown and unknowable damage on our specimens by not following proper fixation procedures. There are sufficient data to confirm that inadequate tissue fixation is responsible in large part for many of the reportedly false-negative results in hormone receptors testing in breast cancer (6, 7).

But HER2 is just the beginning. The growing list of 'tests' of critical prognostic/predictive markers that are being introduced into anatomic pathology makes this task of proper tissue fixation one of the most important ingredients of standardizing these tests, and represents a first essential step in converting these 'stains' into reliable assays. The high standards of quality control testing that have long been employed in the clinical pathology laboratory must be applied to tests that we perform across the hallway in the anatomic pathology laboratory. After all, isn't the IHC test a slightly modified version of the ELISA test? (8). For the results of any prognostic/predictive test to be clinically meaningful, rigorous quality control measures must be applied and followed, and we cannot avoid beginning at the beginning with proper specimen acquisition and handling protocols. The good news for anatomic pathology laboratories is we do know what needs to be done, and these measures aren't that difficult to implement.

References

1. Wolff A C, Hammond E H, Schwartz J N, et al. American Society of Clinical Oncology/College of American Pathologists Guideline Recommendations for Human Epidermal Growth Factor Receptor 2 Testing in Breast Cancer. J Clin Oncol 2007; 25(1):118-145.
2. Wolff A C, Hammond E H, Schwartz J N, et al. American Society of Clinical Oncology/College of American Pathologists Guideline Recommendations for Human Epidermal Growth Factor Receptor 2 Testing in Breast Cancer. Arch Pathol Lab Med 2007; 131(1):18-43.
3. Rhodes A, Jasani B, Anderson E, Dodson A R, Balaton A J. Evaluation of HER-2/neu Immunohistochemistry Assay Sensitivity and scoring on formalin-fixed and paraffin-processed cell lines and breast tumors: a comparative study involving results from laboratories in 21 countries. Am J Clin Pathol 2002; 118(3):408-417.
4. Fox C H, et al. Formaldehyde Fixation. J Histochem Cytochem 1985; 33:845-853.
5. Goldstein N S, Ferkowicz M, Odish E, et al. Minimum formalin fixation time for consistent estrogen receptor immunohistochemical staining of invasive breast carcinoma. Am J Clin Pathol. 2003; 120(1), 86-92.
6. Nadji M, Gomez-Fernandez C, Ganjei-Azar P, et al. Immunohistochemistry of estrogen and progesterone receptors reconsidered: experience with 5,993 breast cancers. Am J Clin Pathol 2005; 123(1):21-27.
7. Yaziji H, Goldstein L C, Barry T S, et al. HER-2 Testing in Breast Cancer Using Parallel Tissue-Based Methods. JAMA 2004; 29(16):1972-1977.
8. Taylor C R, Quantifiable Internal Reference Standards for Immunohistochemistry. The Measurement of Quantity by Weight. Appl Immunohistochem Mol Morphology 2007; 14. 253-259.

Example V

Over several decades immunohistochemistry has evolved from a methodologic curiosity, of occasional research interest, to a technique that is in widespread use in surgical pathology, and is considered to be essential in many areas of cancer diagnosis and classification. Today, there is a resurgent interest in assuring the reproducibility of the method, even to the point of upgrading it from a "stain" to a tissue-based "immunologic assay." If accomplished, this change would make possible true quantification of analytes in tissue sections, analogous to the use of the enyzyme-linked immunosorbent assay method in the clinical laboratory, which employs essentially the same reagents and similar principles, but is subject to much more rigorous control at all levels. (2,3)

Immunohistochemistry gives a tinctorial reaction that is readily viewed by routine light microscopy, leading pathologists to categorize the result as nothing more than a novel "special stain," akin to a trichrome stain or a periodic acid-Schiff stain. The introduction of the hybridoma method 4 yielded a bounty of new antibodies, dozens of new "stains," a burgeoning crop of new investigators, innovative variants of the method, new commercial vendors, easy to use "staining kits," and even "automated stainers." Over the last 2 decades the growth of literature in the field was explosive; it was an exciting time. One unintended consequence was that immunohistochemical stains were performed with beguiling ease in growing number of laboratories, with minimal attention to specimen acquisition, sample preparation (fixation), protocol, and controls, following a "modus operandi" that for more than a century had sufficed in the histopathology laboratory for an hematoxylin and eosin stain. As a result reproducibility suffered.

From the very beginning of immunoperoxidase-based studies, describing the immunohistochemical demonstration and distribution of various "antigens" in formalin-fixed tissues, findings were quite readily reproduced by other investigators; to be precise, they were reproduced, but they were not strictly reproducible. Thus, a tinctorial reaction (stain) might be reproduced by different investigators, but the intensity, distribution, and overall quality were inconsistent, from laboratory to laboratory, from day to day, from tissue to tissue within the same laboratory, and even in different regions of a single tissue section. This observed variability was attributed to uncertain quality of the primary antibody (from the same or different sources), to vagaries of technique, the aptitude or ineptitude of the investigator, or to differences in fixation, or lack thereof.

A number of workshops were convened over the years to examine these issues. The Biologic Stain Commission, working with the Food and Drug Administration, sponsored a series of conferences for investigators and manufacturers, at a number of which the author was privileged to be present, as the proverbial fly on the wall, and scribe. One tangible result was a major improvement in the validation and description of primary and labeling antibodies by manufacturers, culminating in more complete and uniform product labeling, incorporated into a comprehensive "package insert." (5) A second outcome was the realization that, to improve the reproducibility of an "immunohistochemical stain," the anatomic pathology laboratory must begin to adopt the standards and the "standardized" procedures of the clinical pathology laboratory. This notion was expressed under the tenet of the "Total Test," (6) which advocated that the performing laboratory assume responsibility for all steps of the immunohistochemical procedure, from specimen acquisition, through sample preparation, fixation, processing, reagent validation, staining, and interpretation, specifically including the proper use of controls.

For a period in the 1980s, the effects of formalin fixation, for good or for ill, had held center stage. Frozen section methods were championed for a few short years, but never could overcome the poor morphologic detail inherent to this approach. Different fixatives were explored with little real success, and attention shifted to efforts intended to minimize the adverse effects of formalin fixation. Enzyme digestion methods yielded dramatic improvement in "staining" intensity in the hands of some investigators, but scarcely improved the reproducibility of immunohistochemistry as a whole. The introduction of "antigen retrieval" (7) (review Ref. 8) changed everything. Antigens that hitherto could not be stained in formalin paraffin sections, now stained; antibodies that did not work on fixed tissues now gave clear staining reactions, in even the least experienced hands. Overnight, pathologists could perform several hundred immunohistochemical "stains" on formalin paraffin sections. But there was another unintended consequence. With the effectiveness of retrieval methods pathologists concluded that they no longer needed to be overly concerned with fixation, so they were not, and once more fixation was ignored.

This state of affairs remained unchallenged for a number of years, for as long as immunohistochemical methods were employed simply as "stains" of lineage related markers of different cell types and their corresponding neoplasms. However, in the offing there was a new driver of change. In the mid-1990s estrogen and progesterone receptor analyses were adapted to the formalin paraffin tissue sections, superseding earlier cytosol-based methods. The effect was to create a new application of immunohistochemistry, namely the demonstration of prognostic and predictive markers. Suddenly, there were increased demands for reproducibility of immunohistochemical "stains," to the point that quantification of expression levels of prognostic markers might be possible; that is measurement of actual amounts of protein within cells. In effect, the requirement was that the immunohistochemical stain should be upgraded from a simple qualitative "stain," to a tissue-based, quantitative, immunologic assay, with all of the stringency thereby implied. It no longer sufficed to demonstrate that a particular marker (e.g., keratin, or CD20) was present (or absent) by the observation of staining (or lack thereof); the question became one of a higher order—exactly how much of the marker (read analyte) was present? Initial scoring methods for estrogen and progesterone receptor were at best semiquantitative, and were difficult to reproduce, in part because of inconsistency among different observers, but more critically because the underlying immunohistochemical staining process was inherently flawed. Experts reconvened, parallels were drawn once more with quantitative immunologic assays (enyzyme-linked immunosorbent assay) in the clinical laboratory, and the "Total Test" approach for immunohistochemical stains was resurrected. In effect the debate over the desirability of standardization was over, the reality of rigorous test performance had arrived. (2,3) This time around there was a consensus that the inherent poor reproducibility had 2 major causes. First, specimen acquisition and sample preparation, including fixation, was entirely uncontrolled and highly variable within, and among, institutions. Second, although "in house" tissue controls were in use, there was a lack of suitable universal controls to assure reliability and reproducibility among different laboratories, and there were no quantifiable reference standards to provide a basis for accurate measurement of analytes.

Additional impetus and urgency arose from the realization that awareness of the poor reproducibility of immunohistochemical methods for the first time extended beyond the pathology community. Thus, colleagues in basic and clinical research voiced frustration upon encountering great variability of results for "tests" such as Her2 expression, which were considered critical for entry into certain clinical trials. This frustration found overt expression in recent requests for proposals from the NIH for studies of sample preparation, in the context of improving the reliability of molecular assays of cancerous tissues. (9) Pathologists around the globe have developed external quality control systems (UKNEQAS, CAP, referenced in the Report 1), that have resulted in demonstrable improvements in quality assurance of the staining method, but cannot address the adequacy or otherwise of sample preparation and fixation. At the time of writing new guidelines for the practice of immunohistochemistry are being formulated (Clinical Laboratory Standards Institute and College of American pathologists), to replace those existing, (10) but these large organizations by their very nature are somewhat deliberate in thought and action.

REFERENCES

1. Goldstein N S, Hewitt S M, Taylor C R, et al, Members of Ad-Hoc Committee On Immunohistochemistry Standardization. Recommendations for improved standardization of immunohistochemistry. Appl Immunohistchem Mol. Morph. 2007.
2. Taylor C R. Quantifiable internal reference standards for immunohistochemistry: the measurement of quantity by weight. Appl Immunohistochem Mol. Morphol. 2006; 14:253-259.
3. Taylor C R, Levenson R M. Quantification of immunohistochemistry-issues concerning methods, utility and semi-quantitative assessment II. Histopathology. 2006; 49:411-424.
4. Kohler G, Milstein C. Continuous cultures of fused cells secreting antibody of predefined specificity. Nature. 1975; 256:495-497.
5. Taylor C R. Report of the Immunohistochemistry Steering Committee of the Biological Stain Commission. "Proposed format: package insert for immunohistochemistry products." Biotech Histochem. 1992; 67:323-338.
6. Taylor C R. Quality assurance and standardization in immunohistochemistry. A proposal for the annual meeting of the Biological Stain Commission, June, 1991. Biotech Histochem. 1992; 67:110-117.
7. Shi S R, Key M E, Kalra K L. Antigen retrieval in formalin fixed paraffin embedded tissues. J Histochem Cytochem. 1991; 39:741-748.
8. Shi S R, Cote R J, Taylor C R. Antigen retrieval immunohistochemistry and molecular morphology in the year 2001. Appl Immunohistochem Mol Morphol. 2001; 9:107-116.
9. National Institutes of Health. RFA-CA-07-003. Innovations in Cancer Sample Preparation, US, National Cancer Institute, 2006.
10. O'Leary T J, Edmonds P, Floyd A D, et al. Quality Assurance for Immunocytochemistry: Approved Guidelines. Wayne Pa. NCCLS (now www CLSI), 1999.

What is claimed is:

1. A method of determining the amount of a test antigen by immunohistochemistry (IHC), comprising:
   providing a formalin-fixed, paraffin-embedded (FFPE) cell or tissue sample comprising the test antigen and a quantifiable internal reference standard (QIRS) for the test antigen, the QIRS being a second antigen different from the test antigen, the FFPE sample having been prepared at a time $T_1$ from an original cell or tissue sample having an original amount of the test antigen and an original amount of the QIRS;
   providing a reference calibration curve comprising at least a ratio that relates the amount of the test antigen to the amount of the QIRS in a reference FFPE sample at a time $T_2$ after $T_1$;
   measuring a first IHC signal corresponding to the QIRS in the FFPE sample at time $T_2$, wherein the first IHC signal having a magnitude that varies in proportion to at least the concentration of the QIRS;
   measuring a second IHC signal corresponding to the test analyte in the FFPE sample at time $T_2$, wherein the second IHC signal having a magnitude that varies in proportion to at least the concentration of the test analyte; and
   calculating the amount of the test antigen in the FFPE sample by applying the ratio(s) of the calibration curve as a conversion factor.

2. The method of claim 1, wherein the calibration curve provides a ratio, A, of the original amount of the test antigen to the original amount of the QIRS and a ratio, C, of the original amount of the QIRS to the amount of the QIRS in the FFPE sample at time $T_2$ is known, and the amount the test antigen in the original sample is calculated by multiplying the amount QIRS in the FFPE sample by the ratio A and by the Ratio C.

3. The method of claim 1, wherein the original cell is an endothelial cell or the original tissue contains endothelial cells.

4. The method of claim 3, wherein the QIRS is selected from the group consisting of CD31, actin, B2 microglobulin, vimentin, factor VIII, histone H1, MIB1, Fli 1, CD34, and VWF.

5. The method of claim 1, wherein the QIRS is a cell surface protein, a cytoplasmic protein, or a nuclear protein.

* * * * *